(12) United States Patent
Nelson et al.

(10) Patent No.: US 10,792,486 B2
(45) Date of Patent: Oct. 6, 2020

(54) MEDICAL CONNECTOR

(71) Applicant: ICU Medical, Inc., San Clemente, CA (US)

(72) Inventors: David Nelson, Laguna Beach, CA (US); Joseph K. Walker, Pleasant Grove, UT (US)

(73) Assignee: ICU Medical, Inc., San Clemente, CA (US)

( * ) Notice: Subject to any disclaimer, the term of this patent is extended or adjusted under 35 U.S.C. 154(b) by 145 days.

(21) Appl. No.: 16/187,032

(22) Filed: Nov. 12, 2018

(65) Prior Publication Data

US 2019/0076639 A1 Mar. 14, 2019

Related U.S. Application Data

(63) Continuation of application No. 14/708,098, filed on May 8, 2015, now Pat. No. 10,179,231, which is a continuation of application No. PCT/US2013/069312, filed on Nov. 8, 2013.

(60) Provisional application No. 61/725,427, filed on Nov. 12, 2012, provisional application No. 61/798,447, filed on Mar. 15, 2013.

(51) Int. Cl.
*A61M 39/04* (2006.01)
*A61M 39/26* (2006.01)

(52) U.S. Cl.
CPC .......... *A61M 39/045* (2013.01); *A61M 39/26* (2013.01); *A61M 2039/263* (2013.01)

(58) Field of Classification Search
CPC .......... A61M 2039/263; A61M 39/045; A61M 39/26; A61M 2039/0063; A61M 2039/1072; A61M 39/10
See application file for complete search history.

(56) References Cited

U.S. PATENT DOCUMENTS

| | | | |
|---|---|---|---|
| 4,917,668 A | 4/1990 | Haindl | |
| 5,462,255 A | 10/1995 | Rosen et al. | |
| 5,820,601 A | 10/1998 | Mayer | |
| 6,050,978 A | 4/2000 | Orr et al. | |
| 6,079,432 A | 6/2000 | Paradis | |

(Continued)

FOREIGN PATENT DOCUMENTS

| | | |
|---|---|---|
| EP | 1 747 796 | 1/2007 |
| WO | WO 1997/00702 | 1/1997 |

(Continued)

OTHER PUBLICATIONS

Invitation to Pay Addition Fees, re PCT Application No. PCT/US13/69312, dated Jan. 31, 2014.

(Continued)

*Primary Examiner* — Brandy S Lee
(74) *Attorney, Agent, or Firm* — Knobbe, Martens, Olson & Bear, LLP

(57) ABSTRACT

A medical connector for use in a fluid pathway includes a housing configured to permit fluid flow between a first medical device and a second device or location. The medical connector includes a valve member configured to be positioned at least partially within the housing. The valve member is configured to receive the first medical device. The valve member can be moved into a second state. The connector can be adapted for use with a catheter assembly.

13 Claims, 51 Drawing Sheets

(56) References Cited

U.S. PATENT DOCUMENTS

| | | |
|---|---|---|
| 6,168,137 B1 | 1/2001 | Paradis |
| 6,210,624 B1 | 4/2001 | Mayer |
| 6,267,754 B1 | 7/2001 | Peters |
| 6,997,917 B2 | 2/2006 | Niedospial, Jr. et al. |
| 8,162,914 B2 | 4/2012 | Kraushaar et al. |
| 8,177,760 B2 | 5/2012 | Rome et al. |
| 8,197,452 B2 | 6/2012 | Harding et al. |
| 8,197,466 B2 | 6/2012 | Yokota et al. |
| 8,277,424 B2 | 10/2012 | Pan |
| 8,286,657 B2 | 10/2012 | Belley et al. |
| 8,287,518 B2 | 10/2012 | Kitani et al. |
| 8,298,195 B2 | 10/2012 | Peppel |
| 8,337,483 B2 | 12/2012 | Harding et al. |
| 8,361,408 B2 | 1/2013 | Lynn |
| 8,366,658 B2 | 2/2013 | Davis et al. |
| 8,366,676 B2 | 2/2013 | Harding et al. |
| 8,377,010 B2 | 2/2013 | Harding et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,165 B2 | 4/2013 | Niedospial, Jr. et al. |
| 8,529,524 B2 | 9/2013 | Newton et al. |
| 8,636,720 B2 | 1/2014 | Truitt et al. |
| 8,671,964 B2 | 3/2014 | Py |
| 8,684,994 B2 | 4/2014 | Lev et al. |
| 8,702,675 B2 | 4/2014 | Imai |
| 8,715,222 B2 | 5/2014 | Truitt et al. |
| 8,715,247 B2 | 5/2014 | Mansour et al. |
| 8,721,627 B2 | 5/2014 | Albert |
| 8,764,731 B2 | 7/2014 | Burgess et al. |
| 8,801,678 B2 | 8/2014 | Panian et al. |
| 8,834,432 B2 | 9/2014 | Winsor et al. |
| 8,840,577 B1 | 9/2014 | Zollinger et al. |
| 8,864,725 B2 | 10/2014 | Ranalletta et al. |
| 8,870,846 B2 | 10/2014 | Davis et al. |
| 8,876,784 B2 | 11/2014 | Cote, Sr. et al. |
| 8,882,742 B2 | 11/2014 | Dikemn et al. |
| 8,910,919 B2 | 12/2014 | Bonnal et al. |
| 8,951,233 B2 | 2/2015 | Mansour |
| 8,968,261 B2 | 3/2015 | Kimball et al. |
| 8,968,271 B2 | 3/2015 | Guala |
| 8,974,425 B2 | 3/2015 | Tachizaki et al. |
| 8,979,804 B2 | 3/2015 | Ho et al. |
| 9,017,288 B1 | 4/2015 | Starnes |
| 9,017,295 B2 | 4/2015 | Pan |
| 9,032,997 B2 | 5/2015 | Abura et al. |
| 9,039,047 B2 | 5/2015 | Imai |
| 9,044,585 B2 | 6/2015 | Masuda et al. |
| 9,061,130 B2 | 6/2015 | Truitt et al. |
| 9,067,049 B2 | 6/2015 | Panian et al. |
| 9,089,680 B2 | 7/2015 | Ueda et al. |
| 9,095,679 B2 | 8/2015 | Nishimura et al. |
| 9,114,244 B2 | 8/2015 | Yeh et al. |
| 9,119,950 B2 | 9/2015 | Mansour et al. |
| 9,138,572 B2 | 9/2015 | Zeytoonian et al. |
| 9,144,672 B2 | 9/2015 | Mansour et al. |
| 9,162,029 B2 | 10/2015 | Zollinger |
| 9,198,831 B2 | 12/2015 | Rogers |
| 9,212,772 B2 | 12/2015 | Ho et al. |
| 9,220,882 B2 | 12/2015 | Belley et al. |
| 9,234,616 B2 | 1/2016 | Carrez et al. |
| 9,238,128 B2 | 1/2016 | Yamaguchi et al. |
| 9,289,588 B2 | 3/2016 | Chen |
| 9,314,604 B2 | 4/2016 | Bonnal et al. |
| 9,345,641 B2 | 5/2016 | Krause et al. |
| 9,370,466 B2 | 6/2016 | Garfield et al. |
| 9,370,651 B2 | 6/2016 | Zollinger et al. |
| 9,393,398 B2 | 7/2016 | Truitt et al. |
| 9,409,007 B2 | 8/2016 | Yeh |
| 9,707,378 B2 | 7/2017 | Leinsing et al. |
| 2004/0006330 A1 | 1/2004 | Fangrow |
| 2005/0151105 A1 | 7/2005 | Ryan et al. |
| 2006/0161115 A1 | 7/2006 | Fangrow |
| 2007/0043334 A1 | 2/2007 | Guala |
| 2010/0241088 A1 | 9/2010 | Ranalletta et al. |
| 2010/0292673 A1 | 11/2010 | Korogi et al. |
| 2011/0282302 A1* | 11/2011 | Lopez .............. A61M 39/16 604/247 |
| 2011/0295235 A1 | 12/2011 | Fangrow |
| 2011/0319859 A1 | 12/2011 | Zeytoonian et al. |
| 2012/0109077 A1 | 5/2012 | Ryan |
| 2012/0130305 A1 | 5/2012 | Bonnal et al. |
| 2012/0153201 A1 | 6/2012 | Larose et al. |
| 2012/0172806 A1 | 7/2012 | Woehr et al. |
| 2012/0220955 A1 | 8/2012 | Maseda et al. |
| 2012/0220984 A1 | 8/2012 | Christensen et al. |
| 2012/0316536 A1 | 12/2012 | Carrez et al. |
| 2013/0030386 A1 | 1/2013 | Panian et al. |
| 2013/0053815 A1 | 2/2013 | Mucientes et al. |
| 2013/0060205 A1 | 3/2013 | Mansour et al. |
| 2013/0079730 A1 | 3/2013 | Mosler et al. |
| 2014/0174578 A1 | 1/2014 | Bonnal et al. |
| 2014/0124087 A1 | 5/2014 | Anderson et al. |
| 2014/0135709 A1 | 5/2014 | Zollinger |
| 2014/0142519 A1 | 5/2014 | Truitt et al. |
| 2014/0155836 A1 | 6/2014 | Truitt et al. |
| 2014/0155837 A1 | 6/2014 | Masuda et al. |
| 2014/0180219 A1 | 6/2014 | Ho et al. |
| 2014/0180258 A1 | 6/2014 | Ho et al. |
| 2014/0207117 A1 | 7/2014 | Ueda et al. |
| 2014/0209197 A1 | 7/2014 | Carrez et al. |
| 2014/0257198 A1 | 9/2014 | Truitt et al. |
| 2014/0261860 A1 | 9/2014 | Heath et al. |
| 2014/0265318 A1 | 9/2014 | Ho et al. |
| 2014/0276455 A1 | 9/2014 | Yeh et al. |
| 2014/0276456 A1 | 9/2014 | Eddy |
| 2014/0276458 A1 | 9/2014 | Mansour et al. |
| 2014/0276459 A1 | 9/2014 | Yeh et al. |
| 2014/0276460 A1 | 9/2014 | Zollinger et al. |
| 2014/0276463 A1 | 9/2014 | Mansour et al. |
| 2014/0276466 A1 | 9/2014 | Yeh et al. |
| 2014/0296794 A1 | 10/2014 | Li |
| 2014/0303602 A1 | 10/2014 | Mansour et al. |
| 2014/0316350 A1 | 10/2014 | Yamaguchi et al. |
| 2014/0358033 A1 | 12/2014 | Lynn |
| 2014/0358073 A1 | 12/2014 | Panian et al. |
| 2014/0371686 A1 | 12/2014 | Sano et al. |
| 2015/0008664 A1 | 1/2015 | Tachizaki |
| 2015/0045746 A1 | 2/2015 | Macy, Jr. et al. |
| 2015/0148756 A1 | 5/2015 | Lynn |
| 2015/0151100 A1 | 6/2015 | Masour |
| 2015/0157848 A1 | 6/2015 | Wu et al. |
| 2015/0190627 A1 | 7/2015 | Ueda et al. |
| 2015/0196749 A1 | 7/2015 | Ziv et al. |
| 2015/0196750 A1 | 7/2015 | Ueda et al. |
| 2015/0202424 A1 | 7/2015 | Harton |
| 2015/0258325 A1 | 9/2015 | Panian et al. |
| 2015/0265829 A1 | 9/2015 | Truitt et al. |
| 2015/0283373 A1 | 10/2015 | Yeh et al. |
| 2015/0297817 A1 | 10/2015 | Guala |
| 2015/0297880 A1 | 10/2015 | Ogawa et al. |
| 2015/0313523 A1 | 11/2015 | Chelak et al. |
| 2016/0000364 A1 | 1/2016 | Mendels et al. |
| 2016/0001056 A1 | 1/2016 | Nelson |
| 2016/0015958 A1 | 1/2016 | Ueda et al. |
| 2016/0015961 A1 | 1/2016 | Mansour et al. |
| 2016/0022977 A1 | 1/2016 | Ueda et al. |
| 2016/0022978 A1 | 1/2016 | Ueda |
| 2016/0030730 A1 | 2/2016 | Mosler et al. |
| 2016/0038730 A1 | 2/2016 | Zollinger |
| 2016/0114147 A1 | 4/2016 | Siopes et al. |
| 2016/0136051 A1 | 5/2016 | Lavi |
| 2016/0158524 A1 | 6/2016 | Quach et al. |
| 2016/0235961 A1 | 8/2016 | Maffei |

FOREIGN PATENT DOCUMENTS

| | | |
|---|---|---|
| WO | WO 2002/04065 | 1/2002 |
| WO | WO 2006/052655 | 5/2006 |

(56) References Cited

OTHER PUBLICATIONS

Search Report and Written Opinion, re PCT Application No. PCT/US13/69312, dated Mar. 27, 2014.
International Preliminary Report on Patentability, re PCT Application No. PCT/US13/69312, dated May 12, 2015.
European Extended Search Report, re EP Application No. 13852588, dated Oct. 10, 2016.

\* cited by examiner

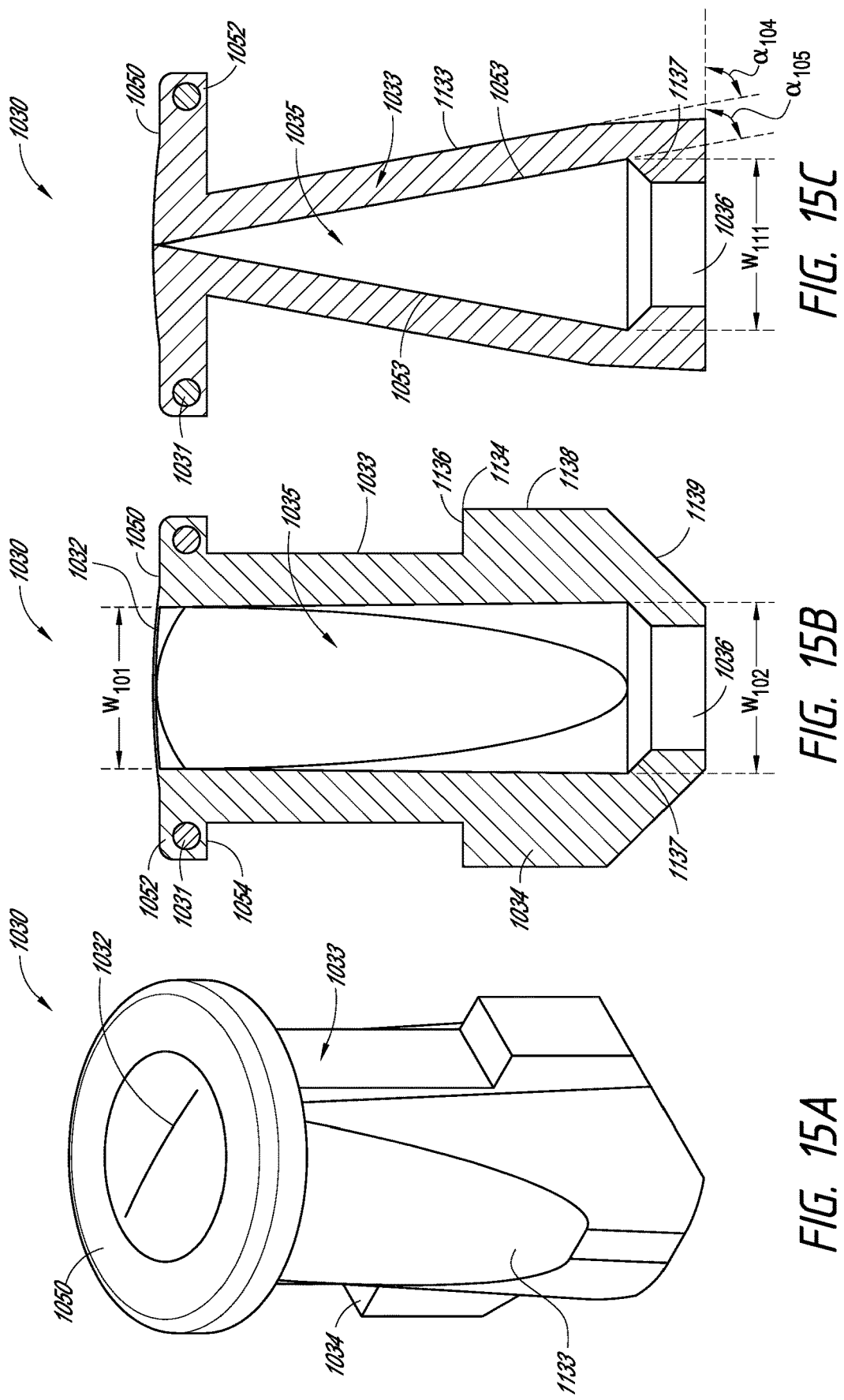

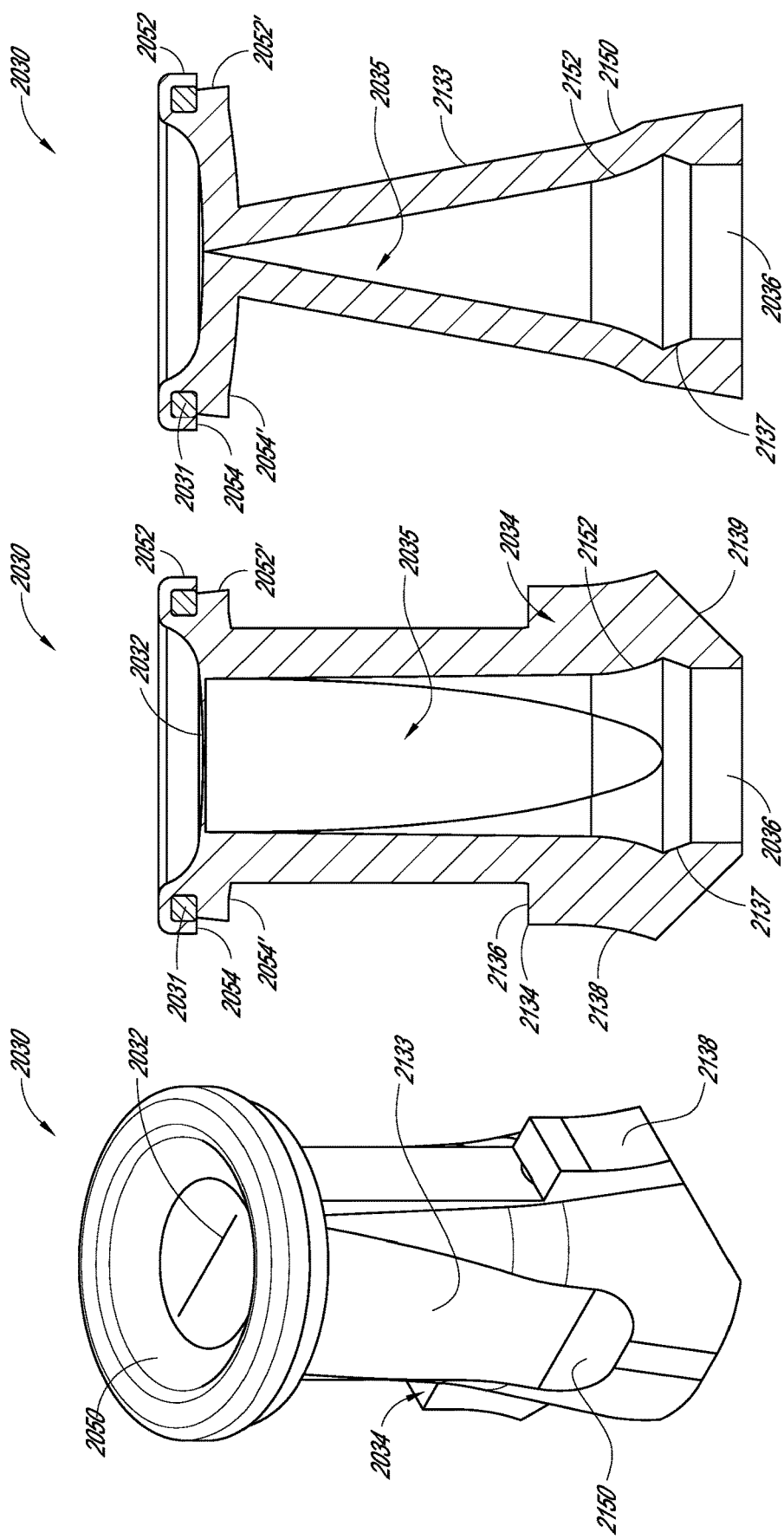

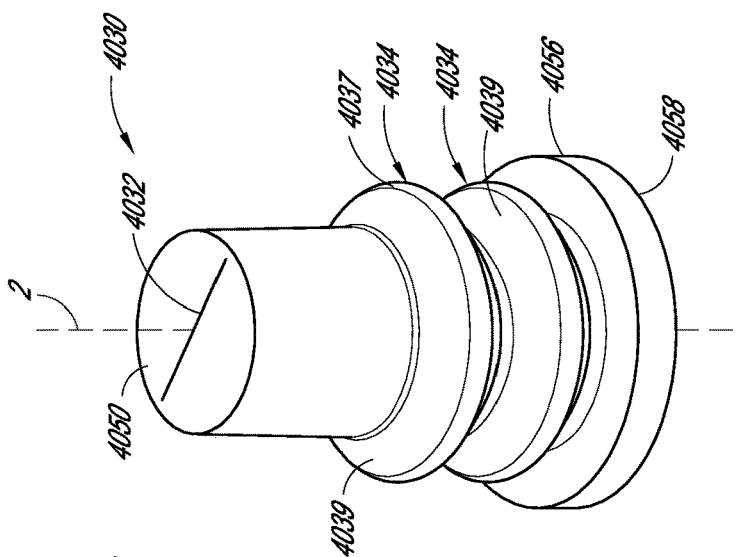
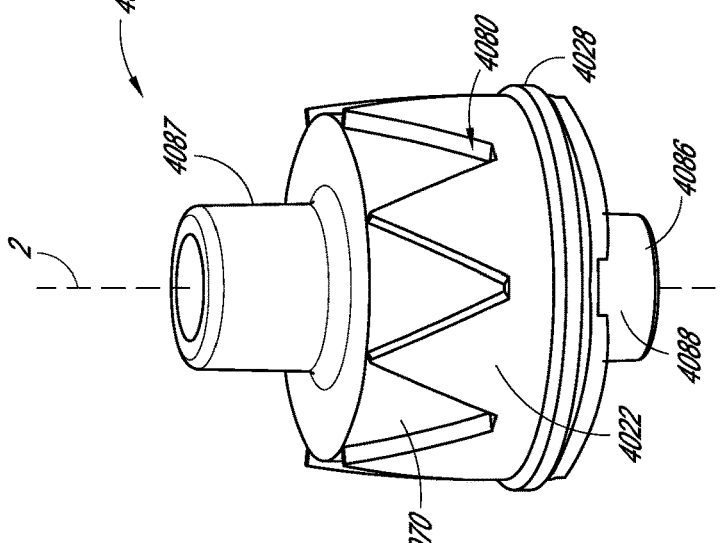
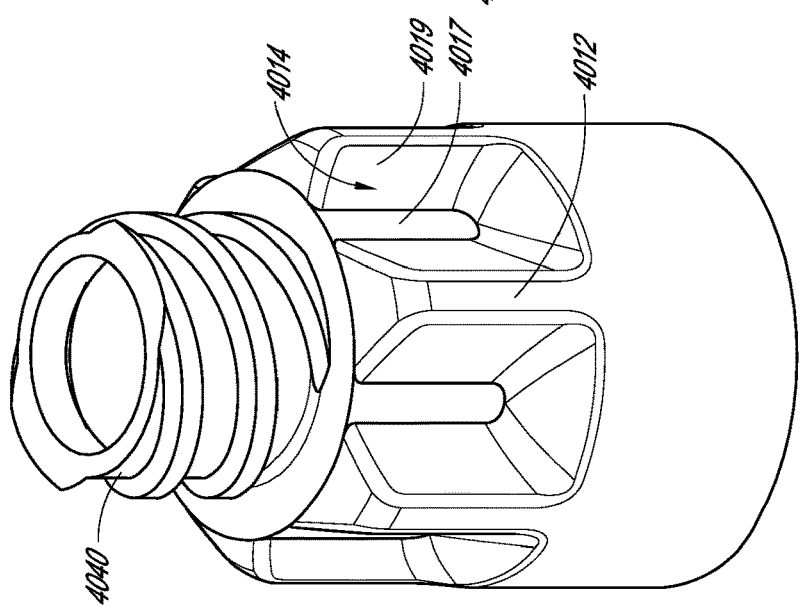
FIG. 23A
FIG. 22
FIG. 21

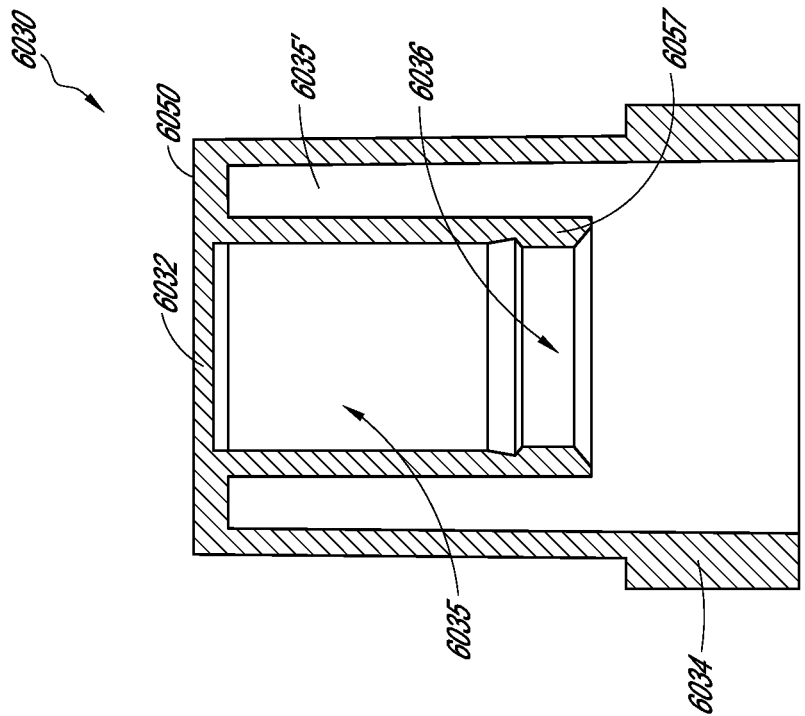
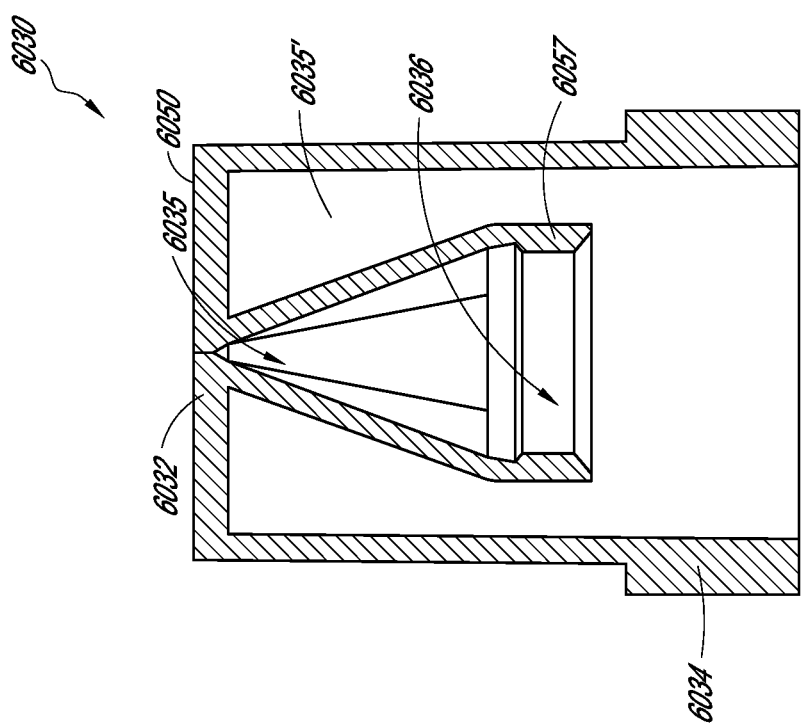
FIG. 31A
FIG. 31B

MEDICAL CONNECTOR

CROSS-REFERENCE TO RELATED APPLICATIONS

This application claims the benefit under 35 U.S.C. § 120 to and is a continuation of U.S. patent application Ser. No. 14/708,098, filed May 8, 2015, titled "MEDICAL CONNECTOR," which claims the benefit under 35 U.S.C. § 120 and 35 U.S.C. § 365(c) as a continuation of International Application No. PCT/US2013/069312, designating the United States, with an international filing date of Nov. 8, 2013, titled "MEDICAL CONNECTOR," which claims the benefit of U.S. Provisional Patent Application No. 61/798,447, filed Mar. 15, 2013, titled "MEDICAL CONNECTOR," and of U.S. Provisional Patent Application No. 61/725,427, filed Nov. 12, 2012, titled "HIGH FLOW RATE MEDICAL CONNECTOR." The entirety of each of the above-mentioned applications is hereby incorporated by reference herein and made a part of this disclosure.

BACKGROUND OF THE DISCLOSURE

Field of the Disclosure

The present disclosure relates in general to the field of medical connectors, and in particular to needleless medical connectors.

Description of the Related Art

The manipulation of fluids in hospitals and medical settings routinely involves the use of connectors for selectively facilitating the movement of fluids to or from patients. Needleless connectors are typically structured so that a medical implement without a needle can be selectively connected to such a connector for providing fluid flow between a patient and a fluid source or receptacle. When the medical implement is removed, the connector closes, effectively sealing the connection to the patient without requiring multiple injections to the patient and without exposing health care professionals to the risk of inadvertent needle sticks. The medical implement used with the connector may be a tube or other medical device such as a conduit, syringe, IV set (both peripheral and central lines), piggyback line, or similar component which is adapted for connection to the medical valve.

Such connectors have various limitations and disadvantages, however, and a need exists for further improvement.

In addition, access to a patient's vasculature with a catheter designed to remain in the vasculature for a period of time often requires an introducer which is removed post-insertion into the vasculature. Catheter hubs may have internal valves that can have compression set where an introducer remains in the valve for an extended period of time prior to removal of the introducer. A need exists for improvement of such catheters.

SUMMARY OF THE DISCLOSURE

In accordance with one embodiment, a medical connector for permitting fluid flow between a first medical device and a second medical device can include a housing having an upper end configured to receive a first medical device and a lower end configured to receive a second medical device; a cannula comprising a lower section with a lower tip and an upper section with an upper tip, the cannula having a variable inner diameter and extending from the lower end of the housing to a position within an interior space of the housing; and a valve member positioned at least partially within an interior space of the housing, the valve member comprising an internal cavity, a top surface, a bottom surface, a slit connecting the top surface and the internal cavity, and an opening on the bottom surface in communication with the internal cavity, the opening positionable around the upper tip of the cannula to create a flow path from the top surface of the valve member to the lower end of the cannula. The inner diameter of the cannula varies between the lower end and the upper section and is constant along the length of the upper section.

The inner diameter of the cannula can decrease from the lower tip to the upper section. In some embodiments, it can decrease at a constant rate from the lower tip to the upper section.

In some embodiments, the housing can include a first housing attached to a second housing, the first housing configured to receive the first medical device and the second housing configured to receive the second medical device. In some embodiments, a gap can exist between the first housing and the second housing, and the gap can be fluidly connected to the interior space to serve as a vent between the interior space and the space outside the first and second housings.

In accordance with one embodiment, medical connector for permitting fluid flow between a first medical device and a second medical device can include an upper housing comprising an upper end configured to receive a first medical device, and at least two downward projections centered about a central longitudinal axis of the upper housing, the at least two downward projections each having a first angular width at a base and alignment surfaces that taper toward an edge at a lower tip of the projection; a seal element fixed to the upper housing; and a lower housing comprising a lower end configured to receive the second medical device, at least two upward projections centered around a central longitudinal axis of the lower housing and each having two alignment surfaces that taper toward an edge at an upper tip of each projection, and at least two gaps having a second angular width and bounded on either side by adjacent upward projections. The upper and lower housings can be configured to be joined together. In some embodiments, the first angular width can be less than the second angular width such that each of the downward projections is configured to fit within one of the at least two gaps.

In some embodiments the first angular width and second angular width are sized such that each of the downward projections fits flush within one of the at least two gaps. In some embodiments, the alignment surfaces of the downward projections and the alignment surfaces of the upward projections are configured such that if the upper and lower housings are misaligned when joined together the alignment surfaces will cause the upper and lower housings to rotate relative to each other until each of the downward projections is aligned with one of the at least two gaps. In some embodiments, the alignment surfaces of the downward and upward projections comprise matching helical surfaces. In some embodiments, the at least two upward projections each comprise an opening passing through the projection. In some embodiments, the seal element includes a central body and two shoulders extending outward from the central body on opposite sides thereof, the shoulders oriented such that when the upper and lower housings are joined each shoulder is aligned with the opening of one of the at least two upward projections.

In accordance with one embodiment, a medical connector for permitting fluid flow between a first medical device and a second medical device can include a housing comprising an upper end configured to receive a first medical device, a lower end configured to receive a second medical device, and a cannula extending from the lower end of the housing to a position within an interior space of the housing; and a valve member attached to the upper end of the housing and positioned at least partially within an interior space of the housing, the valve member having a slit on a top surface thereof that extends into an interior cavity, and an opening to the interior cavity at a bottom surface of the valve member, the valve member having an first state in which the valve member does not reach the cannula and a second state in which the valve member is stretched toward the cannula and the opening is positioned around a portion of the cannula.

In some embodiments, the valve member is molded with the housing such that it is unable to rotate relative to the housing. In some embodiments, the valve member has a central body and two shoulders extending outward from the central body, each shoulder positioned within a corresponding recess within an interior of the housing when the valve member is in the second state, an upper surface of each recess contacting the corresponding shoulder and preventing the valve member from returning to the first state. In some embodiments, the valve member has a domed top when the valve is in the first state and a substantially flat top when the valve is in the second state. The substantially flat top of the valve in the second state can be substantially flush with an upper surface of the housing. In some embodiments, when a first medical device is attached to the upper end of the housing, the opening extends to a position farther down the cannula.

In some embodiments, the upper end of the housing has an upward facing ledge and the valve member has a lip, wherein at least a portion of the lip seats on the ledge. In some embodiments, the valve member has a rigid annular insert positioned at least partially within the lip. In some embodiments, the upward facing ledge is a first ledge and the lip is a first lip, the housing further includes an upper ledge above the first ledge and the valve member further includes an upper lip above and extending past the first lip, and at least of portion of the upper lip seats on the upper ledge.

In accordance with one embodiment, a medical connector for permitting fluid flow between a first medical device and a second medical device can include a housing having an upper end configured to receive a first medical device and a lower end configured to receive a second medical device. A valve member can be attached to the upper end of the housing and positioned at least partially within an interior space of the housing, the valve member having a central body and at least two shoulders extending from the central body on opposite sides thereof. The housing can also have at least two recessed areas therein, and the valve member can have a first state in which the at least two shoulders are each positioned above a respective one of the at least two recessed areas, and a second state in which each shoulder is within the respective one of the at least two recessed areas.

In some embodiments, the housing defines the at least two recessed areas. In some embodiments, an upper surface of each of the at least two recessed areas contacts a respective upper surface of a respective one of the at least two shoulders, preventing the at least two shoulders from returning to the first state. In some embodiments, when a first medical device is attached to the upper end of the housing, each shoulder is removed from contact with an upper surface of the corresponding recess. In some embodiments, the valve member has a domed top when the valve is in the first state and a substantially flat top when the valve member is in the second state.

In accordance with one embodiment, a method of manufacturing a medical connector with a multistep injection molding process can include injection molding a first part of the medical connector around a first sleeve, a second sleeve, and a core pin, the first part formed of a first material; injection molding a second part of the medical connector around the core pin and at least partially within the first sleeve and the second sleeve, the second part formed of a second material; withdrawing the core pin from within the second part; withdrawing the second sleeve from around the second part; withdrawing the first sleeve from around the second part; and removing the first part and the second part.

In some embodiments, the first sleeve at least partially surrounds the second sleeve when the second part is molded. In some embodiments, the core pin and the second sleeve can be withdrawn simultaneously. In some embodiments, the first material is different from the second material. In some embodiments, the core pin can extend past the first sleeve and the second sleeve prior to withdrawing the core pin. In some embodiments, the first part can extend past the first sleeve and the second sleeve. In some embodiments, withdrawing the first sleeve includes moving a section of the first sleeve with an internal width past a section of the second part with an exterior width, wherein the exterior width is greater than the internal width.

In some embodiments, an introducer catheter includes a proximal end comprising a housing with a selectively closed end, such proximal end being configured to transition from a first arrangement to a second arrangement wherein the selectively closed end is able to resist greater fluid pressure in the second arrangement. In some embodiments, the selectively closed end includes an introducer element extending therethrough and the selectively closed end is configured to resist compression set around such introducer element.

Some embodiments provide a method of accessing the vasculature of a patient including the steps of inserting an introducer element surrounded at least in part by a catheter; withdrawing the introducer element from the vasculature while leaving the catheter therein; transitioning a proximal end portion of the catheter from a first arrangement to a second arrangement, in which the proximal end portion in the second arrangement is configured to resist a higher level of fluid flow pressure than in the first arrangement. In some embodiments, the transition from the first arrangement to the second arrangement occurs during the removal of the insertion element. In some embodiments, the transition requires manipulation of a housing portion at the proximal end portion. In some embodiments, the proximal end portion includes a resilient sealing element disposed at least partially outside the proximal end portion.

In some embodiments, an introducer catheter includes a proximal end comprising a housing with a selectively closed end, such proximal end being configured to transition from a first arrangement to a second arrangement wherein the selectively closed end is able to resist greater fluid pressure in the second arrangement. In some embodiments, the selectively closed end includes an introducer element extending therethrough and the selectively closed end is configured to resist compression set around such introducer element.

In accordance with one embodiment, a catheter assembly for insertion of a catheter into a patient can include a catheter hub having a housing with an upper end and a lower end, a valve member positioned at least partially within the housing, the valve member having a top surface, a central body defining an internal cavity, and a slit extending from the top surface to the internal cavity, the valve member configured to transition from a first state in which the valve member has a first length to a second state in which the valve member has a second length, the second length greater than the first length. The catheter assembly can also include a catheter connected to the catheter hub and extending from the lower end of the catheter hub, the catheter in fluid communication with the internal cavity of the valve member. In some embodiments, a needle can extend at least partially through the catheter hub and at least partially through the catheter, the needle having a distal end below the lower end of the catheter hub housing and a proximal end, the needle configured to transition from a non-insertion position to an insertion position. In some embodiments, a needle hub can be attached to the proximal end of the needle. In some embodiments, moving the needle from the non-insertion position to the insertion position transitions the valve member from the first state to the second state.

In some embodiments, the first and second lengths of the valve member can be measured from a bottom surface to the top surface of the valve member, and the second length can be between approximately 1.1 and 1.3 times the first length. In some embodiments, the first and second lengths can be measured from the bottom surface to an uppermost point of the top surface.

In some embodiments, the proximal end of the needle can be above the upper end of the catheter hub housing. In some embodiments, the valve member can include at least two shoulders and the housing can define at least two recessed areas, each recessed area aligned with a respective shoulder. In some embodiments, when the valve member transitions to the second state each shoulder can move into its respective recessed area. In some embodiments, the needle hub can be configured to push the valve member into the second state as the needle moves from the non-insertion position to the insertion position. In some embodiments, the catheter assembly can include a needle guard positioned around the needle. In some embodiments, the needle guard can be positioned at least partially within the internal cavity of the valve member.

In accordance with one embodiment, a catheter assembly for insertion of a catheter into a patient can include a catheter hub having a housing with an upper end and a lower end, the housing defining an interior space and at least two recessed areas within the interior space. The catheter assembly can also include a valve member attached to the upper end of the housing and positioned at least partially within the housing, the valve member having a top surface, a central body defining an internal cavity, a slit extending from the top surface to the internal cavity, and at least two lateral extensions from the central body. A catheter connected to the catheter hub can extend from the lower end of the catheter hub, the catheter configured to fluidly communicate with the internal cavity of the valve member. A needle can extend at least partially through the catheter hub and at least partially through the catheter, the needle having a distal end and a proximal end, the needle further configured to move from a non-insertion position to an insertion position. A needle hub can attach to the proximal end of the needle, and the valve member can be configured to move from a first state in which each lateral extension is above a corresponding recessed area within the interior space of the housing to a second state in which each lateral extension is positioned within the corresponding recessed area.

In some embodiments, when the needle moves toward the insertion position the needle hub can enter the internal cavity of the valve member. In some embodiments, the needle hub can be configured to move the valve member from the first state to the second state. In some embodiments, when the needle moves from the non-insertion position to the insertion position the valve member can move from the first state to the second state. In some embodiments, the catheter assembly can further include a needle guard positioned around the needle. In some embodiments, the needle guard can be positioned at least partially within the internal cavity of the valve member. In some embodiments, the needle can include a notch at its distal end. In some embodiments, the notch can be configured to engage with the needle guard, locking the needle and needle guard together.

In accordance with one embodiment, a catheter assembly for insertion of a catheter into a patient can include a catheter hub with a catheter hub housing having an upper housing and a lower housing, the upper housing and lower housing configured to move relative to each other from a first stage in which the catheter hub housing has a first height to a second stage in which the catheter hub housing has a second height greater than the first height. The assembly can include a valve member having an upper end, a lower end, a bottom surface, a top surface, a central body defining an internal cavity, and a slit extending from the top surface to the internal cavity, wherein the upper end of the valve member is attached to the upper housing and the lower end of the valve member is attached to the lower housing. A catheter can connect to the catheter hub and extend from the lower housing. The catheter can also be in fluid communication with the internal cavity of the valve member. A needle can extend at least partially through the catheter hub and at least partially through the catheter, the needle having a distal end extending from the lower housing and a proximal end extending from the upper housing. And a needle hub can attach to the proximal end of the needle. In some embodiments, removing the needle from the catheter hub can move the catheter hub housing from the first stage to the second stage.

In some embodiments, the lower housing can partially surround the upper housing. In some embodiments, the valve member can have a first height from the bottom surface to the top surface when the catheter hub housing is in the first stage and a second height from the bottom surface to the top surface when the catheter hub housing is in the second stage, the second height greater than the first height. In some embodiments, the first height and second height are measured from the bottom surface to an uppermost point of the top surface. In some embodiments, the second height can be between approximately 1.1 and 1.3 times the first height.

In some embodiments, the valve member can have at least two shoulders extending from the lower end of the valve member, and the lower housing can define at least two recessed areas that each receive a corresponding shoulder. In some embodiments, the assembly can include a needle guard slidably positioned around the needle and at least partially within the internal cavity of the valve member. In some embodiments, pulling the needle guard out of the internal cavity can require a greater force than pulling the needle through the needle guard.

In accordance with one embodiment, a method of using a catheter assembly to insert a catheter into a patient can include providing a catheter assembly, the catheter assembly having a catheter attached to a catheter hub that includes a housing and a valve member, a needle extending at least partially through the catheter hub and at least partially through the catheter, and a needle hub attached to the needle. The method can include inserting the needle hub into the catheter hub, wherein inserting the needle hub into the catheter hub stretches the valve member from a first height to a second height, the second height longer than the first height. The method can also include inserting the needle into a patient, moving the catheter over the needle to insert the catheter into the patient, removing the needle hub from the catheter hub, removing the needle from the patient, and removing the needle from the catheter hub.

In some embodiments, removing the needle hub from the catheter hub and removing the needle from the patient can be done simultaneously. In some embodiments, the housing defines an interior space and includes at least two recessed areas within the interior space, and the valve member can have at least two lateral extensions each configured to fit within a respective recessed area when the valve member is stretched to the second height. In some embodiments, the catheter assembly can include a needle guard positioned around the needle and at least partially within the valve member. In some embodiments, the needle guard can be positioned entirely within the valve member.

In accordance with one embodiment, a method of using a catheter assembly to insert a catheter into a patient can include providing a catheter assembly, the catheter assembly having a catheter attached to a catheter hub that includes a housing with a first housing section and a second housing section configured to move relative to each other from a first stage in which the housing has a first length to a second stage in which the housing has a second length greater than the first length, a needle extending at least partially through the catheter hub and at least partially through the catheter, and a needle hub attached to the needle. In some embodiments, the method can also include inserting the needle into a patient inserting the catheter into the patient, grasping the second housing section, and removing the needle from the catheter hub, wherein removing the needle from the catheter hub moves the catheter hub into the second stage.

In some embodiments, inserting the needle and inserting the catheter into the patient can be done together. In some embodiments, the catheter can extend from the second housing section of the catheter hub housing. In some embodiments, the catheter hub can include a valve member having a central body defining an internal cavity, a slit on a top surface of the valve member that extends into the internal cavity, an upper end, and a lower end, the upper end attached to the upper housing section and the lower end attached to the lower housing section.

In some embodiments, the catheter assembly can include a needle guard positioned at least partially within the internal cavity of the valve member prior to removing the needle from the catheter hub. In some embodiments, the needle guard can be positioned entirely within the internal cavity of the valve member prior to removing the needle from the catheter hub. In some embodiments, removing the needle from the catheter hub can include pulling the needle guard through the slit of the valve member. In some embodiments, the lower end of the valve member can include at least two lateral extensions each positioned within a respective one of at least two recesses defined by the lower housing section, after the needle is removed from the catheter hub.

In accordance with one embodiment, a catheter assembly for insertion of a catheter into a patient can include a catheter hub having a housing and a valve member within the housing, a catheter connected to the catheter hub, a needle extending at least partially through the catheter and the catheter hub, the needle having a proximal end and a distal end, and a needle hub attached to the proximal end of the needle. In some embodiments, the catheter assembly can be configured to transition from a first stage to a second during the process of inserting the needle into a patient and removing the needle from the patient.

In some embodiments, in the first stage the valve member has a first amount of tension along a longitudinal axis of the valve member, and in the second stage the valve member has a second amount of tension along the longitudinal axis of the valve member, the second amount of tension being greater than the first amount of tension. In some embodiments, in the first stage the valve member has a first amount of compression in a plane perpendicular to a longitudinal axis of the valve member, and in the second stage the valve member has a second amount of compression in a plane perpendicular to the longitudinal axis of the valve member, the second amount of compression being greater than the first amount of compression.

In some embodiments, the housing can include a first housing and a second housing configured to move relative to each other. In some embodiments, in the first stage the housing can have a first height and in the second stage the housing can have a second height greater than the first height.

In accordance with one embodiment, a method of using a catheter assembly to insert a catheter into a patient can include providing a catheter assembly, the catheter assembly including a catheter hub having a housing, a catheter connected to the catheter hub, a needle extending at least partially through the catheter and the catheter hub, and a needle hub attached to the proximal end of the needle. The method can include transitioning the catheter assembly from a first stage to a second stage, inserting the needle into a patient, inserting the catheter into the patient, and removing the needle from the patient. In some embodiments, transitioning the catheter assembly from the first stage to the second stage can be performed after inserting the needle into the patient.

In some embodiments, the catheter hub can include a valve member. In some embodiments, in the first stage the valve member can have a first amount of tension along a longitudinal axis of the valve member, and in the second stage the valve member can have a second amount of tension along the longitudinal axis of the valve member, the second amount of tension being greater than the first amount of tension. In some embodiments, in the first stage the valve member can have a first amount of compression in a plane perpendicular to a longitudinal axis of the valve member, and in the second stage the valve member can have a second amount of compression in a plane perpendicular to the longitudinal axis of the valve member, the second amount of compression being greater than the first amount of compression. In some embodiments, the housing can include a first housing and a second housing configured to move relative to each other. In some embodiments, in the first stage the housing can have a first height and in the second stage the housing can have a second height greater than the first height.

BRIEF DESCRIPTION OF THE DRAWINGS

FIG. 15A is a perspective view of one embodiment of a valve member.

FIG. 15B is a cross-sectional view of the valve member of FIG. 15A.

FIG. 15C is a cross-sectional view of the valve member of FIG. 15A taken at about 90 degrees relative to the cross-section of FIG. 15B.

FIG. 17A is a perspective view of one embodiment of a valve member.

FIG. 17B is a perspective view of one embodiment of the valve member of FIG. 17A.

FIG. 17C is a cross-sectional view of the valve member of FIG. 17A taken at about 90 degrees relative to the cross-section of FIG. 17B.

FIG. 21 is one embodiment of an outer body of a medical connector.

FIG. 22 is one embodiment of an inner body of a medical connector.

FIG. 23A is one embodiment of a valve member for use in a medical connector.

FIG. 31A is a cross-sectional view of a valve member for use in the medical connector of FIG. 30.

FIG. 31B is a cross-sectional view of a valve member for use in the medical connector of FIG. 30, taken at about 90 degrees relative to the cross-section of FIG. 32A.

DETAILED DESCRIPTION OF THE PREFERRED EMBODIMENTS

With reference to the attached figures, certain embodiments and examples of high flow rate medical connectors will now be described.

Figure 1:
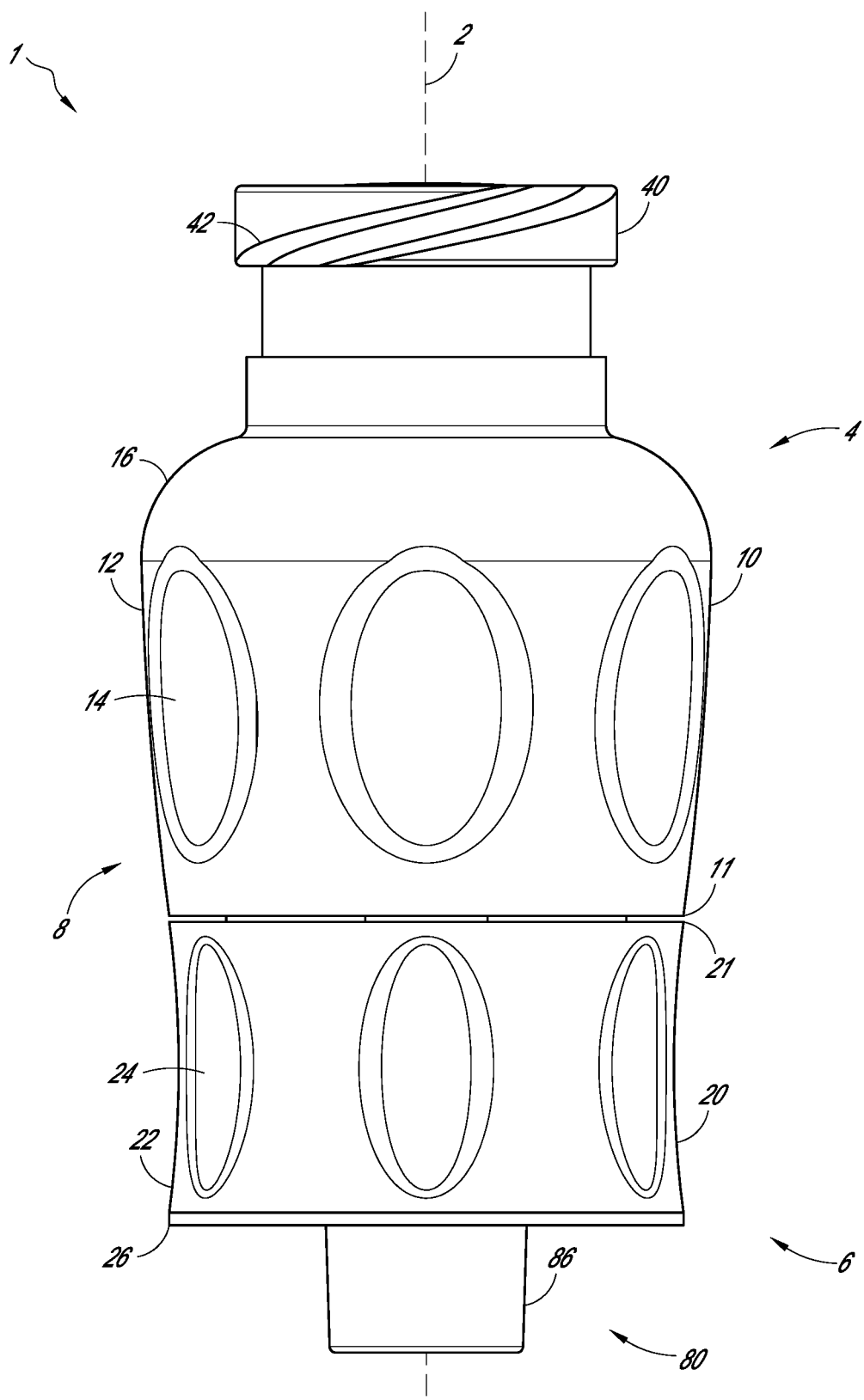
FIG. 1 is a front view of an embodiment of a medical connector.

FIG. 1 illustrates one embodiment of a medical connector 1, which can be centered about a longitudinal axis 2 that can run through the connector. The connector can be described with reference to an upper end 4 and a lower end 6. Although the medical connector in use will not always have the same orientation, the terms "upper" and "lower" as used in this disclosure are with respect to the orientation of the connector and its various components as illustrated in FIG. 1. Similarly, the terms "outer" and "inner" are generally used with reference to the central longitudinal axis 2. Thus, for example, an outermost point of a particular feature in a radial direction would be the point that is farthest from the longitudinal axis.

The medical connector includes a substantially rigid outer housing 8, and in some embodiments the housing 8 comprises a first, or upper, housing 10 and a second, or lower, housing 20. The first housing can have a height that extends parallel to the longitudinal axis 2 from the upper end of shoulder 16, where it joins the upper Luer connector region 40, to the bottom surface 11 of the first housing. The second housing 20 can have a height that extends parallel to the longitudinal axis from the second housing lower edge 26 to the second housing upward surface 21. In the illustrated embodiment, the first housing height is greater than the second housing height. In some embodiments, the second housing height can be approximately ¾ the first housing height, approximately ½ the first housing height, or less. In some embodiments, the second housing height can be greater than the first housing height. Alternatively, in some embodiments the second housing height can be approximately equal to the first housing height.

The first housing 10 and second housing 20 can be designed to increase comfort and grip when holding the medical connector 1. Typically, the connector will be held between the thumb and index finger of a health care professional or other individual manipulating the connector. The housing 8, consequently, can have a generally concave shape along a path from an outermost point of shoulder 16 to the lower edge 26. An example of such a profile is visible in FIG. 1, and the generally concave shape provides a natural position for the fingers used when holding the medical connector 1 and makes it less likely that a user's grip will slip toward the upper or lower portion of the medical connector.

In addition to the general shape of the housing 8, each of the first housing 10 and the second housing 20 can have a separate profile on their respective outer surfaces. For example, the first housing 10 can have a general taper along its outer surface 12 that runs from an outermost point of the shoulder 16 to the bottom surface 11. The outer surface along this path moves consistently closer to the longitudinal axis 2. The second housing 20 can have a generally concave shape along a path on its outer surface 22 from the upper surface 21 to the lower edge 26. In some embodiments, the first housing 10 can have a concave outer surface 12 and the second housing 20 can have an outer surface 22 that tapers from the lower edge 26 toward the upper surface 21. In other embodiments, the first housing 10 and second housing 20 can both have tapering, concave, convex, straight, or other combination of outer surfaces.

Additionally, in some embodiments both housings can have features on their outer surfaces that can improve a user's grip. In the illustrated embodiment, the first housing 10 has dimples 14 and the second housing 20 has dimples 24, although other features can be used such as bumps, ridges, and/or other types of indentations or protrusions. The dimples can be symmetrically spaced around the medical connector 1 such that each dimple has a corresponding dimple on an opposite side of the medical connector. This can allow a user who pinches a medical connector to have a finger on each side of the connector that fits within a dimple. Additionally, as illustrated, in some embodiments the dimples on the second housing 20 are aligned with the dimples on the first housing 10. This can make it easier for a user's fingers to find a position within a dimple if the user adjusts his or her grip from one housing to another.

In some embodiments, the first and second housings can each be configured to connect to a medical device for the purpose of introducing fluid to a patient or withdrawing blood from a patient, or for any other desired purpose. Such medical devices can include but are not limited to IV bags, pierceable connectors, needleless connectors, medical tubing, syringes, etc. The second housing 20 can have a lower Luer connector region 80, discussed in more detail below, which includes a Luer cannula 86. The first housing 10 can have an upper Luer connector region 40 with threads 42 for receiving a threaded medical connector such as a Luer connector of a medical device, such as a syringe.

In various embodiments, the connector regions 40, 80 can generally be configured to accommodate any standard medical connector or implement, and can be configured to conform with ANSI (American National Standards Institute, Washington, D.C.) or other applicable standards. The term "medical implement" is used herein to denote any medical device commonly used in the medical field that can be connected or joined with any embodiments of the connectors disclosed herein. Examples of medical implements that are contemplated include, without limitation, tubing, luers, conduits, syringes, intravenous devices (both peripheral and central lines), closable male luer connectors (both integrally formed with a syringe or independent connectors), pumps, piggyback lines, and other components which can be used in connection with a medical valve or connector. The connector regions can also be configured to have non-standard connections.

The first housing 10 can have a valve member 30, an embodiment of which is illustrated in greater detail in FIG. 3, that seats within the Luer connector region 40 and which can help control and direct a flow of fluid from a first medical device attached to the first housing 10, through the first housing to the second housing 20, and out the Luer cannula 86 to a second medical device attached to the second housing 20. Similarly, it can facilitate flow in the reverse direction.

Figure 2:
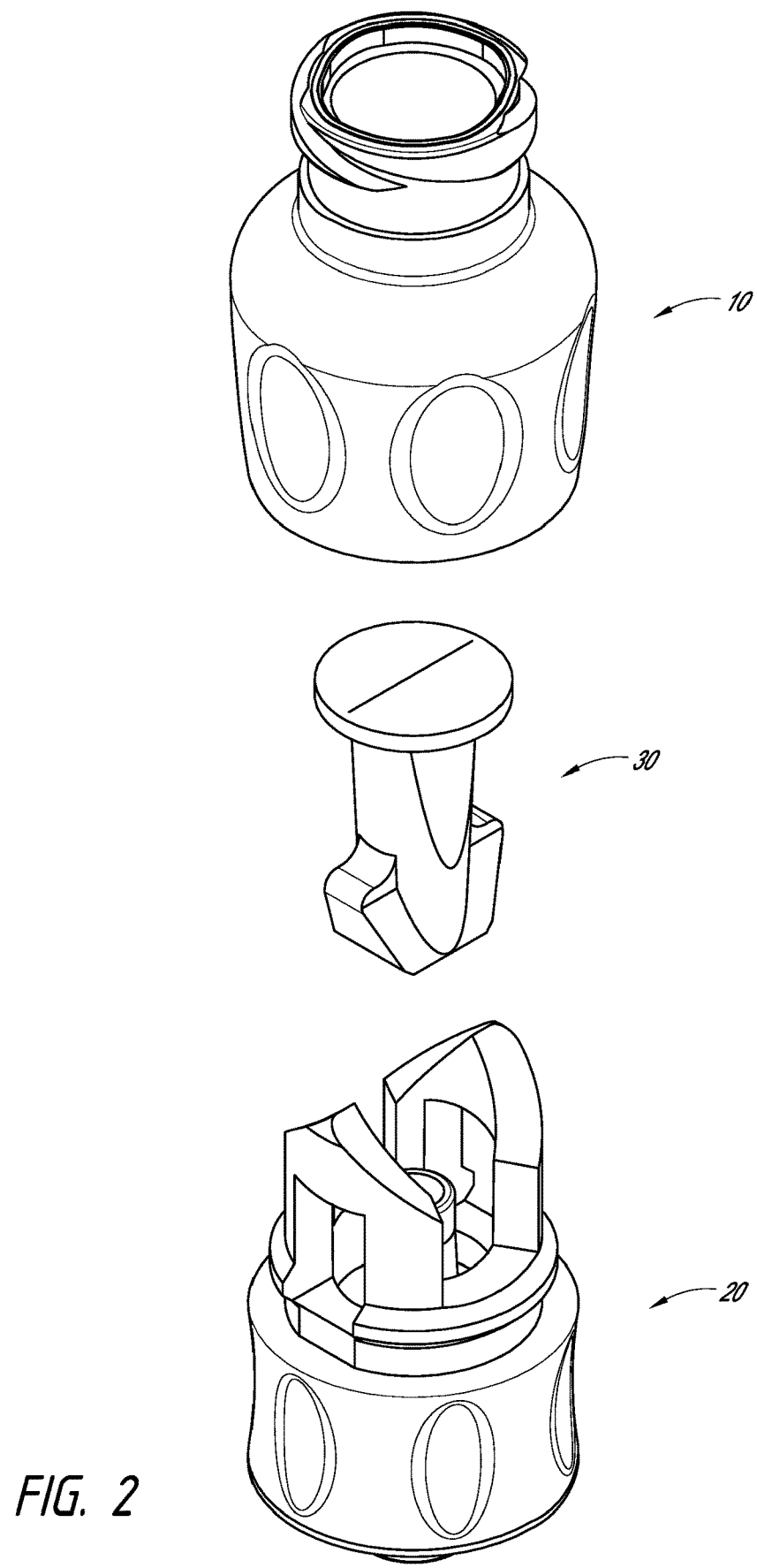
FIG. 2 is an exploded view of an embodiment of a medical connector.

FIG. 2 is an exploded view of an exemplary medical connector 1 that includes the first housing 10, the second housing 20, and a valve member 30 that is located within at least a portion of the first housing when the device is fully assembled. In some embodiments, the valve member 30 can be attached to the first housing 10 from the mold as it is formed. In some embodiments, the valve member and first housing can be formed together as part of a two-shot molding process, discussed in more detail below. Also as discussed below, when the connector is fully assembled the valve member is preferably moved from a first state into a second state within the connector. The following description will first discuss embodiments of these parts (the valve member 30, the first housing 10, and the second housing 20) and will then describe the details of how they can fit together when the device is fully assembled and how they may interact with each other.

Valve Member

FIGS. 3A-4B illustrate one embodiment of a seal element or valve member 30 that can be used with a medical connector 1. The valve member is generally constructed from a flexible material, such as silicon rubber or other material. The valve member can comprise at least one shoulder, or wing, 34 extending outward at a lower end of the valve member. In the illustrated embodiment, the valve member has two shoulders positioned on opposite sides of the valve. The shoulders can be used to help ensure proper positioning of the valve member within the housing of the medical connector, as discussed in more detail below. In some embodiments, three or four or even more shoulders can be used effectively. In some embodiments, a single shoulder may be used.

Figure 3A:
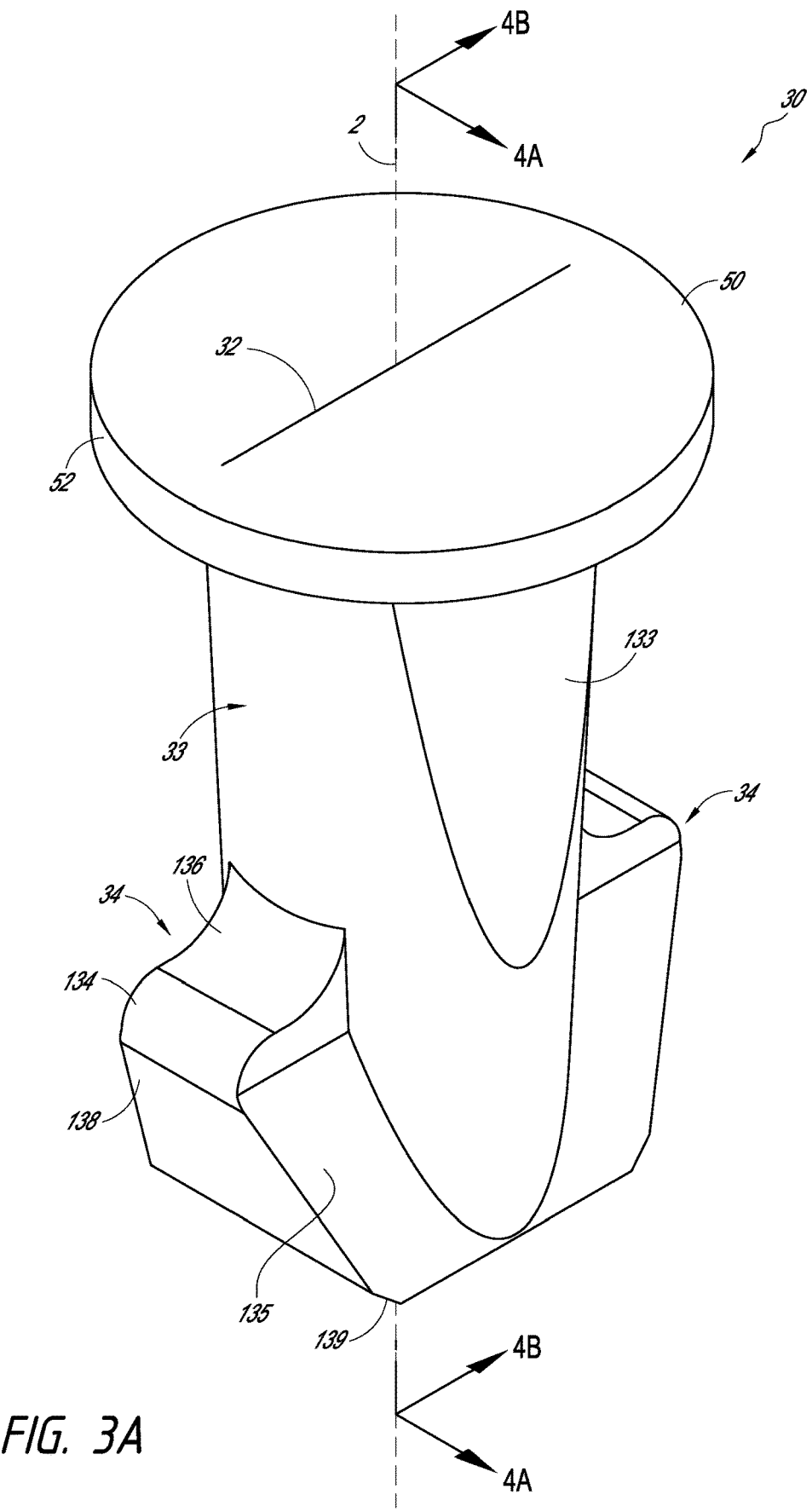
FIG. 3A is a top perspective view of an embodiment of a valve member.

FIG. 3A is a top perspective view of a valve member. As illustrated in FIG. 3A, in some embodiments the shoulders 34 can have a variety of shapes and designs according to desired functional characteristics. In some embodiments, as illustrated, the shoulders can extend from a central body 33 of the valve member 30 along a top surface 136 and toward an outer section 134 of the shoulder. From the outer section, the shoulder can extend toward a base of the valve along a side surface 138. In some embodiments, the side surface 138 can connect to the bottom 58 of the valve through a chamfer 139. In some embodiments, there is no chamfer between the side surface and the bottom of the valve.

As illustrated, in some embodiments the top surface 136 and the outer section 134 can be rounded. As discussed further below, this can help with the process of removing the valve from the mold when formed. Among other benefits, this can help prevent accumulation of stress points in the valve member and can promote easier and more efficient molding of the valve. In some embodiments where the top surface and outer section are rounded, the radius of curvature of the top surface 136 can be greater than the radius of curvature of the outer section 134. In some embodiments, the radius of curvature of the top surface 136 can be less than the radius of curvature of the outer section 134, and in some embodiments the two radii can be approximately equal. In some embodiments, the radius of curvature of the outer section 134 can approach zero such that the outer section 134 becomes an outer edge. In some embodiments, the radius of curvature of the top surface 136 can also or independently approach zero such that the top surface forms a substantially right angle with the central body 33.

In some embodiments, as illustrated, the side surface 138 of the shoulder 34 can be wider at its top than at its bottom, which can create an angled surface 135 on the front of the valve member. This angle can allow for a tapered interlock when the valve is molded, which can hold pressure better and yield a better mold. In some embodiments, the angled surface 135 can extend above the top of the side surface 138, as illustrated.

With continuing reference to FIG. 3A, in some embodiments the central body 33 of the valve member can have a flat section 133 where the wall of the central body has been pushed in relative to other sections of the central body. As illustrated, the flat section 133 can be angled relative to the longitudinal axis 2 of the valve member such that it naturally tapers out. The flat section is preferably angled such that it is wider at its top than at its bottom. The flat section can help ensure room for the valve member to expand within the housing 8 of a medical connector 1 when a medical device is inserted into the valve member, as discussed below.

The valve member can also include a slit 32 extending into the central body 33 of the valve member 30 from the top surface 50. The slit can be configured to naturally remain closed at the top surface but can open to receive a medical device attached to the first housing, thereby facilitating fluid to flow through the valve. This is also discussed in more detail below.

In some embodiments, the valve member can have a lip 52 (also referred to as an upper lip or first lip) that extends out from the central body 33 of the valve at an upper end of the valve. The lip can be used to help seat the valve within a medical connector, as discussed below. In some embodiments, the lip and the valve can have a domed top surface 50, as illustrated, which can allow for the top surface to remain swabbable in embodiments where the valve is placed into tension within the connector, as discussed below.

Figure 3B:
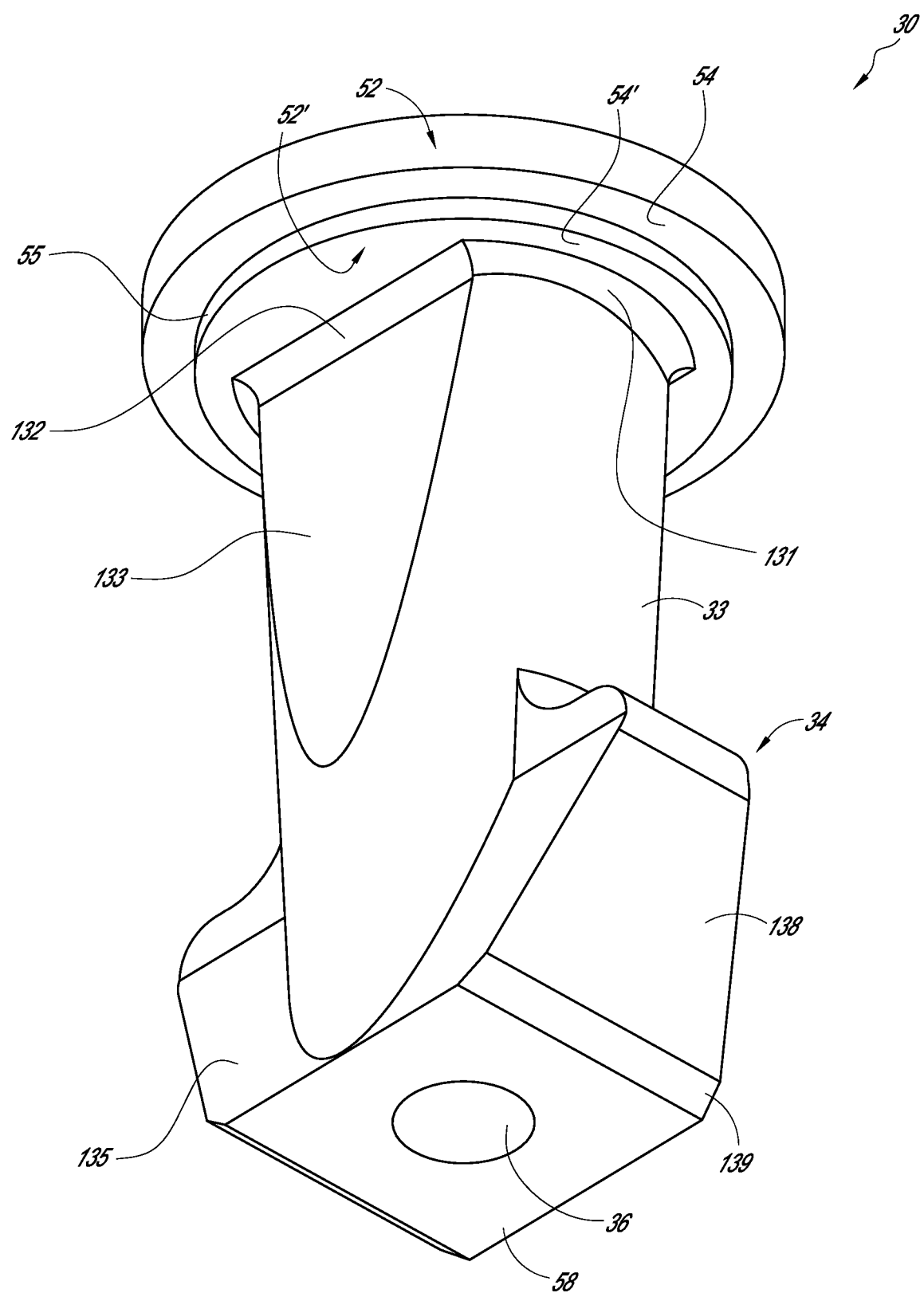
FIG. 3B is a bottom perspective view of the embodiment of FIG. 3A

FIG. 3B illustrates a bottom perspective view of a valve member 30. As illustrated in FIG. 3B, in some embodiments a valve member can have a lower lip or stepped section 52' (also referred to as a second lip) below the lip 52, the lower lip having a lower surface 54' and a side surface 55. In some embodiments, the junction between the lower lip and the central body 33 of the valve member can be a right angle, and in some embodiments it can be curved. In some embodiments, the junction 132 between the between the lower lip and a flat section 133 of the central body 33 can have a different radius of curvature than the junction 131 between the lower lip and other sections of the central body. In some embodiments, a valve member 30 can just have a single lip 52.

Also visible in FIG. 3B is a lead lumen 36 that extends from an opening on the bottom surface 58 of the valve member 30, through the bottom surface, and into an inner cavity of the valve.

Figure 4A:
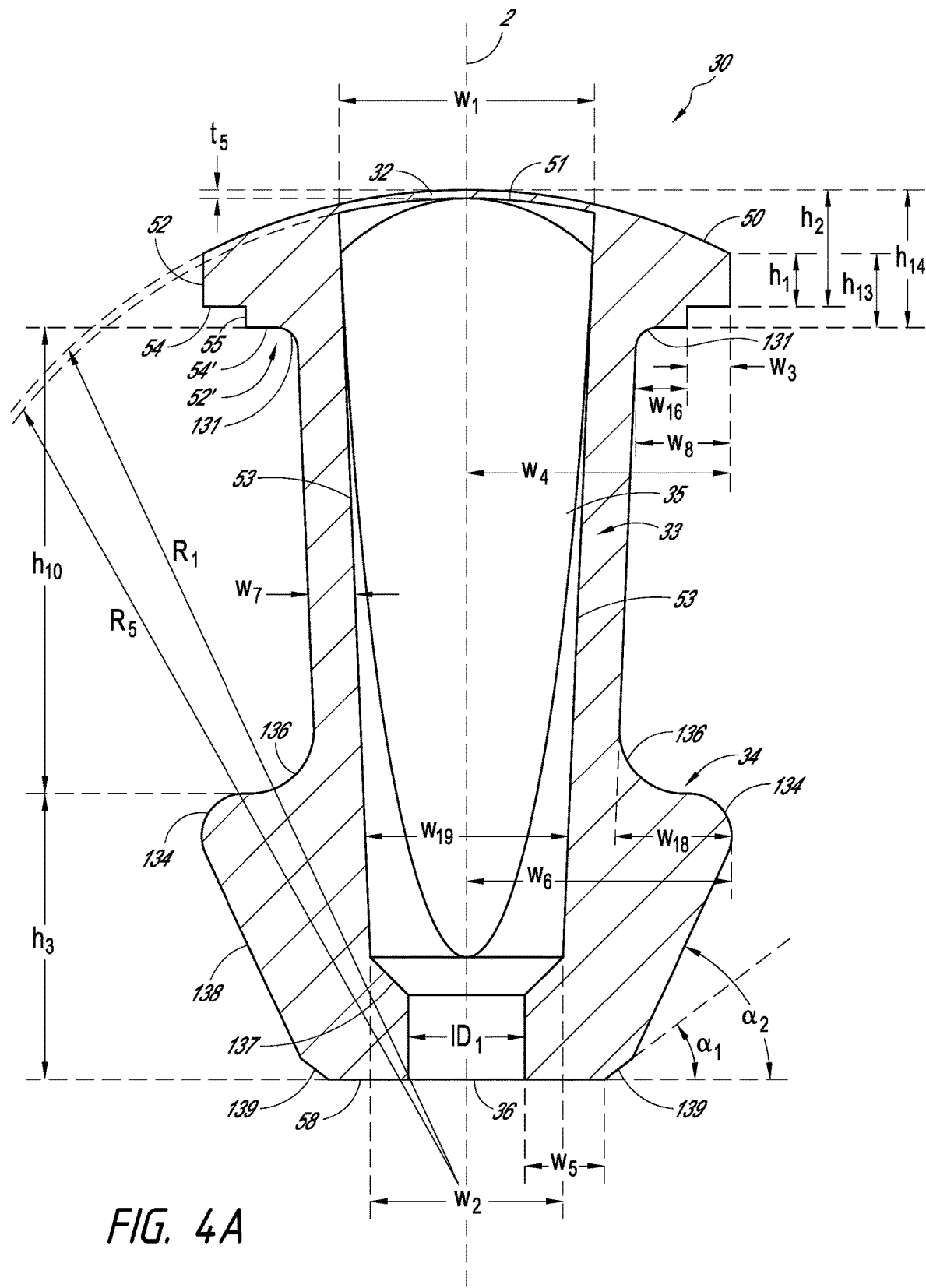
FIG. 4A is a cross-sectional view of the embodiment of FIG. 3A, taken along the line 4A-4A.
Figure 4B:
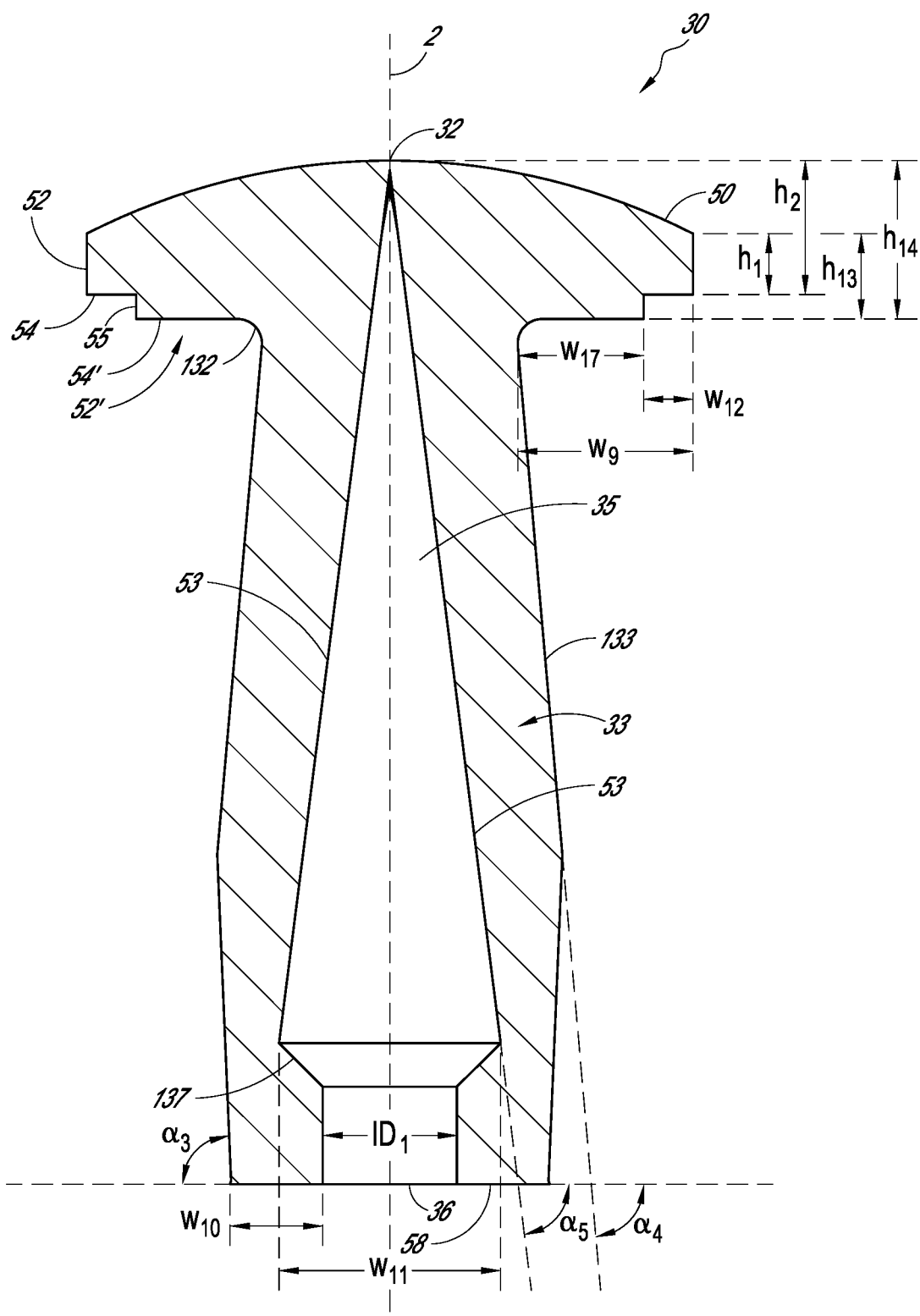
FIG. 4B is a cross-sectional view of the embodiment of FIG. 3A, taken along the line 4B-4B.

FIGS. 4A and 4B illustrate cross-sectional views of the valve member 30 taken along the lines 4A-4A and 4B-4B, respectively, visible in FIG. 3. These cross-sectional views are at approximately 90° relative to each other. As visible in FIG. 4A, the slit 32 can extend from the top surface 50 into the valve to an internal surface 51, creating a passageway through the wall of the valve. In some embodiments, the slit does not extend all the way through the wall of the valve when the valve is molded and a thin layer of valve material can cover the slit on the top surface. This layer is preferably thin enough to be easily broken or to easily pop off.

In some embodiments, discussed in more detail below, the valve member 30 can have a first, generally relaxed, state and a second state in which the valve member is in greater tension along its longitudinal axis 2 than in the first state. In some embodiments, the valve member in the first state may not be in tension along its longitudinal axis. In some embodiments, the valve member in the first state may have tension along the longitudinal axis that is less than the tension in the second state. In some embodiments, the valve member in the first state may not be in compression in a plane perpendicular to its longitudinal axis. In some embodiments, in the second state the valve member can have compression in a plane perpendicular to its longitudinal axis.

In some embodiments, in the plane of the slit 32, the surface or surfaces 53 of the internal cavity 35 of the valve member 30 (also referred to as inner surfaces of the valve member) can narrow slightly until they taper at a tapered section 137, which can run into the lead lumen 36 at a lower end of the valve, as illustrated. Thus, for example, in some embodiments the width $w_1$ of the slit can be greater than the width $w_2$ of the internal cavity 35 adjacent the tapered section 137, when the valve is in a first state. This can help facilitate entry of a medical device, discussed below, and also help direct flow toward the lead lumen 36. In some embodiments, the ratio $w_1/w_2$ of the width of the slit to the width of the internal cavity 35 adjacent the tapered section 137 can be greater when the valve is in the first state than when the valve is in the second state. In some embodiments, the width $w_1$ can be substantially equal to the width $w_2$ when the valve is in the first state, when the valve is in the second state, or both. In some embodiments, the width $w_1$ can increase from the first state to the second state. In some embodiments, the ratio of the width $w_1$ to $w_2$ can be approximately 1.25. In some embodiments, the ratio can be approximately 1.5. In some embodiments, the ratio can be greater than or equal to about 1.1 and/or less than or equal to about 2. In some embodiments, these ratios can describe the valve in either a first state or a second state.

FIG. 4A illustrates a number of other dimensions. For example, visible in FIG. 4A is an upper lip width $w_3$ between the side surface 55 of the lower lip 52' and an outer edge of the lip 52, a width $w_4$ between the central axis 2 and the outer edge of the lip 52, a bottom width $w_5$ in this plane between an outer edge of the lead lumen 36 and an outer edge of the bottom 58 of the valve member, a total shoulder width $w_6$ between the central axis 2 and the outer point of the outer section 134 of the shoulder 34, a net shoulder width $w_{18}$ between the outer point of the outer section 134 of the shoulder and a position aligned with where the top surface 136 of the shoulder 134 begins to extend away from the central body 30, an intermediate internal cavity width $w_{19}$ measured at the same height as the net shoulder width, a width $w_7$ of the walls of the valve body 33 in this plane, a total lip width $w_8$, and an inner diameter $ID_1$ of the lead lumen 36.

In some embodiments, the width $w_7$ of the walls of the central body 33 in this plane can be generally constant between the top surface 136 of the shoulders 34 and the junction 131 between the lower lip and other sections of the central body. In some embodiments, the width $w_7$ of the walls can increase or decrease between the top surface 136 and the junction 131. In various embodiments, the widths described above can vary with respect to each other and also between first and second states of the valve. In some embodiments, the total shoulder width $w_6$ can be greater than the width $w_4$ between the central axis 2 and the outer edge of the lip 52. In some embodiments, the total shoulder width $w_6$ can be less than the width $w_4$ between the central axis 2 and the outer edge of the lip 52. In some embodiments, the ratio $w_6/w_4$ of these widths can be between about 1 and about 1.25, and in other embodiments the ratio can be between about 1 and about 0.8. In some embodiments the ratio can be greater than or equal to about 0.8 and/or less than or equal to about 1.25. Further, in some embodiments, the width $w_7$ of the walls of the central body 33 can be greater when the valve is in a first state than a second state.

In some embodiments the top surface 50 can be a section of a sphere, and have a radius of curvature $R_1$. In some embodiments, the top surface can have a radius of curvature in the illustrated plane that differs from radii of curvature in other planes, such that the top surface is not a section of a sphere. In some embodiments, as illustrated, the radius of curvature can be greater than the height of the valve (the height being the sum of $h_3$, $h_{10}$, and $h_2$), such that the center of curvature is located below the valve. In some embodiments, the radius of curvature can be less than the height of the valve, such that the center of curvature is located within the valve. The radius of curvature can also be substantially equal to the height of the valve. In some embodiments, the radius of curvature can increase when the valve is in a second state. In some embodiments, the radius of curvature can approach infinity when the valve is in a second state such that the top surface 50 of the valve is substantially flat.

Similarly, in some embodiments the internal surface 51 of the section of the valve 30 through which the slit 32 passes can be a section of a sphere and have a radius of curvature $R_s$. In some embodiments, it can have a radius of curvature in the illustrated plane that differs from radii of curvature in other planes. The radius of curvature can vary in different embodiments in the same ways described above with respect to the top surface 50. For example, the internal surface 51 can have a radius of curvature $R_s$ that in various embodiments can have a center of curvature below the base of the valve, approximately at the base of the valve, or within the valve. The radius of curvature can also or alternatively increase when the valve is in a second state, and in some embodiments can be generally flat when the valve is in a second state.

In some embodiments, the radius of curvature $R_s$ of the internal surface 51 can be approximately equal to the radius of curvature $R_1$ of the top surface 51. In such embodiments, the thickness $t_s$ of the slit can be generally consistent along its width $w_1$. In some embodiments, the two radii of curvature can differ such that the thickness $t_s$ of the slit varies along the width $w_1$. In some embodiments, $R_1$ can be greater than $R_2$, and in some embodiments $R_2$ can be greater than $R_1$.

In some embodiments, the ratio of the width of the slit $w_1$ to the slit thickness $t_s$ can vary. In some embodiments, this ratio can be between approximately 4 and approximately 5. In some embodiments, this ratio can be greater than or equal to about 2.5 and less than or equal to about 7.5.

In some embodiments, the ratio of the net shoulder width $w_{18}$ to the intermediate internal cavity width $w_{19}$ can, among other things, affect the ability to withdraw the valve 30 from a mold, as discussed in more detail below. In some embodiments, this ratio can preferably be no greater than 0.5. In some embodiments, however, it can be greater than 0.5. In some embodiments, it can be greater than or equal to about 0.2 and/or less than or equal to about 0.5. In some embodiments, the listed ratios describe the valve when it is in a second state. In some embodiments, they can describe the valve when in a first state.

With continuing reference to FIG. 4A, the upper lip 52 can have a center height $h_2$, measured from the bottom surface 54 of the upper lip to the top point of the top surface 50 of the valve, and the lower lip 52' can have a center height $h_{14}$ measured from the bottom surface 54' of the lower lip to the top point of the top surface of the valve. The upper lip can also have an edge height $h_1$, measured from the bottom surface of the upper lip to the top of the valve at its outer edge.

In some embodiments, the ratio of the upper lip center height $h_2$ to the upper lip edge height $h_1$ can be greater than or equal to about 1.5 and/or less than or equal to about 3. In some embodiments it can be greater than or equal to about 1.2 and/or less than or equal to about 3.5. This ratio can affect the amount to which the radius of curvature $R_1$ of the top surface 50 of the valve changes when the valve is moved to a second state. Similarly, the ratio of the edge height $h_1$ to the upper lip width $w_3$ can affect deformation of the valve member when it is in a tensioned state. In some embodiments, this ratio can be greater than or equal to about 0.5 and/or less than or equal to about 1.5. In some embodiments it can be greater than or equal to about 1 and/or less than or equal to about 3.

In some embodiments, the ratio of the total lip height $h_{13}$ (the sum of the heights of the upper 52 and lower 52' lips) to the lower lip width $w_{16}$ can similarly affect deformation of the valve member when it is in a tensioned state. In some embodiments, this ratio can be greater than or equal to about 1 and/or less than or equal to about 2. In some embodiments, the ratio can be greater than or equal to about 0.5 and/or less than or equal to about 3.

In some embodiments, the ratio of the lower lip center height $h_{14}$ to the total lip height $h_{13}$ can also affect deformation of the valve member and the amount to which the radius of curvature $R_1$ changes when the valve is moved to a second state. In some embodiments, this ratio can be can be greater than or equal to about 1 and/or less than or equal to about 3. In some embodiments, it can be greater than or equal to about 1.5 and/or less than or equal to about 4.

Similarly, the ratio of the core height $h_{10}$ of the valve (measured from the top of the shoulders 134 to the bottom 54' of the lower lip 52') to the total lip height $h_{13}$ can affect how the valve member deforms when in a tensioned state. In some embodiments this ratio can be greater than or equal to about 5 and/or less than or equal to about 7. In some embodiments this ratio can be greater than or equal to about 3 and/or less than or equal to about 9.

The height $h_3$ of the shoulder 34 can be measured from the bottom surface 58 of the valve to the top of the outer section 134 of the shoulder. In some embodiments, the height $h_3$ of the shoulder 34 can be significantly greater than the height $h_1$ of the outer edge of the lip. In some embodiments, their ratio $h_3/h_1$ can be greater than or equal to about 2.5 and/or less than or equal to about 10. In some embodiments, the ratio can be greater than or equal to about 4 and/or less than or equal to about 15. In some embodiments, this ratio can affect how the valve deforms when it is placed in a tensioned state.

Related to the heights and widths of various portions of the valve member 30 is the angle $\alpha_1$ of the chamfer 139 connecting the side surface 138 to the bottom of the valve 58 and the angle $\alpha_2$ of the side surface 138 itself. The side surface angle $\alpha_2$ is generally greater than the chamfer angle $\alpha_1$, and can be correlated with the shoulder width $w_6$ and the shoulder height $h_3$.

FIG. 4B illustrates a cross-sectional view taken at approximately 90° from the view of FIG. 4A. As can be seen in FIG. 4B, in some embodiments in this plane the internal cavity 35 widens as it moves down the valve. Thus, from the bottom of the slit 32, in this plane the surfaces 53 of the internal cavity 35 of the valve 30 can move apart from each other until they reach a maximum width $w_{11}$ at the bottom of the internal cavity, before the tapered section 137 that connects to the lead lumen 36. Preferably, the width $w_{11}$ at the bottom of the internal cavity in this plane is equal to the corresponding width $w_2$ in the plane of FIG. 4A, and this section of the valve forms a circle. In some embodiments, however, these widths can vary. As illustrated, the internal cavity can widen at a generally constant rate, creating cross-sectional views as in FIG. 4B in which the surfaces 53 of the internal cavity are straight. In some embodiments the surfaces can widen at non-constant rates, or may not widen at all. In some embodiments, as illustrated, the surfaces 53 in this plane begin from a common location at the bottom of the slit 32, but in some embodiments they are initially separated. This general profile of the internal cavity—starting from a minimum width and then widening to a desired maximum width—can help limit the priming volume of the valve 30 and medical connector 1.

Also visible in FIG. 4B is an upper lip width $w_{12}$ in this plane, again defined as the distance between the side surface 55 of the lower lip 52' and an outer edge of the upper lip 52, and a lower lip width $w_{17}$. Preferably, the upper lip width $w_{12}$ in this plane is equal to the upper lip width $w_3$ in the plane of FIG. 4A. In some embodiments, however, these widths can vary. The lower lip width $w_{17}$ in this plane is preferably greater than the lower lip width $w_{16}$ in the plane of FIG. 4A, although in some embodiments they can be equal. In some embodiments the lower lip width in this plane is greater than the lower lip width in the plane of FIG. 4A because the valve member 30 has a flat section 133, where the wall of the central body 33 angles in relative to other sections of the central body. The ratio of each total lip width $w_8$, $w_9$ to the edge height $h_1$ of the upper lip 52 can provide some measure of the rigidity of the lip (which can control the shape of the lip and top surface 50 when the valve is placed into tension). These ratios can also affect the ease with which a medical device can be inserted into the valve member 30 and the amount of back pressure sustained within the valve. Also contributing to the features of the valve is the ratio of the larger of the two total lip widths—in this case the ratio $w_9/h_1$ with the total lip width $w_9$ in the plane of FIG. 4B. In some embodiments, the ratio of the total lip width $w_9$ to the edge height $h_1$ can be greater than or equal to about 1.5 and/or less than or equal to about 2. In some embodiments, the ratio can be greater than or equal to about 2 and/or less than or equal to about 5.

Similarly, the ratio of the total lip height $h_{13}$ to the lower lip width $w_{17}$ can also provide a measure of lip rigidity. In some embodiments, this ratio can be between approximately 0.75 and approximately 1.25. In some embodiments, this ratio can be greater than or equal to about 0.5 and/or less than or equal to about 1.5. The ratio of the lower lip center height $h_{14}$ to the lower lip width $w_{17}$ can also provide measures of lip rigidity. In some embodiments, this ratio can be greater than or equal to about 1 and/or less than or equal to about 4. In some embodiments, the ratio can be greater than or equal to about 0.5 and/or less than or equal to about 2.

In some embodiments, it can be preferable for the lower lip width $w_{17}$ to be large enough for the walls of the valve to have room to be displaced when a medical device is inserted into the valve. In some embodiments, the ratio of the lower lip width $w_{17}$ in the plane of FIG. 4B to the lower lip width $w_{16}$ in the plane of FIG. 4A can provide a reflection of this measurement. In some embodiments, this ratio can be greater than or equal to about 1.2 and/or less than or equal to about 3. In some embodiments it can be greater than or equal to about 1.75 and/or less than or equal to about 4.

FIG. 4B also illustrates the angle $\alpha_4$ of the flat section 133 of the valve member 30. Also visible is the angle $\alpha_5$ of the surfaces 53 in this plane of the internal cavity 35. As measured, both angles are relative to a horizontal line on the bottom surface 58 of the valve. In some embodiments, as illustrated, the angle of the flat section 133 and the angle of the inner surfaces 53 in this plane can be different. In some embodiments, as illustrated, the angle $\alpha_5$ of the inner surfaces 53 can be less than the angle $\alpha_4$ of the flat section 133, such that the width of the walls of the central body 33 at the flat section 133 increases as the wall moves toward the top of the valve. This can allow the valve to have greater structural integrity toward the top of the valve, where the internal cavity widens the most to receive a medical device, as discussed below. Similarly, in some embodiments, the angle $\alpha_5$ of the inner surfaces 53 can be less than the angle $\alpha_3$ of the central body 33 below the flat section 133. Thus, below the flat section, the width of the walls of the central body 33 can decrease as the wall moves toward the tapered section 137 of the slit. Alternately, in some embodiments, the angle $\alpha_5$ can be approximately equal to the angle $\alpha_4$ of the flat section 133. In some embodiments, the angle $\alpha_5$ of the inner surfaces 53 can be approximately equal to the angle $\alpha_3$ of the central body 33. In some embodiments, all three angles can be the same.

Also visible in FIG. 4B is a bottom width $w_{10}$ in this plane between an outer edge of the lead lumen 36 and an outer edge of the bottom 58 of the valve member. In some embodiments, the bottom width $w_{10}$ in this plane can be equal to the bottom width $w_5$ in the plane of FIG. 4A. In some embodiments, the bottom width $w_{10}$ in this plane can be less than the bottom width $w_5$ in the plane of FIG. 4A. In some embodiments, as illustrated, the bottom width $w_{10}$ in this plane can be greater than the bottom width $w_5$ in the plane of FIG. 4A.

First Housing

Figure 5:
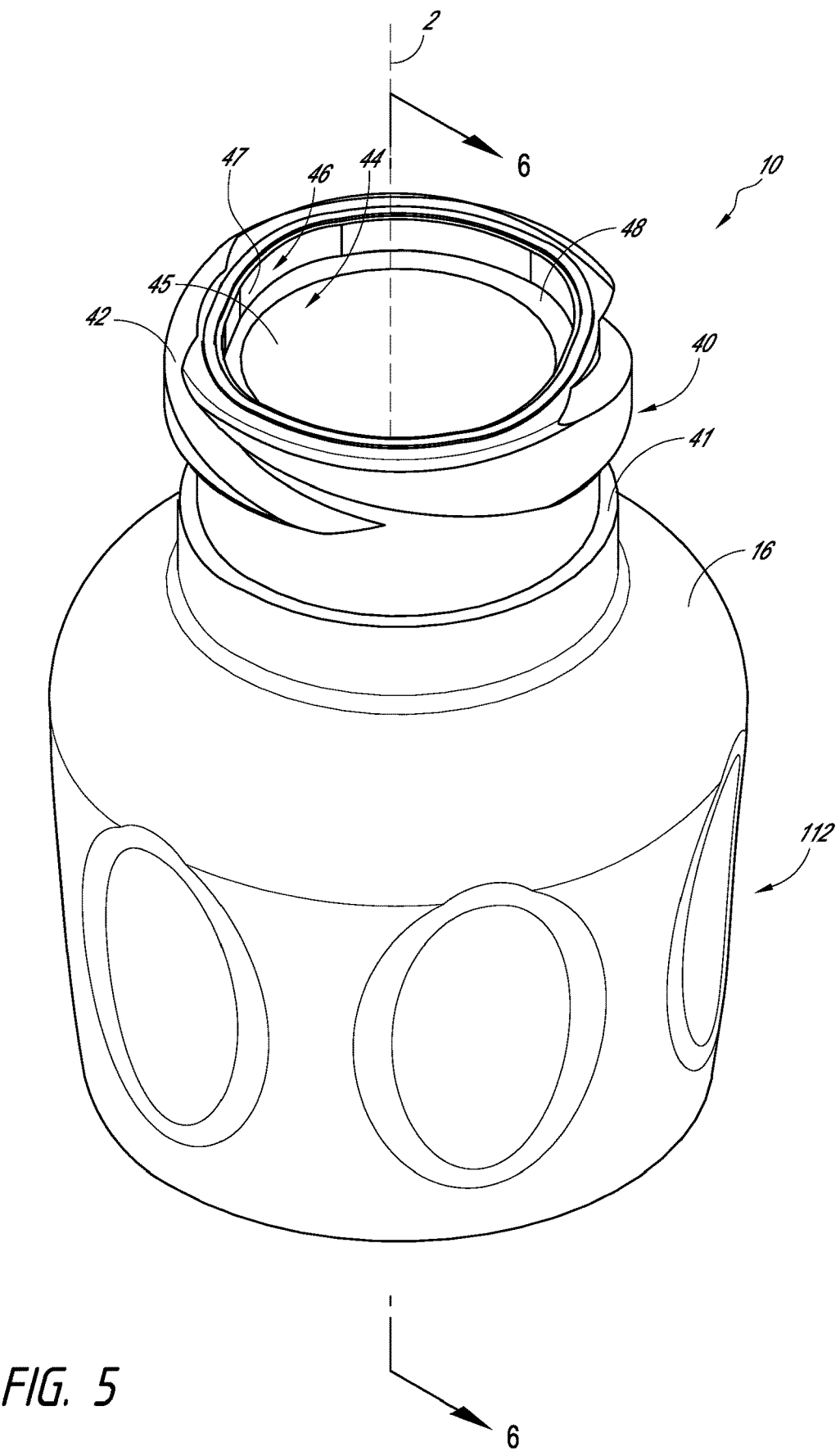
FIG. 5 is a top perspective view of an embodiment of a housing portion.

FIG. 5 illustrates a top perspective view of the first housing 10. In some embodiments, the housing can have a lower section 112 that extends below the shoulder 16 of the housing, which connects to the upper Luer connector region 40. In some embodiments, the upper Luer connector region can have a first section 44 and a second section 46 above the first section. The first section can have an interior surface 45 and the second section can have an interior surface 47. The first section and second section can be joined by a ledge 48. In some embodiments, and as illustrated, the ledge can be flat. In some embodiments the ledge can be angled or can have combinations of flat sections and angled sections. In some embodiments, the first section 44 can have an outer ledge 41.

Figure 6:
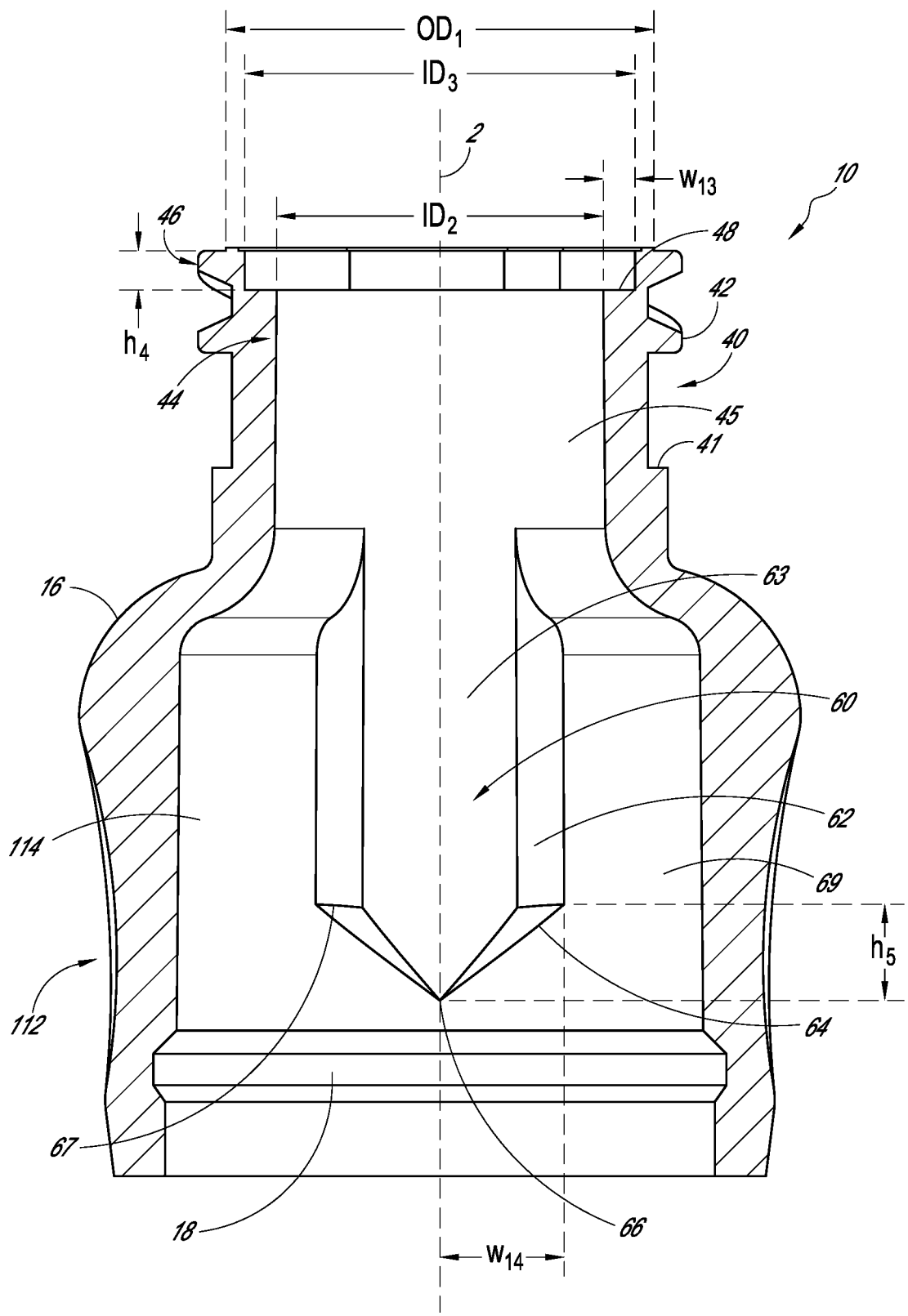
FIG. 6 is a cross-sectional view of the embodiment of FIG. 5.

FIG. 6 illustrates a cross-sectional view of the first housing 10. As illustrated, in some embodiments, the first section 44 and the second section 46 can have the same outer diameter $OD_1$ (without considering the threading 42). However, in some embodiments the first section 44 can have an inner diameter $ID_2$ that is less than the inner diameter $ID_3$ of the second section 46. The difference between these two can help define the ledge 48 and can define its width $w_{13}$.

The ledge 48 can be used to help seat the valve member 30 when the medical connector is fully assembled. The lower surface 54 of the lip 52 of the valve member can engage the ledge 48, positioning the valve member at a desired height relative to the first housing 10 and helping prevent the valve member from passing farther into the first housing. The height $h_4$ of the second section 46 (i.e. the distance from the ledge 48 to an uppermost point of the first housing 10) can be substantially the same as the height $h_1$ of the lip 52 of the valve member 30 prior to the valve member being placed in tension. In some embodiments, however, the height of the second section $h_4$ can be less than or greater than the height $h_1$ of the lip. In some embodiments, the height of the lip 52 is greater than the height $h_4$ of the second section 46 prior to the valve member being placed in tension, but is configured such that when the valve member is in a tensioned state the lip has a height approximately equal to the height of the second section.

In some embodiments the width $w_{13}$ of the ledge 48 can be generally equal to the width $w_3$ of the lip 52 of the valve 30.

In some embodiments, the first housing 10 can have an annular recess 18 on an interior surface. It can also have a downward projection 60 within the interior space 69 of the housing that can be used to help align the first housing 10 with the second housing 20 when the medical connector is assembled. The downward projection can extend from the interior surface 45 of the first section 44 of the housing and into the lower section 112 of the housing. In some embodiments, an interior surface 63 of the downward projection can form a continuous surface with the interior surface 45 of the first section of the housing. In some embodiments, the interior surface 63 of the downward projection can slope inward or outward relative to the interior surface 45 of the first section of the housing.

The downward projection can have side walls 62 that extend downward in a direction substantially parallel to a central longitudinal axis 2 of the housing 10. In some embodiments, the side walls can taper toward each other as they extend downward. The side walls 62 can attach to the interior wall or surface 114 of the lower section 112 of the housing.

At a lower end of the downward projection 60, the projection can have alignment surfaces 64 that angle inward from the side walls 62 toward a bottom edge 66 at a lower tip of the projection. In some embodiments, the edge 66 can be generally perpendicular to the central axis 2. In some embodiments, however, the innermost point of the edge can be above or below the outermost point of the edge, such that the edge is not perpendicular to the central axis. Each alignment surface can join with a respective side wall at a side edge 67. In some embodiments, the side edges can be generally perpendicular to the central axis 2. In some embodiments, the innermost point of one or more of the side edges can be above or below the outermost point of the same edge, such that the edge is not perpendicular to the central axis.

In some embodiments, the alignment surfaces 64 can be helical surfaces (i.e. have a twist between their edges 66 and their corresponding side walls 62) that can help guide the first housing into position with the second housing 20, as discussed further below. The helical nature of the alignment surfaces of the illustrated embodiment is more easily visible in FIG. 7.

With continued reference to FIG. 6, the alignment surfaces 64 are preferably symmetrical about a vertical plane on which the longitudinal axis 2 lies, as illustrated. The alignment surfaces can have a height $h_5$, measured with respect to the outermost point the edge 66 to the outermost point of the side edge 67. The alignment surfaces can also have a width $w_{14}$, measured with respect to the same reference points as the height. The ratio of the height $h_5$ to the width $w_{14}$ can correlate to an angle, or "pitch", of the alignment surfaces. The pitch of the alignment surfaces 64 can also help guide the first housing into position with the second housing, as discussed below.

Figure 7:
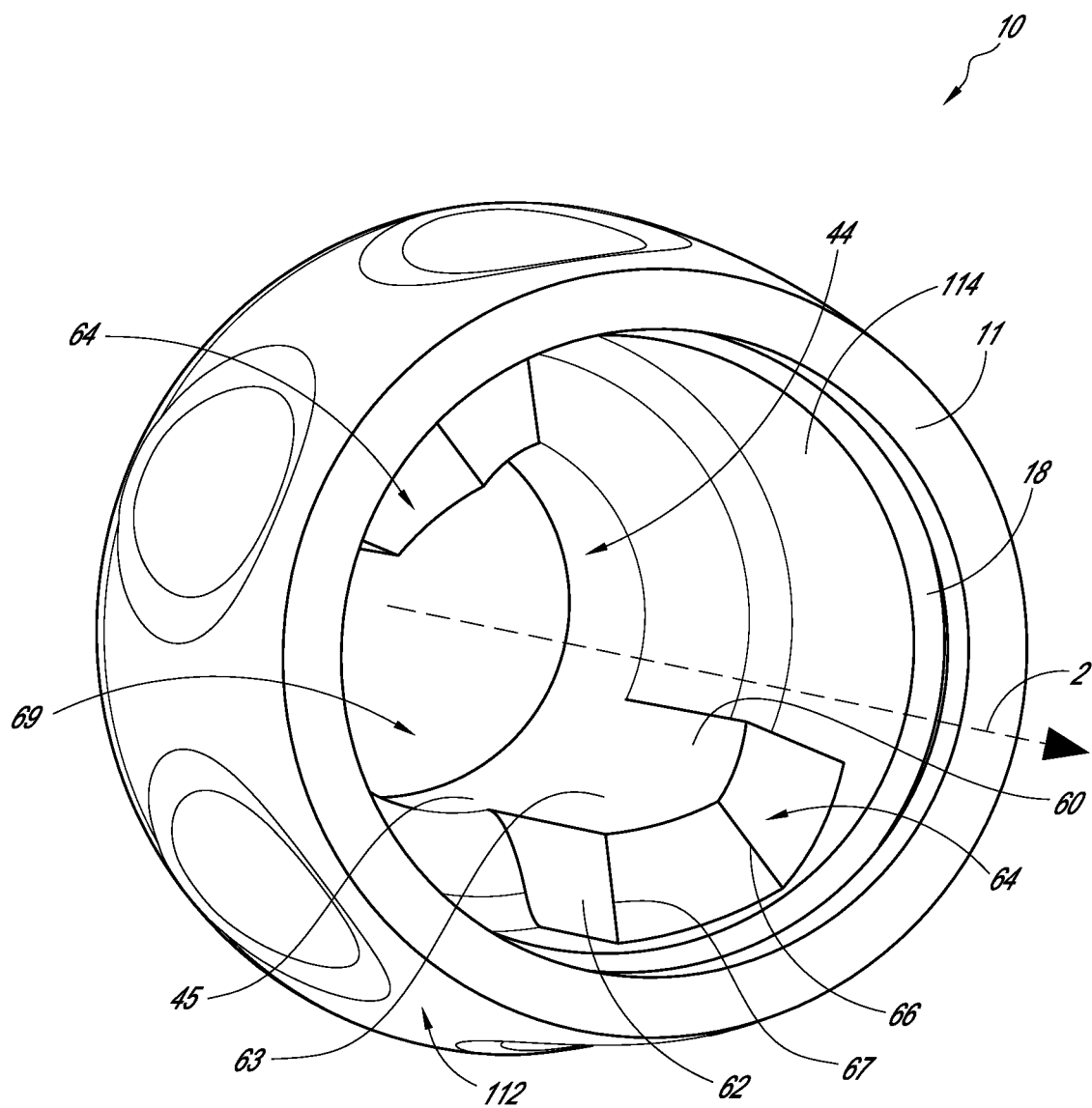
FIG. 7 is a bottom perspective view of the embodiment of FIG. 5.
Figure 8:
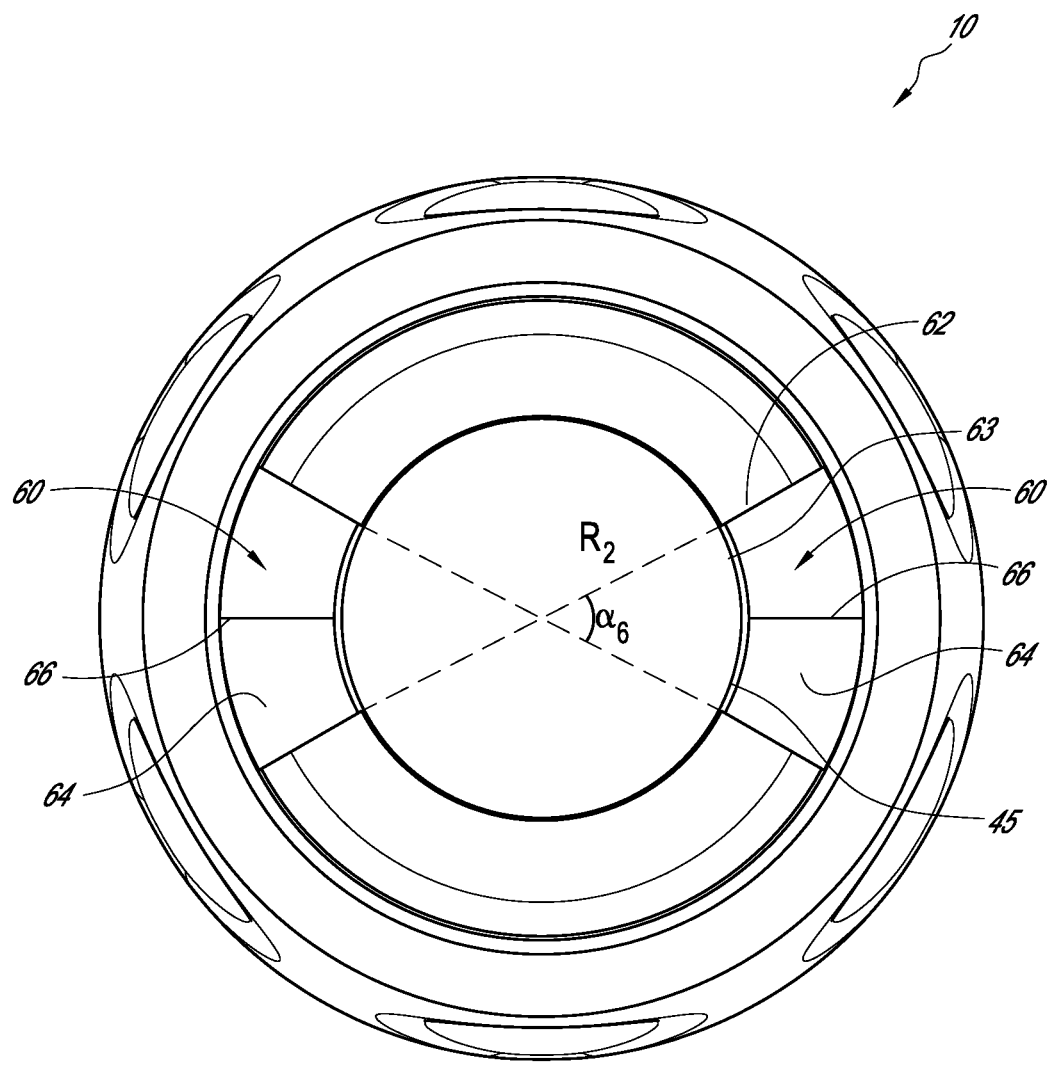
FIG. 8 is a bottom view of the embodiment of FIG. 5.

FIG. 7 illustrates a bottom perspective view of the first housing 10, and FIG. 8 illustrates a bottom view of the housing. The illustrated embodiment has two downward projections 60 positioned on opposite sides of each other within the interior space 69 of the first housing 10. The projections can be thought of as being positioned on a circle centered around the longitudinal axis of the housing 10, and the interior surface 63 of each projection can have a radius $R_2$. The downward projections can also have an angular width $\alpha_6$ that bounds either side of the interior surface of each projection. Preferably, as illustrated, the side walls 62 of each projection each lie on a plane and are oriented such that the intersection of the side wall planes forms the same angle $\alpha_6$. In some embodiments, however, the side wall planes can form angles that are greater than or less than the angle $\alpha_6$ of the interior surface 63 of the projection.

In some embodiments, the first housing can have only one downward projection, and in some embodiments, it can have more than two downward projections. When the first housing has more than one downward projection, they can be symmetrically spaced around the longitudinal axis 2 of the first housing, as the two projections illustrated in FIG. 8 are. As discussed further below, this symmetrical spacing can make proper alignment and assembly of the medical connector easier. In some embodiments, including two downward projections facilitates the connection between a first housing 10 and second housing 20 in a particular rotational arrangement relative to each other.

Second Housing

Figure 9A:
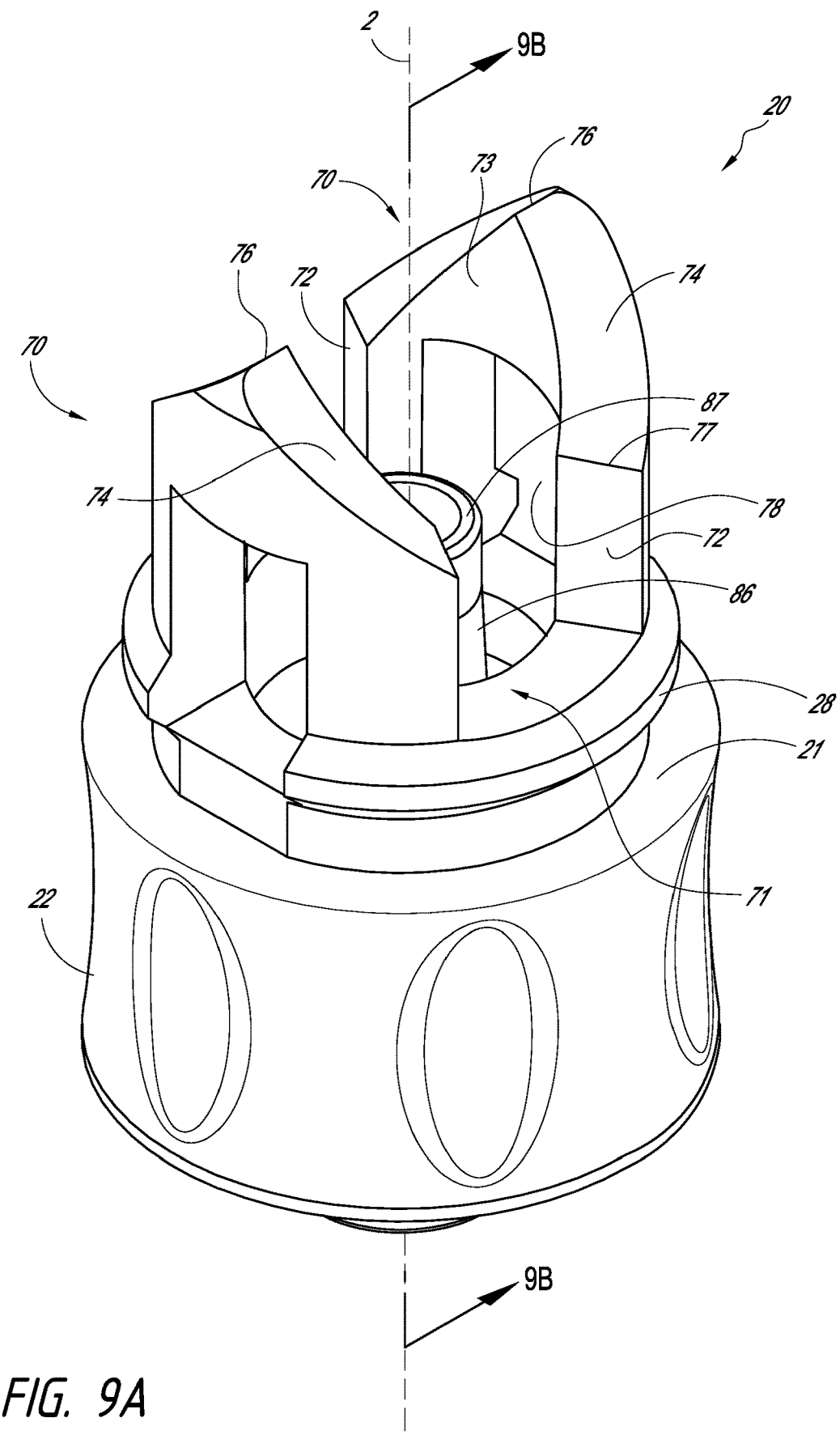
FIG. 9A is a perspective view of an embodiment of a housing portion.

FIG. 9A illustrates a top perspective view of the second housing 20. The second housing can have one or more upward projections 70. Like the downward projections 60 of the first housing 10, the upward projections 70 can be thought of as being positioned on a circle centered about a central longitudinal axis of the second housing 20, and the interior surface 73 of each projection can have a radius $R_3$ (visible in FIG. 10). In the illustrated embodiment, there are two upward projections. In some embodiments, the two projections can be on opposite sides of the circle. In some embodiments, the second housing can have fewer or more than two upward projections. As with the first housing, when the second housing has multiple projections they can be symmetrically positioned around the central longitudinal axis 2.

In some embodiments, the number of upward projections can correspond to the number of downward projections 60 in the first housing 10. Like the downward projections, each upward projection 70 can have two side walls 72 that extend upward in a direction substantially parallel to the central longitudinal axis of the second housing 20. In embodiments where the side walls 62 of the downward projections 60 taper toward each other, discussed above, the side walls 72 of the upward projections 70 can taper toward each other at the same angle.

Each upward projection can also have two alignment surfaces 74 that angle from the side walls toward an upper edge 76 at an upper tip of each projection. The alignment surface 74 and side walls 72 can join at side edges 77. Like the downward projections 60, in some embodiments, the upper edge 76 can be generally perpendicular to the central axis 2. In some embodiments, however, the innermost point of the edge can be above or below the outermost point of the edge, such that the edge is not perpendicular to the central axis. Similarly, in some embodiments the side edges 77 can be generally perpendicular to the central axis 2. In some embodiments, the innermost point of one or more of the side edges can be above or below the outermost point of the same edge, such that the edge is not perpendicular to the central axis. In some embodiments, the upward projections 70 can include a curved surface 81 configured to direct and center the first housing 10 as it is coupled to the second housing 20.

Also like the downward projections 60, in some embodiments the alignment surfaces 74 can be helical. Preferably, the alignment surfaces 74 have the same shape as the alignment surfaces 64 of the downward projections, such that opposing sets of helical alignment surfaces 64, 74 can be pressed flush against each other. The helical nature of the surfaces can help promote rotation of the first and second housings relative to each other while the alignment surfaces are in contact with each other.

In some embodiments, each upward projection can also have an opening 78 cut out of it. The opening can interact with the shoulders 34 of the valve member 30, as discussed in more detail below.

Figure 9B:
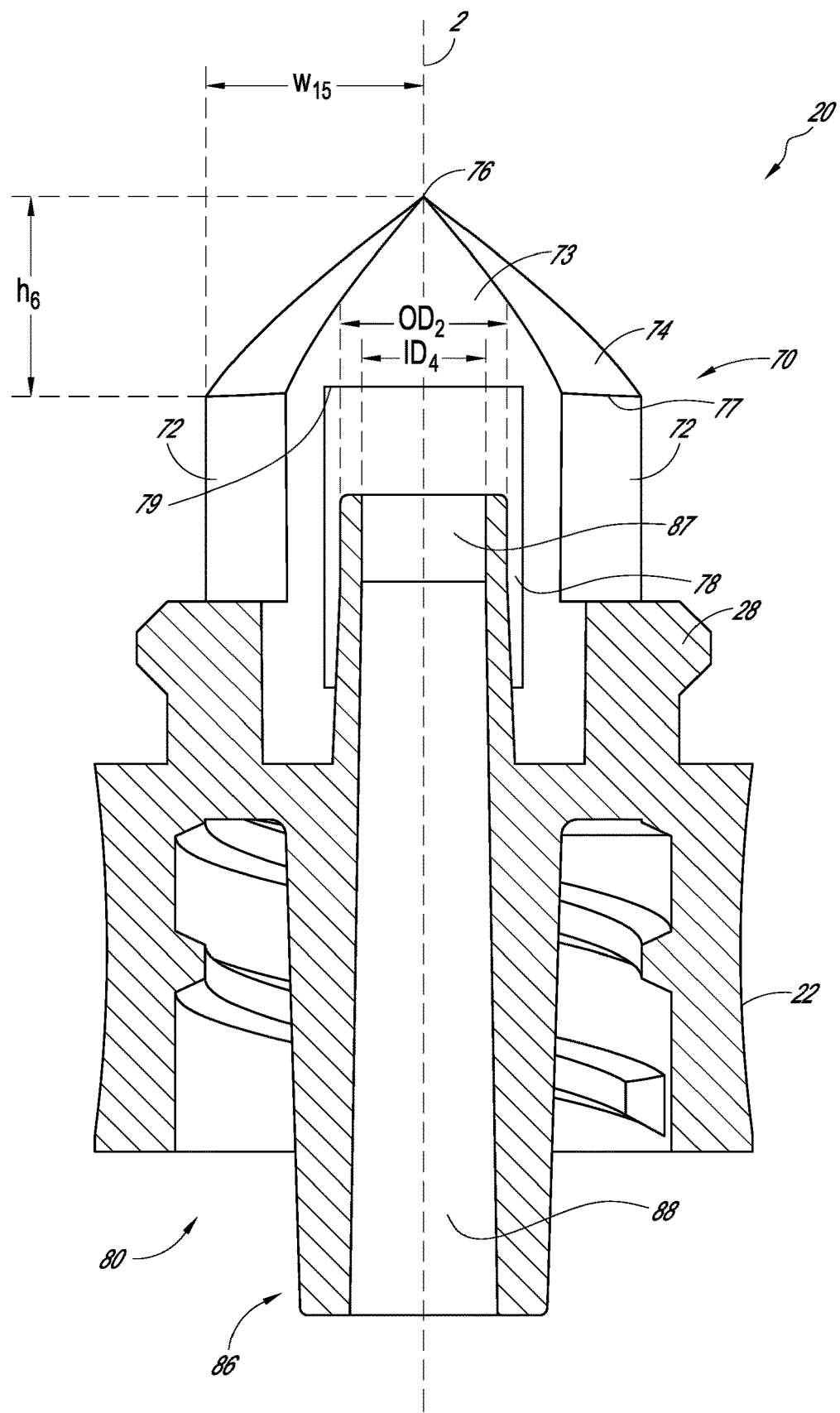
FIG. 9B is a cross-sectional view of the embodiment of FIG. 9A.

FIG. 9B illustrates a cross-sectional view of the second housing 20. As illustrated and similar to the downward projections 60, in some embodiments the alignment surfaces 74 of an upward projection are symmetrical about a vertical plane on which the longitudinal axis 2 lies. Also like the downward projections, the alignment surfaces can have a height $h_6$, measured with respect to the outermost point of the upper edge 76 to the outermost point of the side edge 77. The alignment surfaces can also have a width $w_{15}$, measured with respect to the same reference points as the height $h_6$. The ratio of the height $h_6$ to the width $w_{15}$ can correlate to an angle, or "pitch", of the alignment surfaces 74.

In some embodiments, the pitch of the alignment surfaces 74 of an upward projection 70 can be generally the same as the pitch of the alignment surfaces 64 of the downward projections 60. In some embodiments, their pitches can vary. Preferably, the pitch of the alignment surfaces of the upward and downward projections is steep enough such that the first housing 10 and the second housing 20 do not bind when they are pushed together and their respective alignment surfaces contact each other. Preferably, the pitch of the alignment surfaces is shallow enough such that a sufficient "twist" of the alignment surfaces to promote rotation between the first and second housing can be in place. In some embodiments, the ratio of the height $h_6$ to the width $w_{15}$ of the alignment surfaces 74 of the upward projections 70, and the ratio of the height $h_5$ to the width $w_{14}$ of the alignment surfaces 64 of the downward projections 60 (visible in FIG. 6), can be greater than or equal to about 0.5 and/or less than or equal to about 1.5. In some embodiments, this ratio can be greater than or equal to about 0.25 and/or less than or equal to about 2.

FIG. 9B also illustrates the Luer cannula 86 of the lower housing 20. In some embodiments, the Luer cannula 86 can have an upper section 87 and a lower section 88. In some embodiments, the upper and lower sections can be distinguished by their cross sectional profiles, specifically with regard to their inner diameters. For example, in the illustrated embodiment the lower section 88 can have a profile that tapers from the bottom of the cannula 86 to the upper section 87. In other words, the inner diameter (and the corresponding cross sectional area) can decrease from the lower end of the cannula to the upper section. As illustrated, this decrease is linear, but in some embodiments it can be nonlinear. In some embodiments, in contrast, the upper section 87 can have vertical interior walls, such that the inner diameter $ID_4$ of the upper section 87 is generally constant. In some embodiments, the outer diameter $OD_2$ of the upper section 87 can be generally constant as well. In some embodiments, the outer diameter of the upper section can vary, even if the inner diameter is generally constant.

In various embodiments the upper section 87 and lower section 88 of the Luer cannula 86 can occupy different proportions of the Luer cannula. For example, in some embodiments where the upper section has vertical interior walls, the upper section can occupy at least five percent of the length of the Luer cannula. In some embodiments, the upper section can occupy at least ten, twenty, at least thirty, at least forty, or at least fifty percent of the Luer cannula. In some embodiments, the upper section with a constant inner diameter $ID_4$ can be greater than or equal to about 5 percent and/or less than or equal to about 15 percent of the total length of the Luer cannula. In some embodiments, the upper section can be can be greater than or equal to about 10 percent and/or less than or equal to about 30 percent of the total length of the Luer cannula.

Similarly, in some embodiments where the upper section has vertical interior walls, the ratio of the upper section to the lower section can be at least approximately 1:20, at least approximately 1:10, at least approximately 1:5, at least approximately 1:4, at least approximately 1:2, or at least approximately 1:1. In some embodiments, the ratio of the upper section to lower section can be approximately 1:8.5. In some embodiments, the ratio of the upper section to the lower section can be greater than or equal to about 1:20 and/or less than or equal to about 1:5. In some embodiments, the ratio of the upper section to the lower section can be greater than or equal to about 1:10 and/or less than or equal to about 1:4.

FIG. 9B also illustrates an upper surface or upper boundary 79 of an opening 78 of an upward projection 70. In some embodiments, the upper boundary 79 can be approximately level with the side edge 77. In some embodiments, the upper boundary 79 can be below or above the side edge. Further, in some embodiments the very top of the upper section 87 of the Luer cannula 86 may extend to a position short of the upper boundary 79. In some embodiments, it can be approximately level with the upper boundary or extend above the upper boundary.

Figure 10:
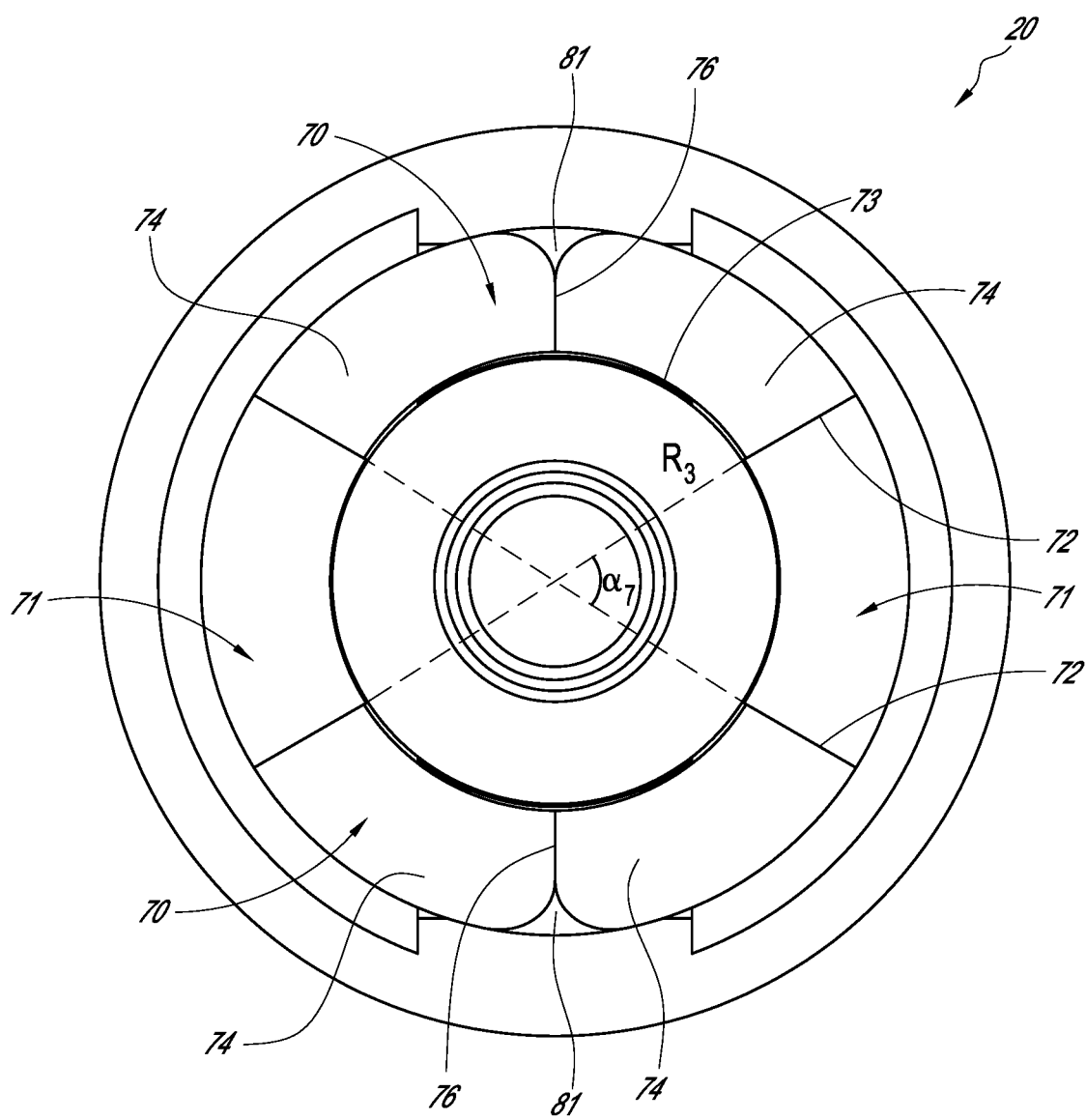
FIG. 10 is a top view of the embodiment of FIG. 9A.

FIG. 10 illustrates a top view of the second housing 20. As illustrated in FIG. 10, the upward projections 70 in the second housing 20 can form two gaps 71 between them. The gaps can have an angular width $\alpha_7$ defined as the angle bounding the gap (i.e. the angle that bounds adjacent sides of the interior surfaces 73 of adjacent projections). Preferably, as illustrated, the side walls 72 of each projection each lie on a plane and are oriented such that the intersection of adjacent side wall planes of adjacent projections forms the same angle $\alpha_7$ as that of the gaps. In some embodiments, however, the side wall planes can form angles that are greater than or less than the angle $\alpha_7$ that bounds a gap. In some such embodiments, the planes of the side walls 62 of the downward projections 60 can form angles that correspond with the angles formed by the planes of the side walls 72 of the upward projections 60. In embodiments where there is a single upward projection 70, the gap 71 can be defined as the angular width between opposite side walls 72 of the same single projection.

The angular width $\alpha_7$ of the gap 71 can be substantially the same or slightly wider than the angular width $\alpha_6$ of the downward projection 60 of the first housing 10. In some embodiments, this can mean that the sum of the angular width $\alpha_7$ of the gap 71 and the angular width $\alpha_6$ of the downward projection 60 of the first housing is approximately 180 degrees. In some embodiments, the radius $R_2$ of the inner surface 63 of the downward projections 60 can be substantially the same as the radius $R_3$ of the inner surface 73 of the upward projections 70. These relationships can help to ensure proper alignment of the first housing 10 and second housing 20 when the medical connector is assembled, with regard to positioning the housings 10, 20 such that their respective central longitudinal axes coincide, and also with regard to rotational alignment.

Rotational alignment can be assured in part because if the first housing 10 is misaligned when it is placed onto the second housing 20, the interaction between alignment surfaces 64 of the downward projections 60 and alignment surfaces 74 of the upward projections 70 will tend to twist the housings relative to each other until the downward projection 60 slides into the gap 71. The matched helical nature of the alignment surfaces can allow for a smoother rotation that requires less force and creates less stress within the components.

When a downward projection 60 is properly located within a gap 71, the side walls 62 of the downward projection 60 will preferably be adjacent side walls 72 of one or more upward projections 70, preventing rotation of the housings relative to each other. In the illustrated embodiment, the first housing 10 can fit within the second housing 20 in one of two positions, a first position and a second position in which the first housing is rotated 180° relative to the first position. The number of available positions can depend on the number of projections. For example, in embodiments where there are three upward projections and three downward projections, the housings could fit together in one of three different positions.

The fit between the projections 60, 70 also ensures alignment of the longitudinal axes of each housing because in both the first position and second position (or other positions where the housings have more than two projections) the central axes of each housing are aligned. There can be no other positions in which the first housing 10 and second housing 20 can fit together. Additionally, because the valve member 30 can be attached to the first housing 10 from the mold as it is formed, proper alignment of the valve member within the housings can be assured.

With reference to FIG. 9A, proper alignment of the valve member 30 when the medical connector is fully assembled can help ensure that the shoulders 34 of the valve member 30 can fit within the recesses or openings 78 of the second housing 20. This can help keep the valve member in tension, as discussed in more detail below. Once the alignment surfaces have positioned the first and second housing in proper orientation with respect to each other, the housings can be pushed together until the annular projection 28 snaps into the annular recess 18 in the first housing 10. In some embodiments, the annular recess is positioned on the second housing 20 and a corresponding annular projection is included on the first housing 10, such recess and projection cooperating together like recess 18 and projection 28 to inhibit axial movement between the housings 10,20.

In some embodiments, the first housing and the second housing can have multiple stable positions relative to each other, as described in greater detail below.

Assemblies

Figure 11A:
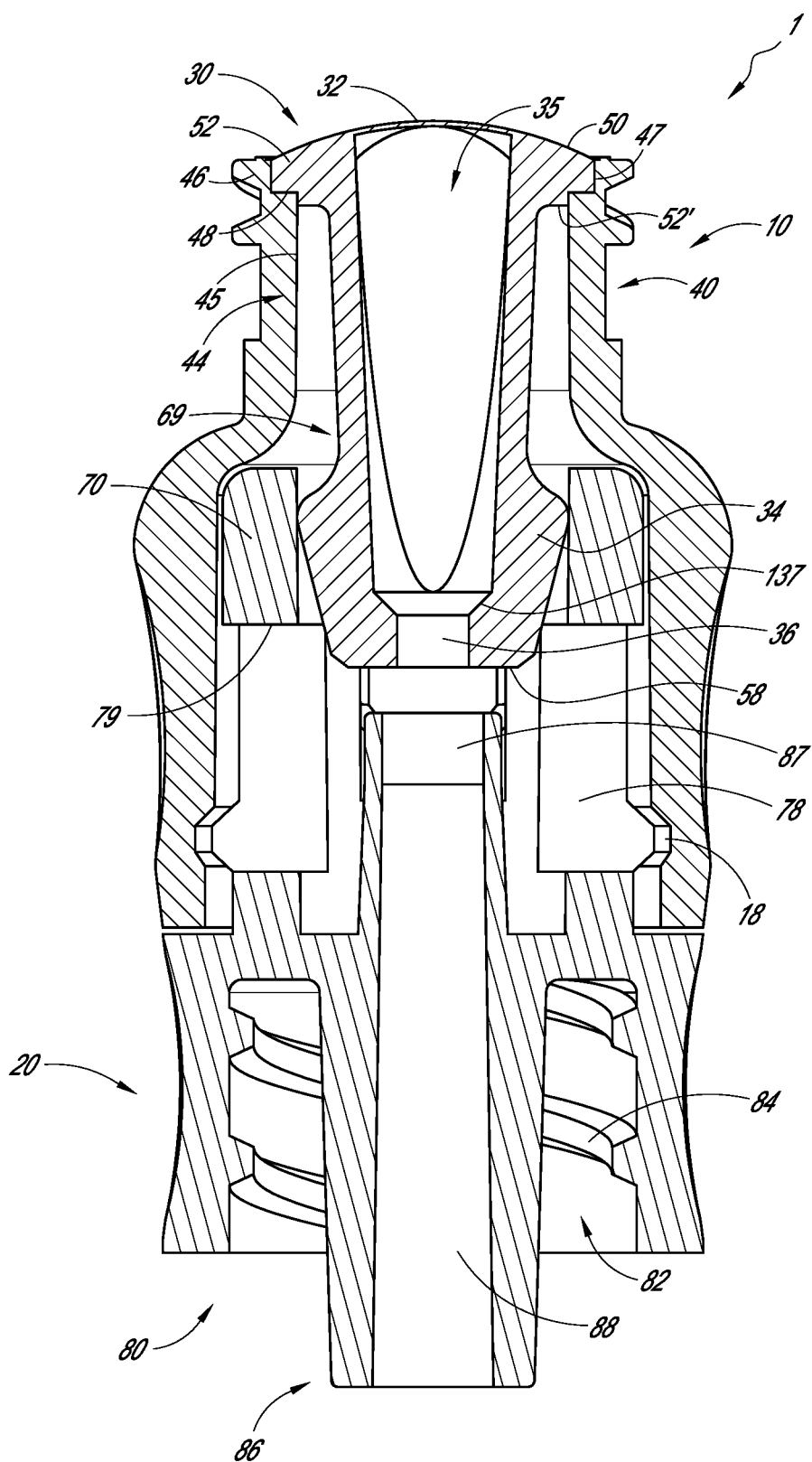
FIG. 11A is a cross-sectional view of an embodiment of a medical connector prior to complete assembly.
Figure 11B:
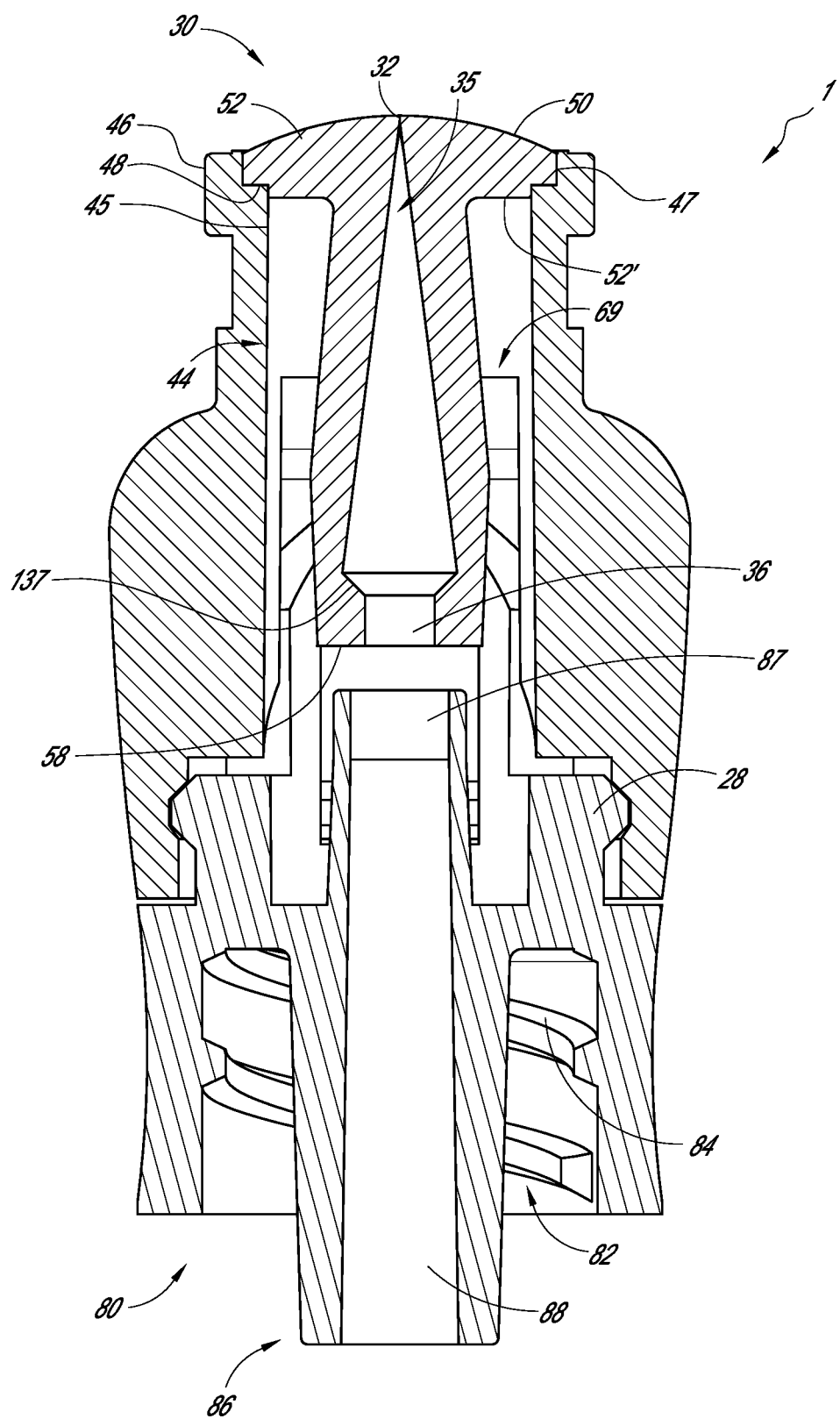
FIG. 11B is a cross-sectional view of a medical connector taken at about 90 degrees relative to the cross-section of FIG. 11A.

FIGS. 11A and 11B illustrate the first housing 10, the second housing 20, and the valve member 30 during a first stage of the assembly process when manufacturing the connectors. In a second stage of the assembly process, the valve can be stretched toward the cannula 86 and positioned around at least a portion of the cannula, as discussed below.

FIG. 11A is a cross-sectional view of the medical connector 1 and FIG. 11B is a cross-sectional view of the connector at approximately 90° from the view of FIG. 11A. As illustrated in FIG. 11A, the valve member 30 can be molded into the first housing 10 in an orientation such that the shoulders 34 are in alignment with the upward projections 70 of the second housing 10 once the first and second housings are placed together. Because the valve member 30 is formed of a flexible material, as discussed above, the shoulders 34 can compress inward from the pressure of contact with the upward projections 70, allowing the valve member 30 to fit between the upward projections.

In some embodiments, the valve member 30 and the first housing 10 can be molded together as part of a two-shot injection mold. In some embodiments, the valve can be molded around a core pin (not illustrated) that can define the internal cavity 35 and the lead lumen 36. A first sleeve (not shown) positioned around the core pin can define at least some of the outer surfaces of the valve. In some embodiments, the core pin can extend above the first sleeve and the top of first sleeve can extend to a position below the second section 46 of the Luer connector region 40. This can allow the material that forms the valve to flow into direct contact with the interior wall 47 of the second section, forming the lip 52. In some embodiments, the material that forms the valve can also flow into direct contact with the interior wall 45 of the first section 44 of the Luer connector region 40, forming the lower lip 52'. Further, in some embodiments the molding process can be configured to allow the material that forms the valve to flow above the second section 46, such that the height $h_1$ of the lip 52 (illustrated in FIGS. 4A and 4B) is greater than the height $h_4$ of the second section 46 (illustrated in FIG. 6). In some embodiments, the molding process can be configured to allow the material that forms the valve to flow above the second section 46, but only enough to form a dome on the top surface 50 of the valve while keeping the height $h_1$ of the lip 52 generally equal to the height $h_4$ of the second section 46. FIGS. 11A and 11B illustrate a valve member 30 and first housing 10 molded in this manner. The description provided with respect to FIGS. 33A-35B provides more details of various embodiments of a molding process and molding assembly.

Figure 12A:
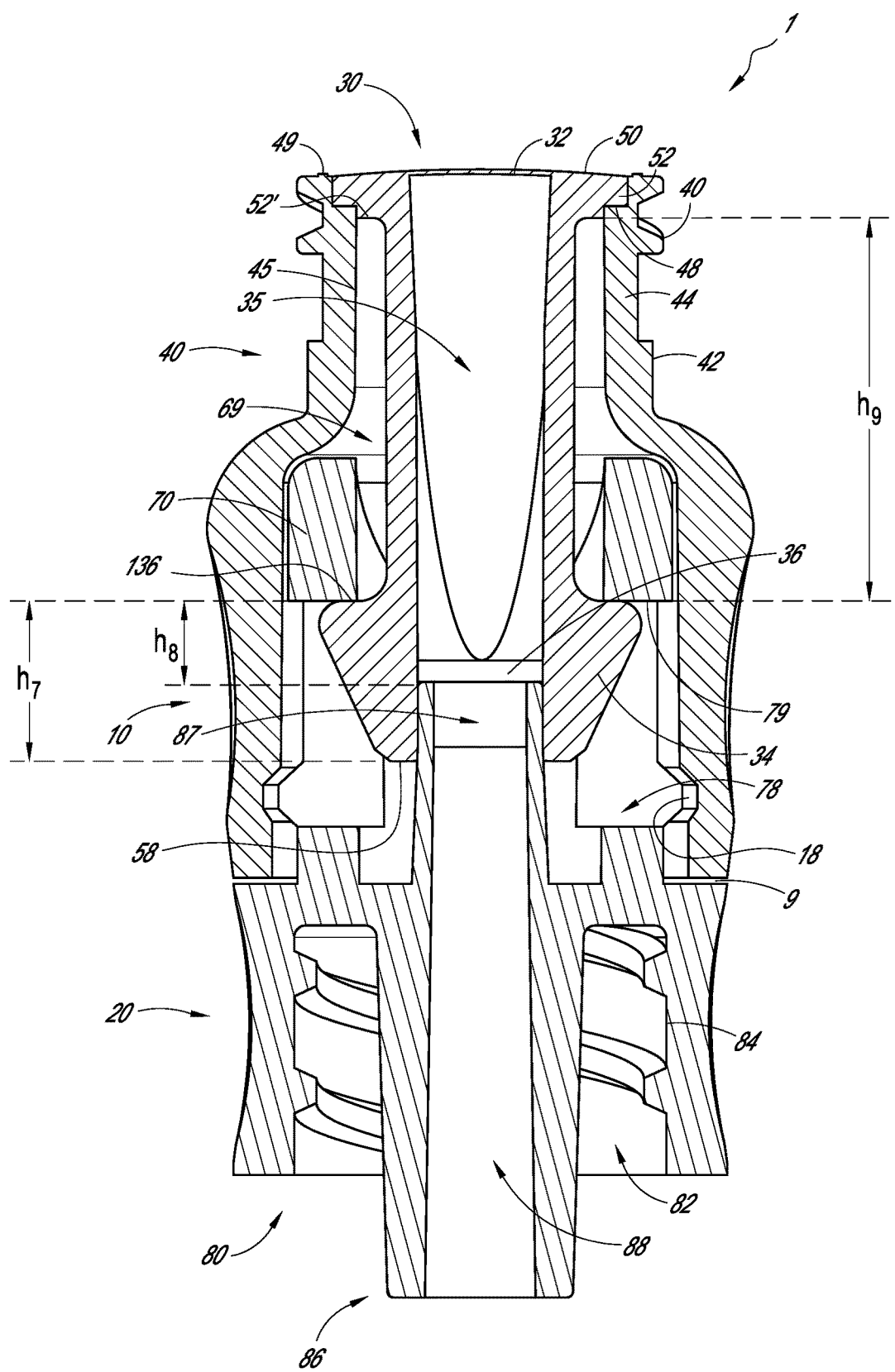
FIG. 12A is a cross-sectional view of an embodiment of a medical connector fully assembled.
Figure 12B:
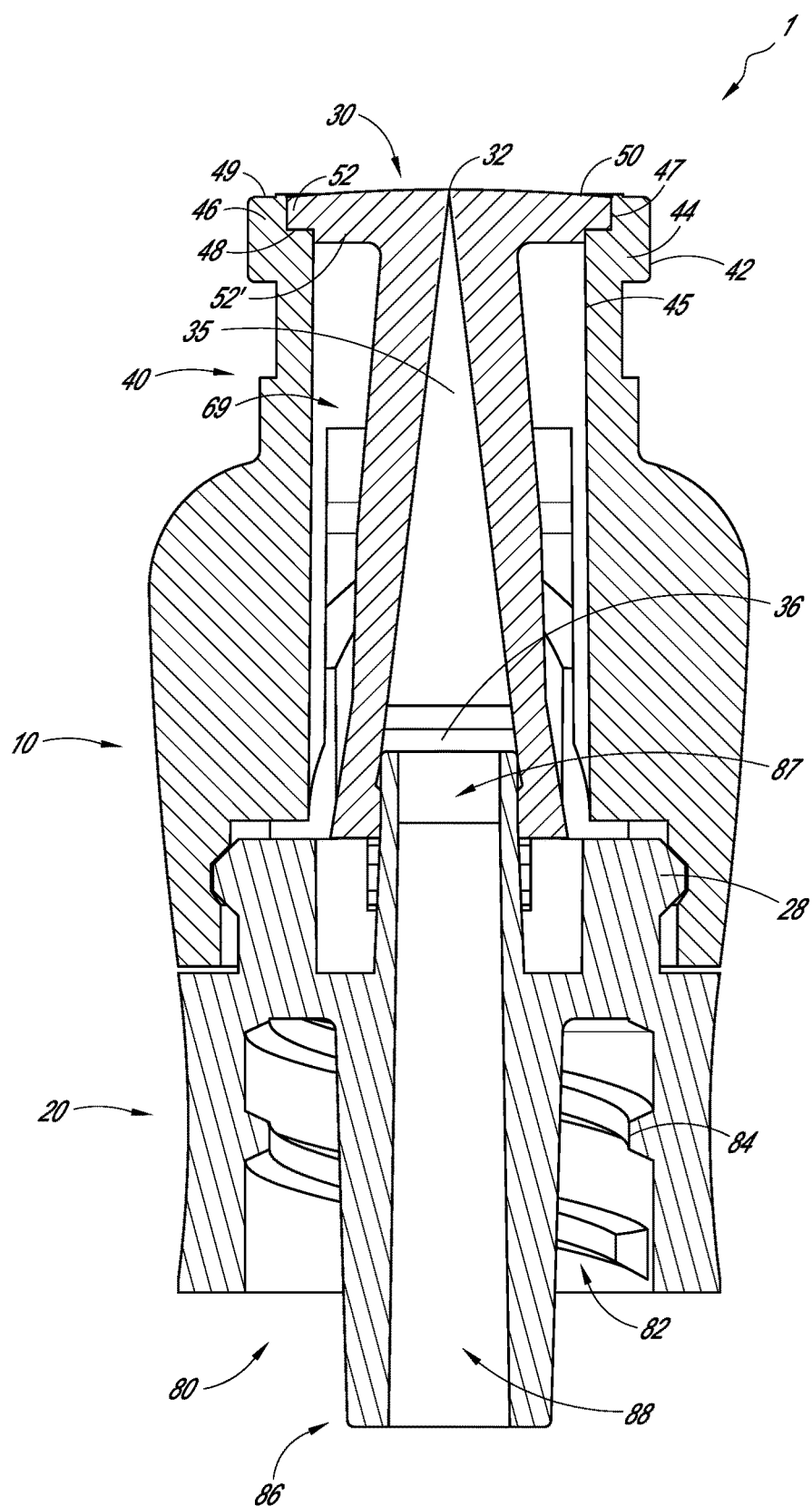
FIG. 12B is a cross-sectional view of a medical connector taken at about 90 degrees relative to the cross-section of FIG. 12A.

The valve member can also be formed with a height such that the lead lumen 36 of the valve member does not reach the cannula 86 when the first housing 10 and second housing 20 have first been joined together. The valve member at this point is in a generally relaxed, first state. Also visible in FIGS. 11A and 11B is a gap between the valve member 30 and the cannula 86 when the first housing and the second housing 20 are first placed together. When the connector is fully assembled and in a second stage of the assembly process, the valve member can be stretched downward and the lead lumen 36 can surround a portion of the cannula 86. This is a second state of the valve member, one embodiment of which is illustrated in FIGS. 12A and 12B.

With continued reference to FIGS. 11A and 11B, in some embodiments an inner diameter $ID_1$ of the lead lumen 36 (visible in FIGS. 4A and 4B) can be less than an outer diameter $OD_2$ of the upper section 87 of the cannula 86 (visible in FIG. 9B). Thus, in some embodiments, for the lead lumen to fit around the cannula it must be stretched. The ratio between the inner diameter of the lead lumen $ID_1$ and the outer diameter of the upper section $OD_2$ can depend on the particular physical properties of the material used to construct the valve member 30. Desirably, the ratio is such that the valve member 30 and lead lumen 36 will maintain a tight fit around the cannula that does not allow fluid to escape, but that also does not impose an amount of stress on the valve member such that it unexpectedly breaks down, tears, or otherwise fails to function as desired.

The ratio between the inner diameter $ID_1$ of the lead lumen and the outer diameter $OD_2$ of the upper section of the cannula 86 can also depend on the desired tension within the valve member. The greater the tension in the valve member, the lower the ratio will need to be in order to maintain a fit tight enough for the lead lumen 36 to remain in place around the cannula 86. In some embodiments, the ratio can be greater than or equal to about 0.4 and/or less than or equal to about 0.8. In some embodiments, the ratio can be greater than or equal to about 0.5 and/or less than or equal to about 0.9.

Similarly, the ratio between the inner diameter $ID_1$ of the lead lumen 36 and the bottom width $w_5$ in the plane of FIG. 11A (both measurements visible in FIG. 4A) can be modified to, among other things, control the tightness of the seal between the cannula 86 and the lead lumen 36. In some embodiments, this ratio $ID_1/w_5$ can be greater than or equal to approximately 1 and/or less than or equal to approximately 2. In some embodiments, the ratio can be greater than or equal to about 0.5 and/or less than or equal to about 3. The ratio between the inner diameter $ID_1$ of the lead lumen 36 and the bottom width $w_{10}$ in the plane of FIG. 11B (both measurements visible in FIG. 4B) can be similarly modified. In some embodiments, this ratio $ID_1/w_{10}$ can be greater than or equal to approximately 1 and/or less than or equal to approximately 2. In some embodiments, it can be greater than or equal to about 0.5 and/or less than or equal to about 3.

Continuing with respect to FIG. 11A, and as described with respect to FIG. 9B, in some embodiments the very top of the upper section 87 of the cannula 86 can vary in position relative to the upper opening boundary 79. These various positions can affect how much of the cannula will be surrounded by the lead lumen 36 (and in some embodiments portions of the internal cavity 35) when the valve member 30 is in the second state.

FIGS. 12A and 12B illustrate the medical connector 1 once it has been fully assembled and the lead lumen 36 has been stretched around the cannula 86. FIG. 12A illustrates the same cross-sectional angle as FIG. 11A, and FIG. 12B illustrates the same cross-sectional angle as FIG. 11B.

To position a valve member 30 around the cannula 86, an insertion device or cannula (not shown) can be inserted through the slit 32 of the valve member and into the internal cavity 35. In some embodiments, the insertion device can be a generally hollow cannula configured similar to a standard male luer. In some embodiments, the insertion device is solid at the end that is directed into the valve member 30 to position it. In some embodiments, the insertion device can be hollow and can have an inner diameter at its lower tip that is at least slightly larger than the outer diameter $OD_2$ of the upper section 87 of the cannula 86. The insertion device can be inserted into the internal cavity 35 and pushed downward until it reaches the lead lumen 36. In some embodiments, the insertion device can have stretched the valve member 30 downward from the first state, placing the valve in tension or increasing the tension in the valve when the insertion device has reached the lead lumen 36. In other embodiments, the slit profile is wide enough to permit the insertion device to reach the lead lumen without putting the valve in tension or increasing the tension in the valve.

In embodiments in which the insertion device has a generally hollow end, the insertion device can be inserted to extend into the lead lumen until the lead lumen surrounds the insertion device and the insertion device is positioned around a portion of the cannula 86 of the second housing 20. In some embodiments, the internal cavity 35 can include a tapered portion 137 (visible in FIG. 11A). The tapered portion can make it easier for the insertion device to enter and expand the lead lumen as the insertion device is moved into the valve member 30.

As the valve member 30 is stretched toward the cannula 86, the shoulders 34 can move down as well. The valve member can be pushed at least far enough down such that the top surface 136 of the shoulders 34 reach the openings 78. The valve had been compressed with the shoulder against the surface of the upward projections 70, but because the valve member 30 is formed of a flexible material the valve and shoulders can expand back outward when they reach the openings, snapping into the available space.

At this point, the valve member 30 is preferably positioned around the insertion device, which in some embodiments can also be positioned around the cannula 86 of the connecting device. The insertion device can then be withdrawn, and the stretched lead lumen 36 can be prevented from being withdrawn with the insertion device by the interaction between the shoulders 34 and the upper opening boundary 79, which will place a downward force on the shoulders 34. The valve member will preferably remain in this second state.

In some embodiments, an insertion device does not need to extend all the way to or be positioned around the cannula 86. In some embodiments the insertion can be sized such that as it is inserted into the valve member 30, it contacts a wall of the internal cavity 35 of the valve member. Friction against the wall of the valve member can be sufficient to push the valve member down as the insertion device is inserted further. The bottom 58 of the valve member can contact the upper section 87 of the cannula 86, compressing the valve member and causing the lead lumen 36 to widen. The friction between the wall of the interior cavity of the valve member and the insertion device can be sufficient to compress the bottom of the valve member until the lead lumen becomes wide enough and move around the upper section of the cannula 86. As the insertion device is inserted further, the lead lumen can slide further down the cannula until the shoulders 34 move into position within the openings. This can be accomplished without the insertion device reaching the luer cannula 86. When the shoulders are into position within the openings, the insertion device can be withdrawn.

When the insertion device is withdrawn, the lead lumen 36 can remain around at least a portion of the cannula 86, naturally returning toward its original width and forming a tight fit. Once the valve member has been positioned around the cannula 86, a substantially straight fluid flow path exists in the medical connector 1 that runs from the top 50 of the valve member, through the internal cavity 35, into the cannula 86, and out the cannula 86 and out of the medical connector.

The length of the cannula 86 that remains surrounded by the valve member 30 can be the difference between the height $h_7$ of the shoulder 34 as deformed in the second state (i.e. the distance from the top surface 136 of the shoulders 34 to the bottom 58 of the valve member 30) and the distance $h_8$ from the top of the cannula 86 to the upper opening boundary 79. In embodiments where the cannula extends above the upper opening boundary, the portion of the cannula that remains surrounded by the valve member can be the sum of these distances $h_7$, $h_8$. In some embodiments, as illustrated, the valve member can remain positioned around the upper section 87 of cannula 86 and a portion of the lower section 88. In some embodiments, the valve member remains positioned around just a portion of the upper section 87.

Because the location of the upper opening boundary 79 can help determine the second state of the valve member, the upper opening boundary can be positioned according to a desired tension. More specifically, it can be useful to refer to a ratio of two distances: the distance $h_9$ from the lower lip 52' of the first housing 10 to the upper opening boundary 79 (or the top surface 136 of the shoulders 34 when the valve member is in the second state as illustrated), and the distance $h_{10}$ (visible in FIG. 4A) from the bottom surface 54' of the lower lip 52' to the top surface 136 of the shoulders 34 when the valve member is in the first state. The ratio is generally greater than or equal to about 1.5 and/or less than or equal to about 2.5. In some embodiments, the ratio can be greater than or equal to about 1.25 and/or less than or equal to about 3. This ratio can affect the amount that the valve stretches when in the second state.

In various embodiments, it can also be useful to refer to changes in height of the valve member between the first state and the second state. In some embodiments, the height of the valve member can be defined from the bottom 58 of the valve member to a lower lip 52' of the valve member. Thus, a height of the valve member in the second state can be defined as the sum of the heights $h_7$ and $h_9$, while a height of the valve member in the first state can be defined as the sum of the heights $h_{10}$ and $h_3$ (illustrated in FIG. 4A). In some embodiments, the height of the valve member can be defined as the height from the bottom 58 of the valve member to any preferred location on the top surface 50 of the valve member, such as the uppermost point of the top surface or the location of the top surface immediately adjacent an upper surface 49 of the Luer connector region 40. In some embodiments, the ratio of the height of the valve member in the second state to the height in the first state can be greater than or equal to about 1.0 and/or less than or equal to about 1.8. In some embodiments, the ratio can be greater than or equal to about 1.1 and/or less than or equal to about 1.3.

When the valve 30 is placed or increased in tension it can be braced near its top by the ledge 48, which can provide a reaction force against the lip 52. In some embodiments, the valve can be further supported by the outer surface of the lip 52 contacting the interior wall 47 of the second section 46 of the first housing 10, and/or the outer surface of the lower lip 52' contacting the interior wall 45 of the first section 44 of the first housing.

The tension within the valve member can produce a number of effects. One such effect is that the top 50 of the valve member can tend to be pulled downward toward the Luer connector region 40. Although the seating of the valve member within the Luer connector region, as discussed above, can support the valve member as the insertion device stretches it downward, the portions of the top of the valve member that are more centrally located may flex down and into the housing. It is for this reason that the valve member 30 can have a domed top surface 50 when the valve member is in its first state, as illustrated in FIGS. 11A and 11B. When the valve member is in the second state and the top 50 is pulled downward, the dome can flatten out. In some embodiments, the valve and housings can be configured according to combinations of the ratios discussed above such that the valve in its second state has a flat top surface 50. This can make it easier to swab the surface and prevent accrual of bacteria or other elements that can increase the risk of infection.

Another result of the tension within the valve member 30 is that the top 50 of the valve member can experience compression in a plane perpendicular to the vertical stretching of the valve member. This compression can keep the slit 32 more tightly closed at the top surface 50 of the valve, generating a tighter seal for the connector.

Figure 13A:
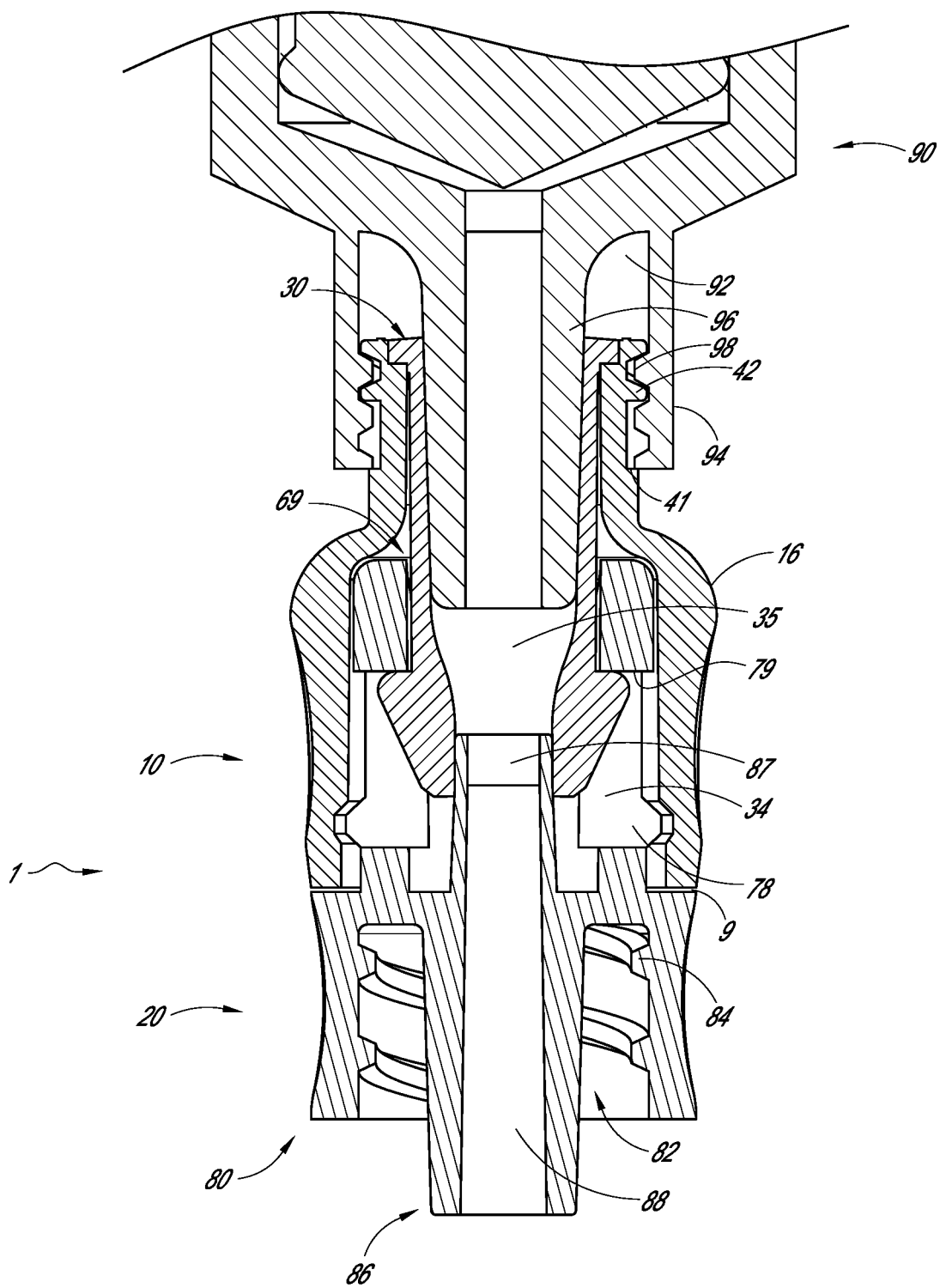
FIG. 13A is a cross-sectional view of an embodiment of a medical connector engaged with a medical device.
Figure 13B:
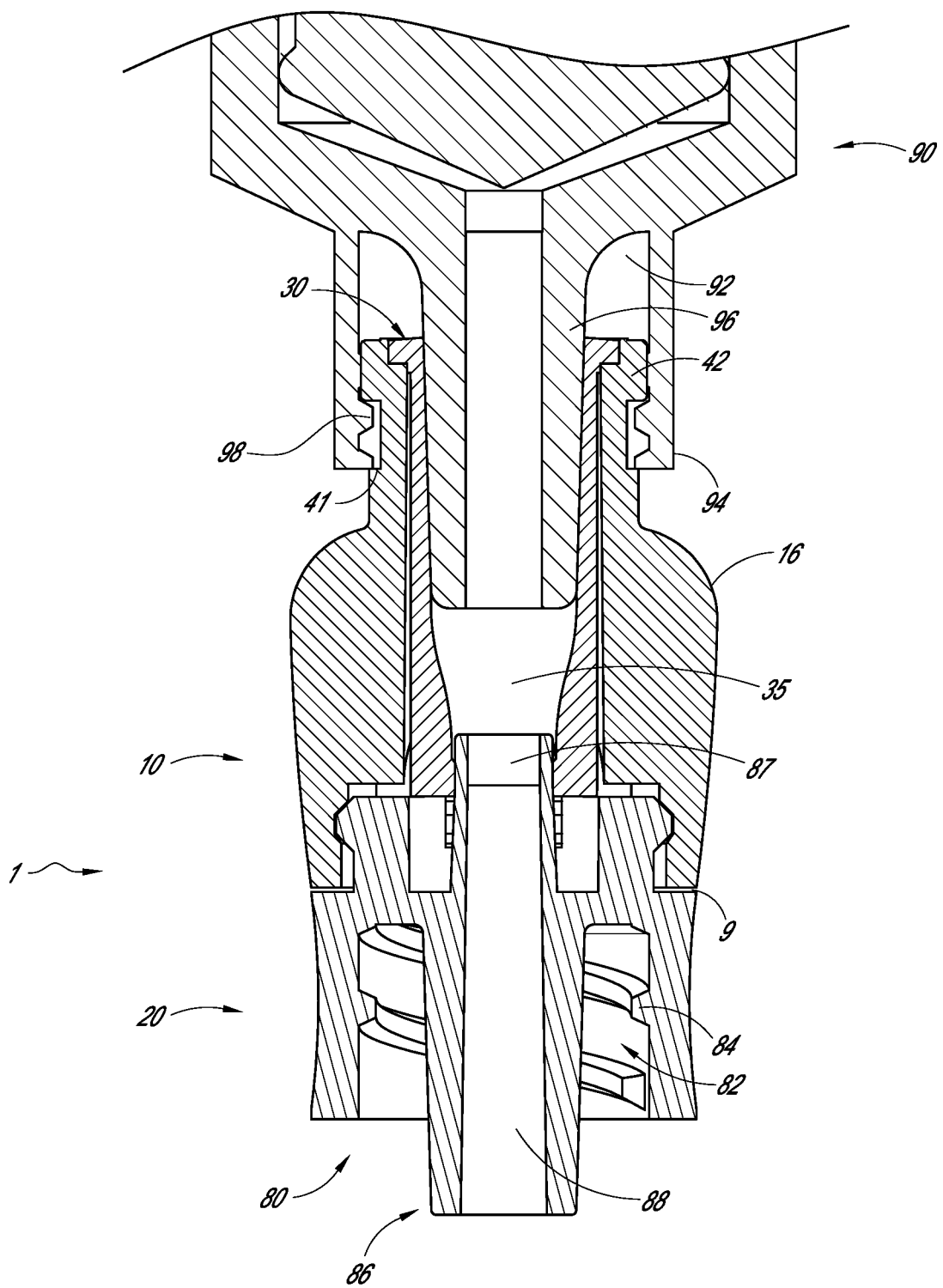
FIG. 13B is a cross-sectional view of a medical connector engaged with a medical device, taken at about 90 degrees relative to the cross-section of FIG. 13A.

FIGS. 13A and 13B illustrate an embodiment of the medical connector where a medical device 90 has been attached to the first housing. FIG. 13A is a cross-sectional view taken from the same angle as the view in FIG. 12A, and FIG. 13B is a cross-sectional view rotated approximately 90° and showing the same side as FIG. 12B. The medical device 90 can have a Luer cannula 96 that extends through a cavity 92 of a connecting region 94. The connecting region can have internal threading 98 that can be configured to mate with the threads 42 of the Luer connector region 40 of the first housing 10. The Luer cannula 96 can enter the valve member 30 through the slit 32 (not visible) and can extend into the internal cavity 35 as the connecting region 94 is screwed onto the medical connector. In some embodiments, the Luer cannula can be configured to be inserted until the connecting region 94 contacts the outer ledge 41. In some embodiments, the Luer cannula 96 can be configured to extend past the outer ledge 41, or in some embodiments the Luer cannula may not have an outer ledge, such that the Luer cannula can be inserted until the connecting region contacts the shoulder 16 of the first housing 10, preventing further insertion of the Luer cannula 96.

As the Luer cannula 96 extends into the valve member 30, friction between the valve member and cannula can tend to stretch the valve member 30 and create additional tension. In some embodiments, this additional tension can cause the valve to slide farther down the cannula 86 of the second housing 20, and the shoulders 34 of the valve member can move off of the upper opening boundary 79 and farther into the opening 78. In some embodiments, however, as illustrated, the shoulders can remain against the upper opening boundary even as the Luer cannula 96 is inserted into the valve.

In some embodiments, the connector 1 can be configured to receive a medical device 90, or a medical device can be configured to attach to the connector, such that the Luer cannula 96 extends only partially into the slit 32. The cannula can extend far enough into the slit to open it, but not all the way through the slit and into the internal cavity 35. In some embodiments, using a medical device 90 configured in this manner can cause the expansion of the slit to be greater than the volume occupied by the cannula within the valve 30. This can create neutral or even positive flow when the Luer cannula 96 is removed, such that fluid is not sucked back up the valve.

Once the medical device 90 has been inserted into the medical connector 1, a fluid flow path can exist from the medical device into the valve member 30 and into the cannula 86 of the Luer connector region 80 of the second housing 20. As discussed above, the first housing 10 and second housing 20 are preferably configured such that their central longitudinal axes are generally in alignment when the housings are joined together. In some embodiments, the medical device 90 can attach to the medical connector 1 such that the longitudinal axis of its Luer cannula 96 is similarly aligned, and the fluid flow path can be substantially straight.

From the cannula 86, fluid can flow into a second medical device (not illustrated) that can attach to the second housing 20. Like the first housing 10, the second housing can have a Luer connector region 80 to facilitate joining the connector 1 to medical devices with female Luer connectors or other types of connections. The Luer connector region 80 can include a cavity 82 with internal threads 84, and the cannula 86 can extend downward to provide a connection with another medical device, such as a catheter hub. In some embodiments, other interfaces and connections can be used in place of or in addition to the Luer connector region 80, such as Luer slip connections, barbed hose fittings, etc. Similarly, though referred to herein as a luer cannula 96, the medical device 90 may include a different shape cannula and the upper luer connection region 40 of the first housing 10 can be configured to accommodate alternative shapes.

In some embodiments, fluid flowing through a medical connector at high flow rates (e.g. about 450 milliliters per minute) can develop air bubbles, especially when flowing from down to up (i.e. from the male Luer connector region 80 to the female Luer connector region 40). When blood is flowing through a medical connector, this can cause hemolysis. Embodiments with straight, vertical walls of the upper section 87 of the cannula 86, discussed above, can help prevent the development of such bubbles.

Additionally, in certain embodiments it can be desirable to have a mechanism for venting the interior space 69 of the first housing 10. For example, it may be desirable to allow air or other gases to escape from the interior space 69 of the first housing while the first housing is attached to a medical device. Additionally, a venting mechanism can allow air or other ambient gases to enter the interior space 69 while a medical device is removed from the first housing 10 in order to help prevent a vacuum forming that can lock the medical device to the housing or make its removal difficult. A venting mechanism can also allow water, cleaning or disinfecting solutions, or other liquids to escape the interior space 69 while the first housing 10 is connected to a medical device.

In some embodiments, a gap 9 between the first housing 10 and the second housing can help create a venting mechanism. The gap 9 can lead to the openings 78, creating a fluid connection from the ambient environment outside of the connector 1, through the gap 9, through the openings 78, and into the interior space 69 of the first housing. This connection can serve as a venting mechanism. In some embodiments, the gap 9 can be greater than or equal to about 0.1 millimeters and/or less than or equal to about 0.2 millimeters. In some embodiments, the gap can be greater than or equal to about 0.05 millimeters and/or less than or equal to about 0.3 millimeters. In some embodiments, the first and second housing can be constructed such that no gap exists between the first housing and second housing, or such that no functional gap exists between the housings.

Valve Inserts

Figure 14:
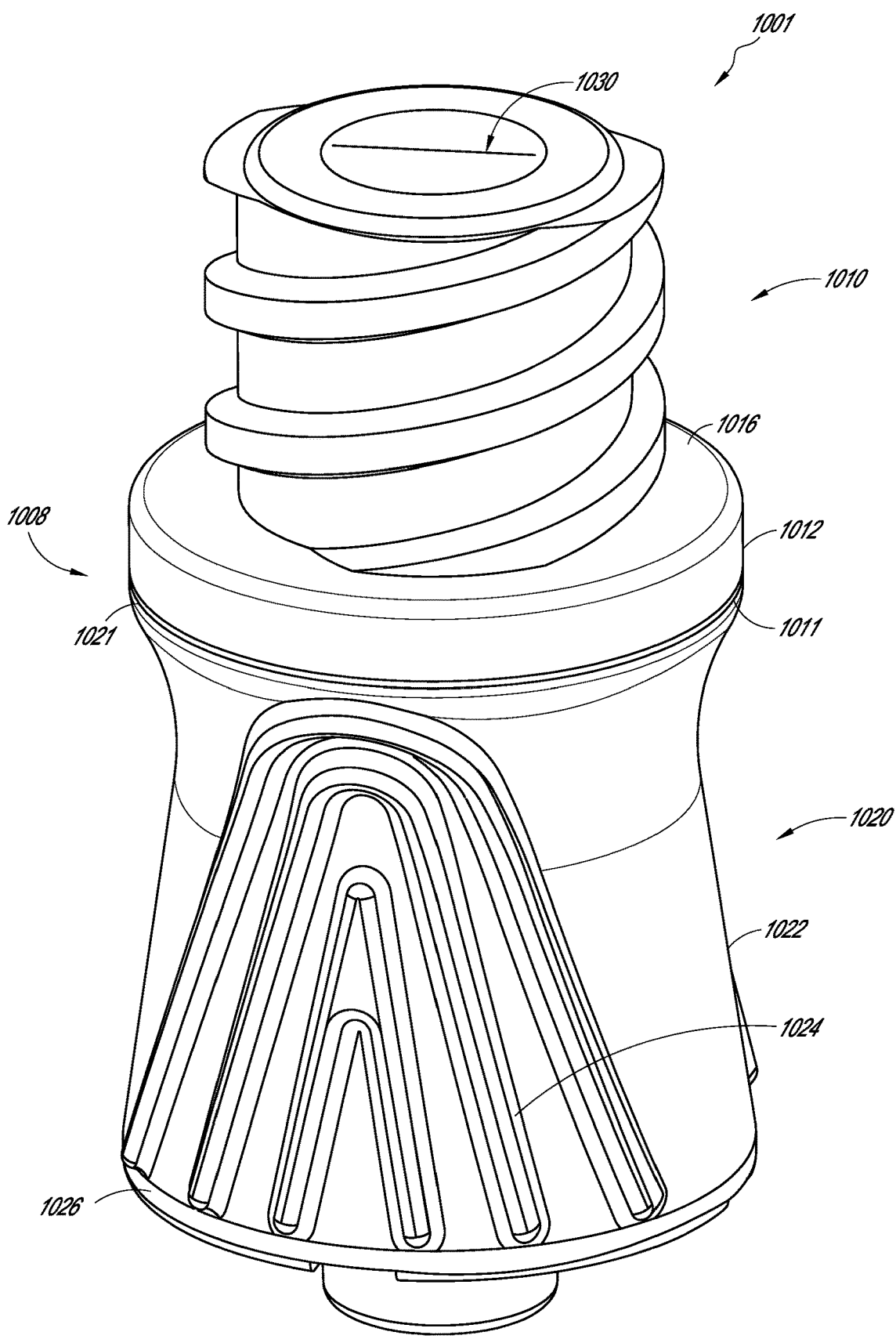
FIG. 14 is a perspective view of one embodiment of a medical connector.

FIG. 14 illustrates one embodiment of a medical connector 101. The embodiment of FIG. 14 and the embodiments described below are similar in many respects to the embodiments described above. To the extent that specific differences are not provided, similarly numbered elements can be considered to have similar functions to elements previously described. Similarly, components that are not specifically called out or discussed can be considered to function similarly to their counterparts described elsewhere herein. Additionally, to the extent possible, it is contemplated that elements of any embodiment discussed in this disclosure can be combined with other elements of any other embodiment.

Like the embodiments discussed above, the embodiment of FIG. 14 comprises a housing 1008 and a valve member 1030 positioned at least partially within the housing. The housing 1008 can include a first housing 1010 and a second housing 1020. As described above, the second housing 1020 can include elements designed to improve a grip on the medical connector. In some embodiments, as illustrated, the second housing 1020 can include elevated ridges 1024. The elevated ridges 1024 can be a series of curved arcs that run up from a lower end of the housing toward an upper end of the housing, turn, and run back toward the lower end of the housing. This shape can make it easier for the fingers of an individual that grips the connector to slide up along the housing 1020 until they reach the curves of the elevated ridges 1024, which can arrest motion of the fingers relative to the housing. In some embodiments, as illustrated, the ridges can be farther apart from each other toward a lower end of the second housing 1020 than they are toward an upper end of the second housing. The relative proximity of the ridges 1024 at the upper end of the housing where they curve can increase the arresting effect of the ridges on the sliding motion of a user's fingers.

Also, as described above, the outer surface 1022 of the second housing 1020 can have a concave profile along a path from the upward facing surface 1021 to the lower edge 1026 of the second housing. In some embodiments, and as illustrated here, series of elevated ridges 1024 can be closest to each other near the deepest point of the concavity in the second housing 1020. This can help improve the gripping surface because if a user grabs the connector toward a lower end of the second housing, his or her fingers will naturally slide along the series of elevated ridges 1024 and toward the lowest point of the concavity where they will be in contact with the curved, more tightly packed sections of elevated ridges 1024.

FIG. 14 also illustrates one embodiment where the height of the first housing 1010 (i.e., the distance from shoulder 1016 to bottom surface 1011) is less than the height of the second housing 1020 (e.g., the distance from the lower edge 1026 to the upward facing surface 1021).

FIGS. 15A-15C illustrate one embodiment of a valve member 1030 that can be configured to be used in a medical connector 1001, such as the connector of FIG. 14. The valve member 1030 can also be configured for use, however, with other embodiments of medical connectors described above and below. FIG. 15A illustrates a perspective view of the valve member 1030, and FIGS. 14B and 14C illustrate cross-sectional views of the valve member 1030 taken from cross sections rotated approximately 90° relative to each other. FIG. 15B is a cross sectional view in a plane parallel to the orientation of the slit 1032 in the valve.

As above, the valve member can include a top surface 1050, a lip 1052 extending outward from the central body 1033 of the valve member, a flat section 1133 on the central body, and a lower surface 1054 of the lip. Unlike the embodiments illustrated above, however, FIGS. 15A-15C illustrate an embodiment of a valve member with a single lip 1052. The valve member 1030 can have a slit 1032 that extends into an internal cavity 1035, which in turn extends down to a lead lumen 1036. In the cross section taken along the length of the slit along the top surface 1050 (i.e. FIG. 15B), the internal cavity 1035 can maintain substantially the same width as it extends toward the lead lumen, such that the width $w_{101}$ of the slit 1032 at the top 1050 of the valve member is approximately equal to the width $w_{102}$ at the bottom of the internal cavity 1035, before a tapered section 1137 that connects to the lead lumen 1036. In some embodiments, the width $w_{101}$ can be slightly less or greater than the width at the bottom $w_{102}$. Similar to embodiments discussed above, in a cross section taken at 90° to the length of the slit, and as visible in FIG. 15C, the width of the internal cavity 1035 can expand from a point at the surface 1050 of the valve 1030 to a width wider than the lead lumen 1036, before reaching the tapered section 1137 to the lead lumen.

Also as above, the valve member can include two shoulders 1034 positioned on opposite sides of the valve member. As illustrated, in some embodiments the top surface 1136 of the shoulders can be generally horizontal and/or can form a generally right angle with the central body 1033 of the valve. In some embodiments, also as illustrated, the side surface 1138 of the shoulders can be generally vertical and/or form a generally right angle with the top surface. Further, in some embodiments the outer section 1134 of the valve member can be an outer edge.

In some embodiments, the width $w_{102}$ of the internal cavity 1035 adjacent the tapered section 1137 in the plane with the shoulders (i.e. the plane of FIG. 15B) can vary from the width $w_{111}$ of the internal cavity adjacent the tapered section in the plane rotated 90 degrees from the plane with the flat section 1133 (i.e. the plane of FIG. 15C). As illustrated, the width $w_{111}$ in the plane with the flat section is greater than the width $w_{102}$ in the plane with the shoulders. In some embodiments, the width in the plane with the flat section can be less than the width in the plane with the shoulders. In some embodiments, the widths can be equal to each other.

In some embodiments, the upper surface 1050 of the valve member 1030 can be flat or nearly flat while the valve member is in a first state, before it is placed into the second state.

In some embodiments, as illustrated in FIG. 15C, the angle $\alpha_{104}$ of the flat section 1133 of the valve member can be approximately equal to the angle $\alpha_{105}$ of the surfaces 1053 of the internal cavity 1035 in this plane. In such embodiments, the width of the walls of the central body 1033 at the flat section 1133 can remain generally constant along the length of the flat section.

Figure 16B:
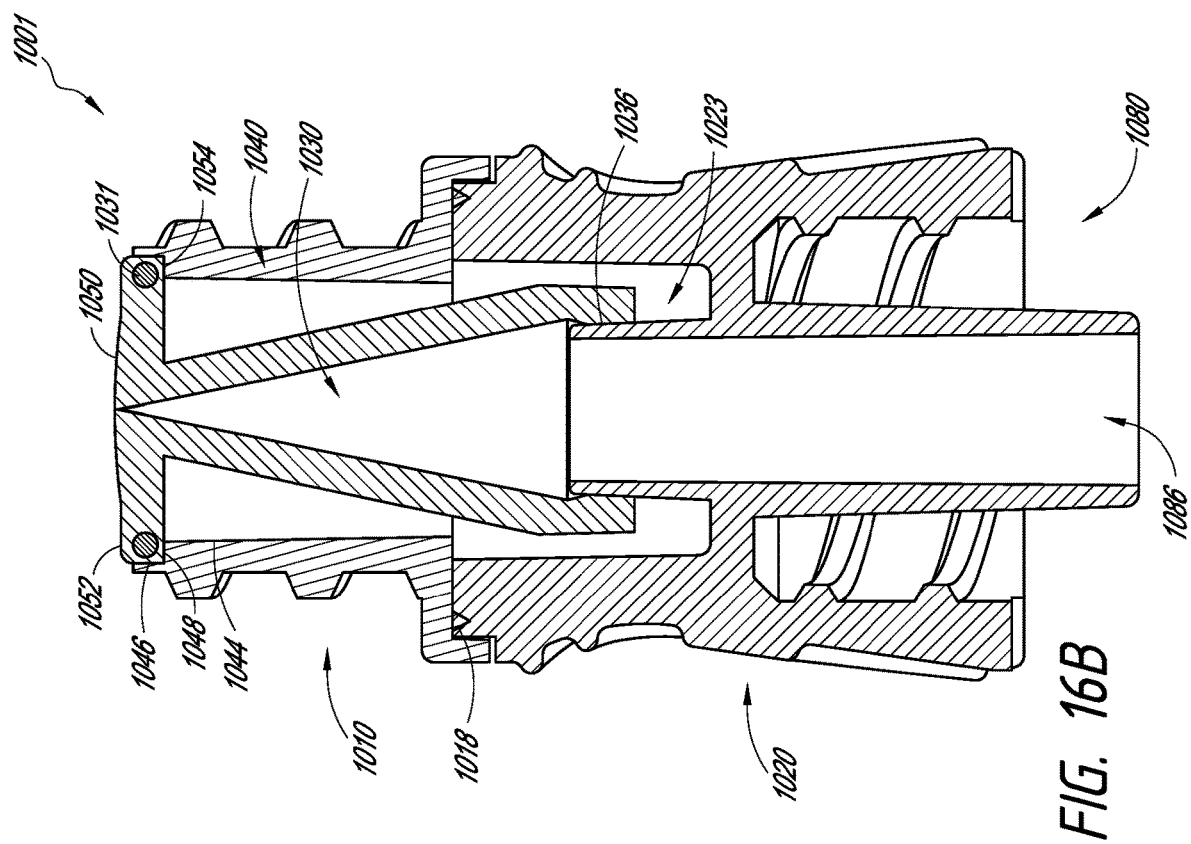
FIG. 16B is a cross-sectional view of a medical connector with the valve member of FIG. 15A, taken at about 90 degrees relative to the cross-section of FIG. 16A.
Figure 16A:
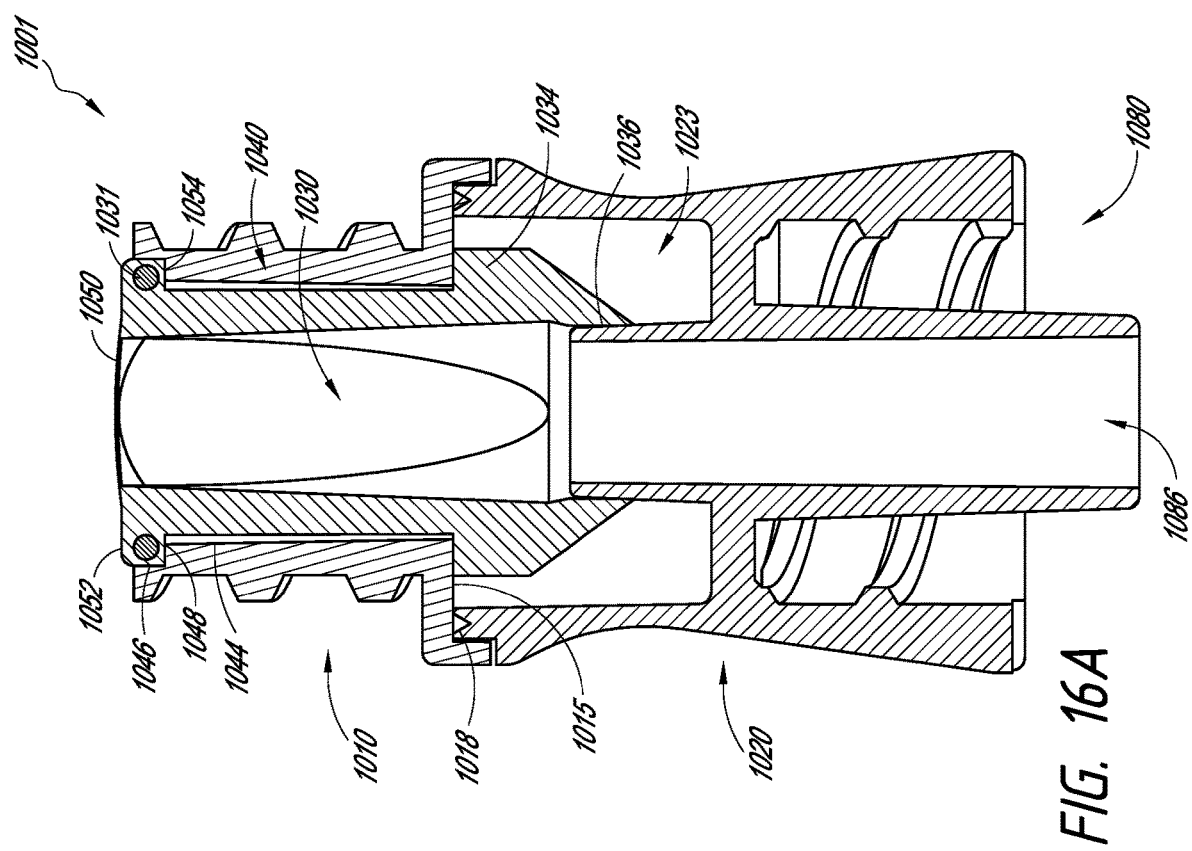
FIG. 16A is a cross-sectional view of a medical connector with the valve member of FIG. 15A.

With continued reference to FIGS. 15A-15C, in some embodiments the valve member 1030 can be molded around a valve insert 1031. The valve insert can be used to provide extra support for the valve member as it is stretched and placed into tension to surround a portion of a cannula, as illustrated in FIGS. 16A and 16B. The valve insert can be a rigid ring that is centered on a central axis of the valve. In some embodiments, the valve insert can be positioned at least partially within the lip 1052. In some embodiments, the valve insert can have a round or circular cross section, as illustrated, although in some embodiments it can have other cross sections such as a square, oval, triangle, etc.

FIGS. 16A and 16B illustrate cross sections taken at 90° relative to each other of valve member 1030 when in a second state within a medical connector 1001. FIG. 16A is a cross section taken in the same plane as FIG. 15B, while FIG. 16B similarly corresponds to FIG. 15C. As described above, the first housing 1010 can have a Luer connector region 1040 that includes a first section 1044 with an inner diameter that is less than that of a second section 1046, and a ledge 1048 between the first and second sections. The lower surface 1054 of the lip 1052 can seat onto the ledge. As the lead lumen 1036 is stretched to fit around the cannula 1086 (as described above), placing the valve member 1030 in tension, the valve insert 1031 can brace against the ledge 1048 and provide additional support for the valve member. This additional support can help prevent the top surface 1050 from moving downward. In some embodiments, this can help keep the top surface 1050 flat and swabbable. In some embodiments where the valve is not molded within the first housing 1010 the valve insert can help prevent the valve from folding inward or slipping when pulled into tension.

Additionally, and as described above, the shoulders 1034 of the valve member can serve to brace the valve member 1030 and maintain it in a second state once it has been placed around the cannula 1086. However, rather than snapping into openings within upward projections of the second housing 1020, the shoulders can have room to expand into an upper cavity 1023 of the second housing. The tops of the shoulders can be positioned beneath a lower ledge 1015 of the first housing 1010, which can prevent the valve member 1030 from retracting upward and maintain the valve member in tension. In such embodiments, because the shoulders can expand generally into the upper cavity 1023 of the second housing, the first and second housing can be assembled together in any alignment.

FIGS. 16A and 16B also illustrate an alternative method of joining the first housing 1010 and the second housing 1020. Rather than having an annular recess along an interior surface of the first housing and an annular projection on an exterior surface of the second housing that can mate with the annular recess, FIGS. 16A and 16B illustrate a weld 1018, such as an ultrasonic weld, that can join the two housings. Additionally, in some embodiments the medical connector can have a cannula 1086 with a constant diameter and straight interior walls. In some embodiments, the cannula can have a slight taper from a lower end to an upper end.

FIGS. 17A-17C illustrate one embodiment of a valve member 2030. The valve member is illustrated in a second state, and the top surface 2050 is slightly depressed. As discussed above, however, in different embodiments the top surface 2050 can be flat when in the second state or slightly convex. It can also be slightly convex or flat in the first state. FIG. 17A illustrates a perspective view of a valve 2030, and FIGS. 17B and 17C illustrate cross-sectional views of the valve member 2030 taken from cross sections rotated approximately 90° relative to each other. FIG. 17B is a cross sectional view in a plane parallel to the orientation of the slit 2032 in the valve.

As illustrated in FIGS. 17B and 17C, the valve member 2030 can comprise a rigid valve insert 2031 which, as above, is a rigid ring about which the valve member can be over-molded. The valve insert 2031 can have a generally square or other shaped cross section. In some embodiments, as described above, the valve member can comprise a first lip 2052 and a second lip 2052' below the first lip and not extending as far outward as the first lip. The second lip can have a lower surface 2054' and the first lip can have a lower surface 2054.

In some embodiments, the side surface 2138 of the shoulders 2034 can have a curved profile, most easily visible in FIG. 17B. In some embodiments this curved profile can be a concavity. Similarly, in some embodiments the valve member can have a curved section 2150 below the flat section 2133 of the central body 2033 of the valve. In some embodiments, the internal cavity 2035 can include a curved section 2152 that is adjacent the tapered section 2137 that connects to the lead lumen 2036. In some embodiments, as illustrated, the curved section 2152 can be around the entire circumference of the internal cavity 2035. In some embodiments, it can be around just a portion of the circumference of the internal cavity such that its profile is visible in only one of the cross sections of FIGS. 17B and 17C.

Figure 18B:
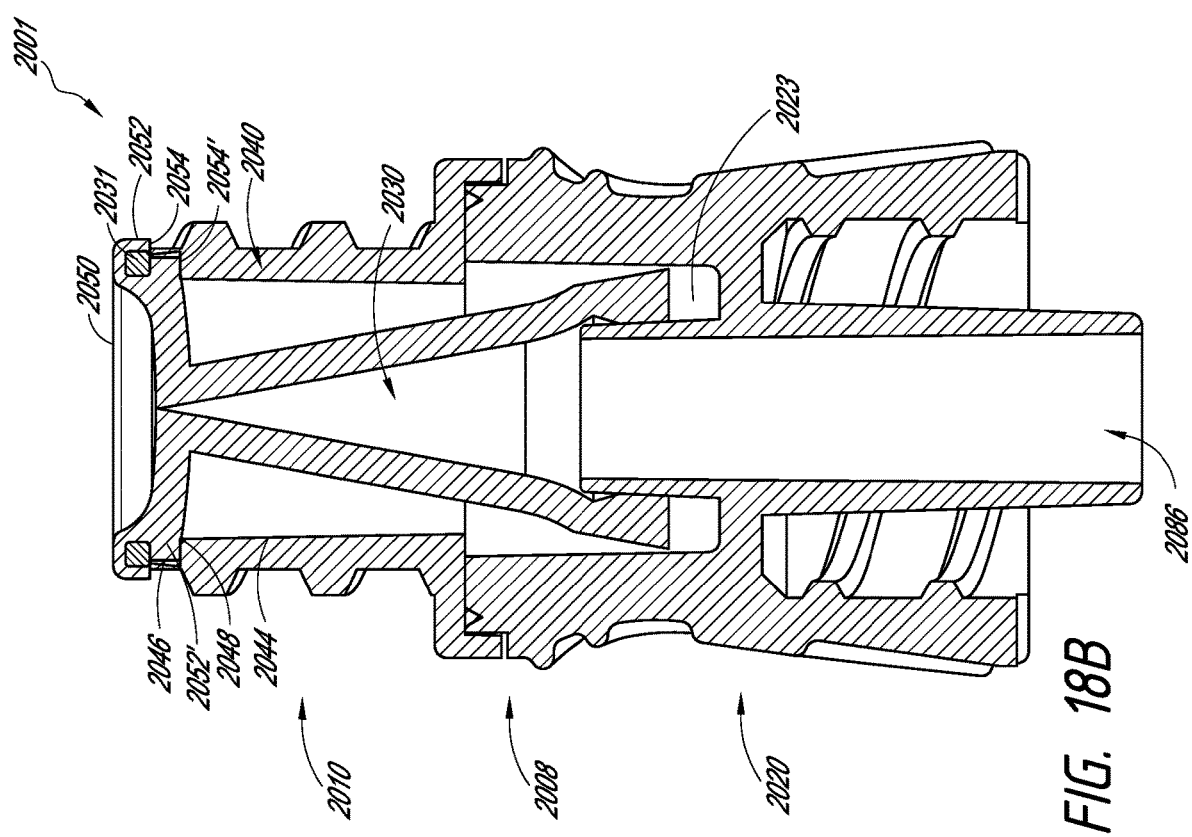
FIG. 18B is a cross-sectional view of a medical connector with the valve member of FIG. 17A, taken at about 90 degrees relative to the cross-section of FIG. 18A.
Figure 18A:
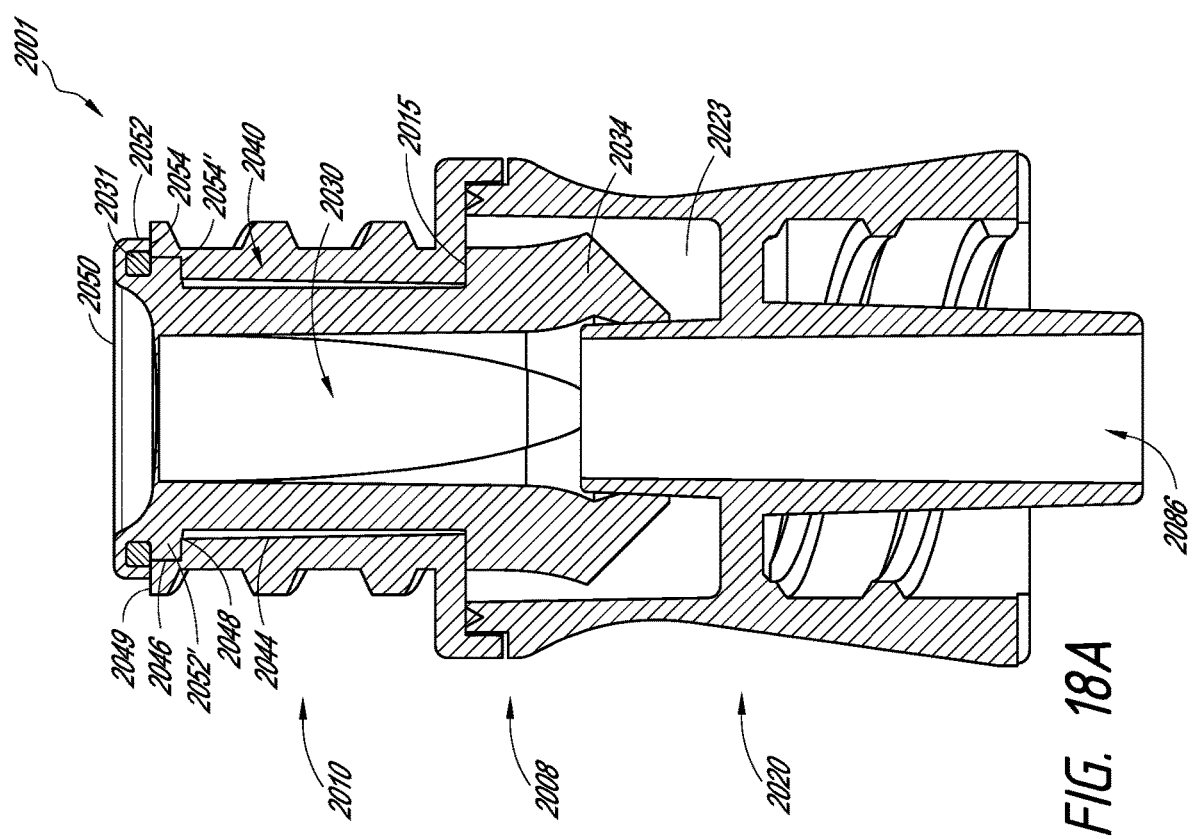
FIG. 18A is a cross-sectional view of a medical connector with the valve member of FIG. 17A.

FIGS. 18A and 18B illustrate cross sections taken at 90° relative to each other of a valve member 2030 when in a second state within a medical connector 2001. FIG. 18A is a cross section taken in the same plane as FIG. 17B, while FIG. 18B similarly corresponds to FIG. 17C.

The valve member 2030 can be used within a housing such as that of FIG. 13 and FIGS. 16A and 16B, or can alternatively be used in other housing embodiments. As illustrated in FIGS. 18A and 18B, in some embodiments with a valve with first and second (or upper and lower) lips, the lower lip surface 2054' can seat on the ledge 2048. Additionally, the lower surface 2054 of the upper lip 2052 can seat on the uppermost surface 2049 (an upper ledge) of the Luer connector region 2040 of the first housing 2010. These two planes of contact can provide additional support for the valve member 2030 as it is pulled into tension and placed around the cannula 2086. In some embodiments, the valve insert 2031 is positioned at least partially within the upper lip 2052 such that it extends over at least a portion of the upper surface 2049 of the first housing. In some embodiments, the valve insert 2031 can be positioned within the lower lip 2052', at least partially below the upper lip 2052 and below the upper surface 2049 of the first housing.

Figure 19C:
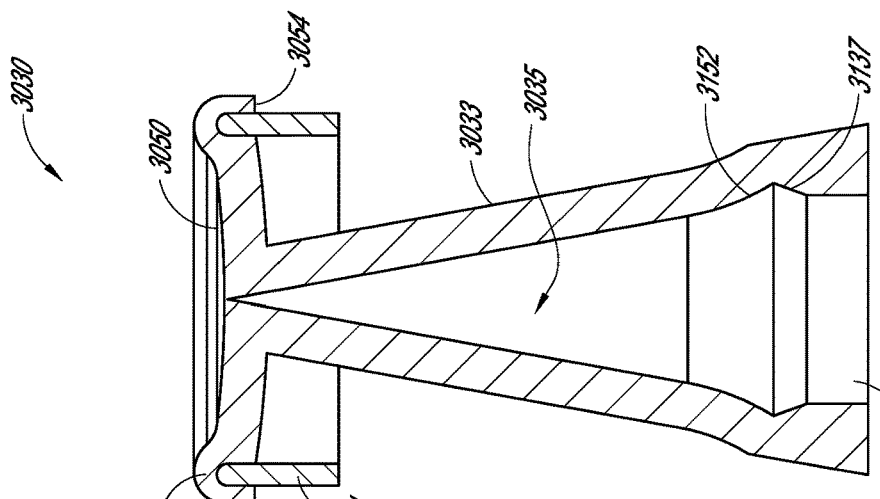
FIG. 19C is a cross-sectional view of the valve member of FIG. 19A taken at about 90 degrees relative to the cross-section of FIG. 19B.
Figure 19B:
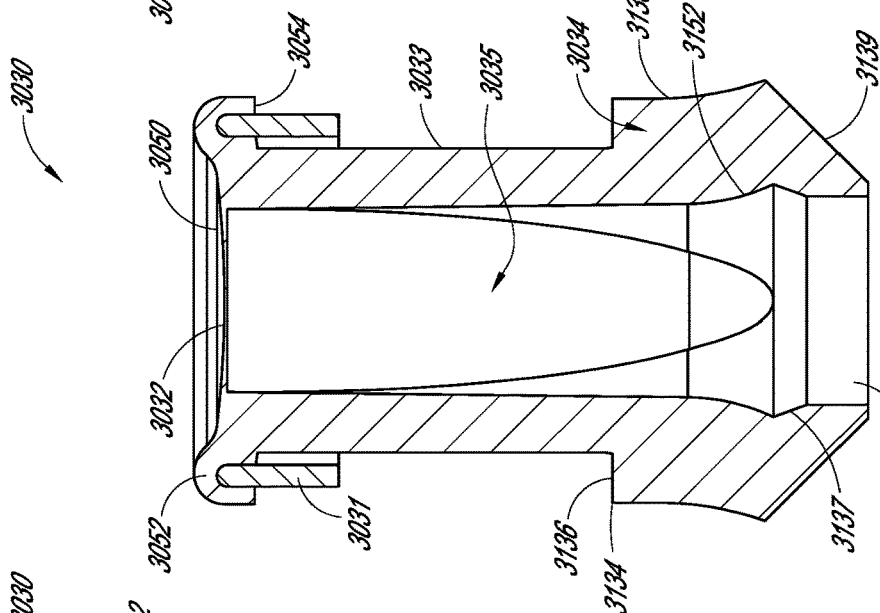
FIG. 19B is a perspective view of one embodiment of the valve member of FIG. 19A.
Figure 19A:
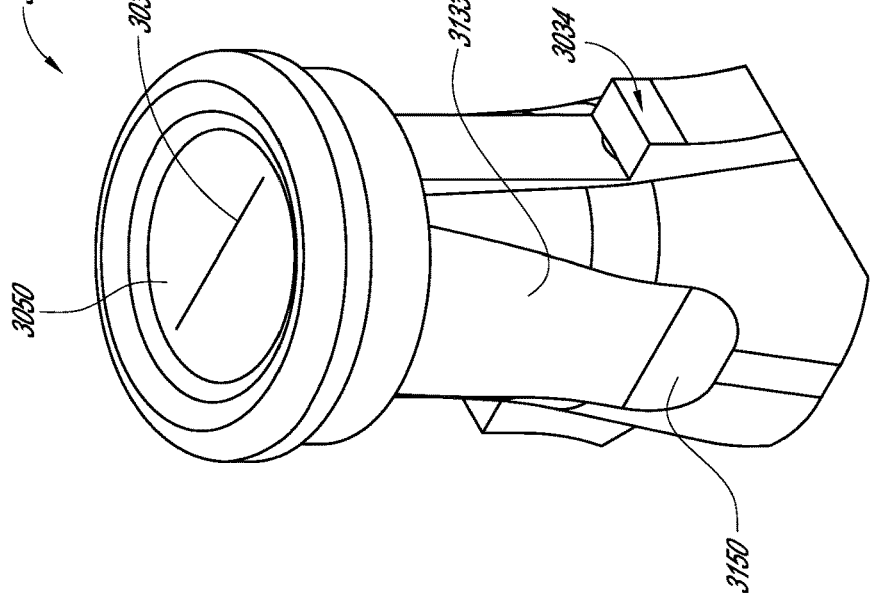
FIG. 19A is a perspective view of one embodiment of a valve member.

FIGS. 19A-19C illustrate one embodiment of a valve member 3030. FIG. 19A illustrates a perspective view of a valve 3030, and FIGS. 19B and 19C illustrate cross-sectional views of the valve member 3030 taken from cross sections rotated approximately 90° relative to each other. FIG. 19B is a cross sectional view in a plane parallel to the orientation of the slit 3032 in the valve.

As illustrated, rather than having a valve insert 3031 positioned entirely within the valve member 3030, in some embodiments a valve member can be molded about just a portion of the valve insert 3031. This can allow for a larger valve insert that can provide a greater amount of support and rigidity for the valve. For example, and as illustrated, in some embodiments the valve insert can be a section of a cylinder that is attached to the valve within the lip 3052 and that extends from the lower surface 3054 of the lip to a position outside of the valve and around at least a portion of the central body 3033 of the valve. In some embodiments the valve can be overmolded around the valve insert.

Figure 20B:
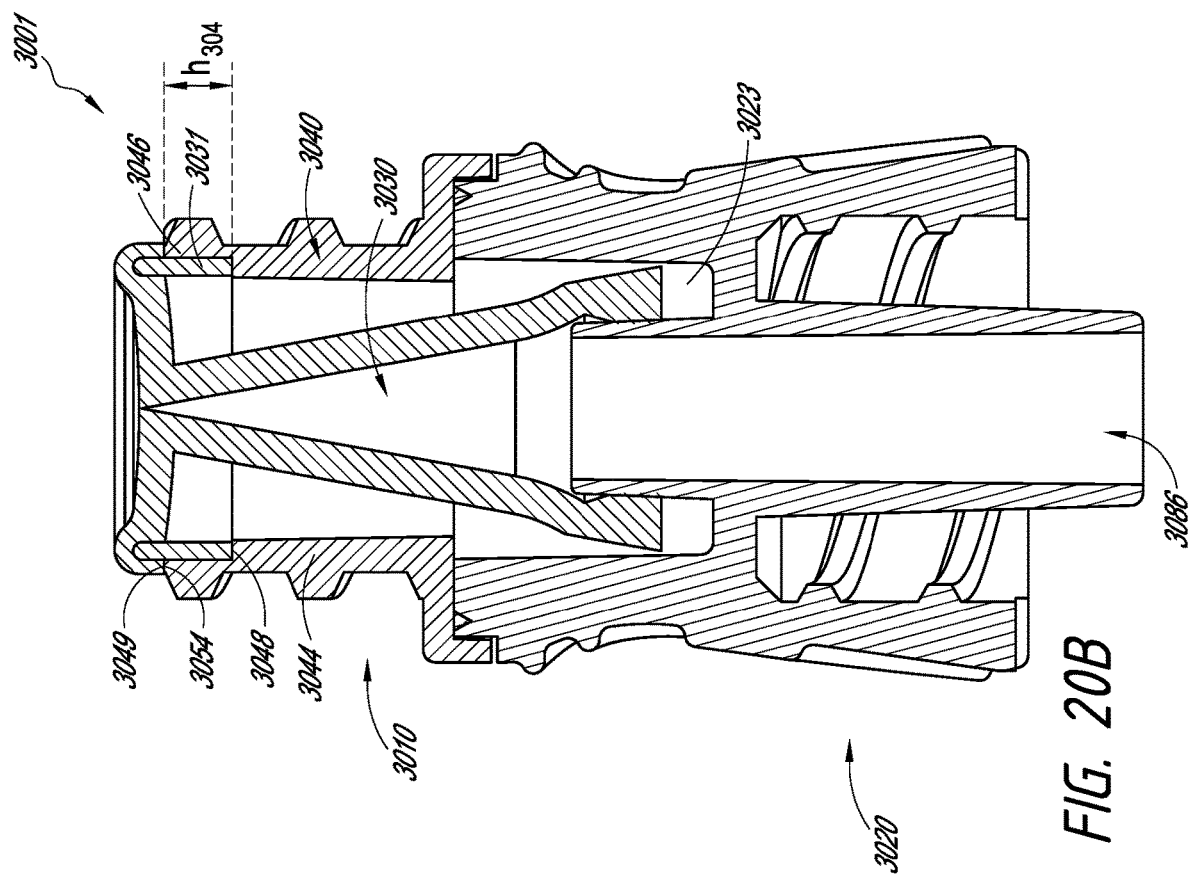
FIG. 20B is a cross-sectional view of a medical connector with the valve member of FIG. 19A, taken at about 90 degrees relative to the cross-section of FIG. 20A.
Figure 20A:
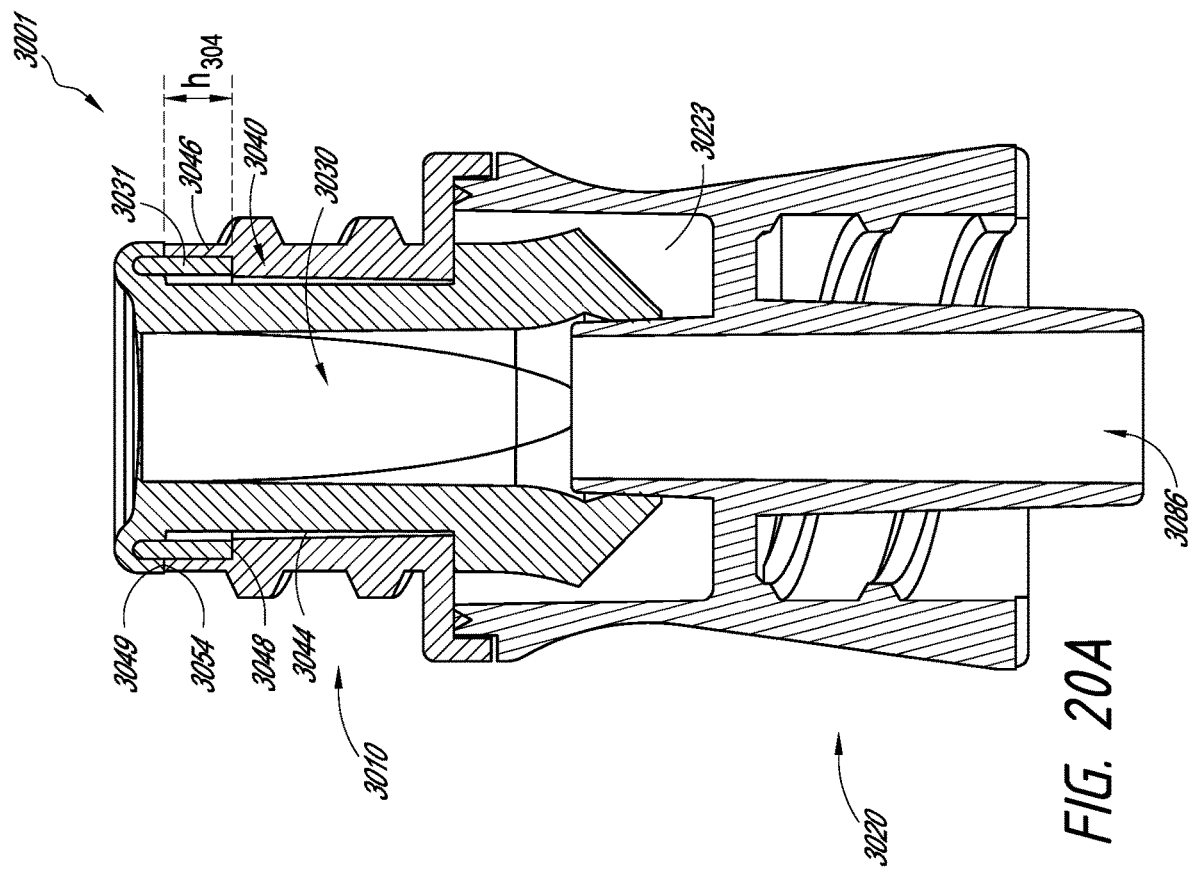
FIG. 20A is a cross-sectional view of a medical connector with the valve member of FIG. 19A.

This type of valve insert can also provide increased rigidity and support for the valve member 3030 because, by having the insert extend out of the valve, in some embodiments the insert can be placed directly against a ledge 3048 of the housing, as illustrated in FIGS. 20A and 20B. FIGS. 20A and 20B illustrate cross sections taken at 90° relative to each other of valve member 3030 when in a second state within a medical connector 3001. FIG. 20A is a cross section taken in the same plane as FIG. 19B, while FIG. 20B similarly corresponds to FIG. 19C.

The valve member 3030 can be used with the various embodiments of first housings described above, but depending on the size of the valve insert the first housing 3010 may need to be modified to accommodate the insert. For example, in the illustrated embodiment, the first housing 3010 has a first section 3044 and a second section 3046 with an inner diameter greater than that of the first section 3044, as discussed above. However, in some embodiments the height $h_{304}$ of the second section 3046 can be varied to allow the valve insert 3031 to be positioned against the ledge 3048, while also allowing the lower surface 3054 of the lip 3050 of the valve to contact the upper surface 3049 of the Luer connector region 3040 of the first housing 3010.

Rolling Valve

FIGS. 21-23 illustrate the components of an alternative embodiment of a medical connector. FIG. 21 illustrates the first housing, or outer body, 4010 which can include a plurality of depressions 4014 positioned around the outer surface 4012 of the outer body. The depressions can comprise flat or curved side walls 4019 that extend from the outer surface 4012 to a bottom surface 4017 of the depressions 4014. As illustrated, the bottom surface 4017 can have a width along a circumference of the outer body 4010 that can be approximately the same as the width of the outer surface 4012 of the outer body between adjacent depressions. In some embodiments, the width of the bottom surface 4017 can be less than or greater than the width of the outer surface 112 between adjacent depressions.

The size and number of depressions can vary in different embodiments, but in some embodiments they are generally oriented symmetrically about the outer body such that each depression has a corresponding depression on an opposite side of the outer body. As discussed above, this can improve the gripping process by allowing the fingers of a user to be placed on opposite sides of the outer body in order to pinch it while allowing each finger to be within a depression. Additionally, the width of the outer surface 4012 between adjacent depressions can be less than the average width of a thumb or forefinger, or in some embodiments less than half of the average width of a thumb or forefinger, such that a user's fingers will naturally slide from the outer surface into the depressions when the medical connector is grasped. In some embodiments the width of the outer surface between adjacent depressions can be greater than or equal to about 0.5 centimeters and/or less than or equal to about 2 centimeters.

Figure 25:
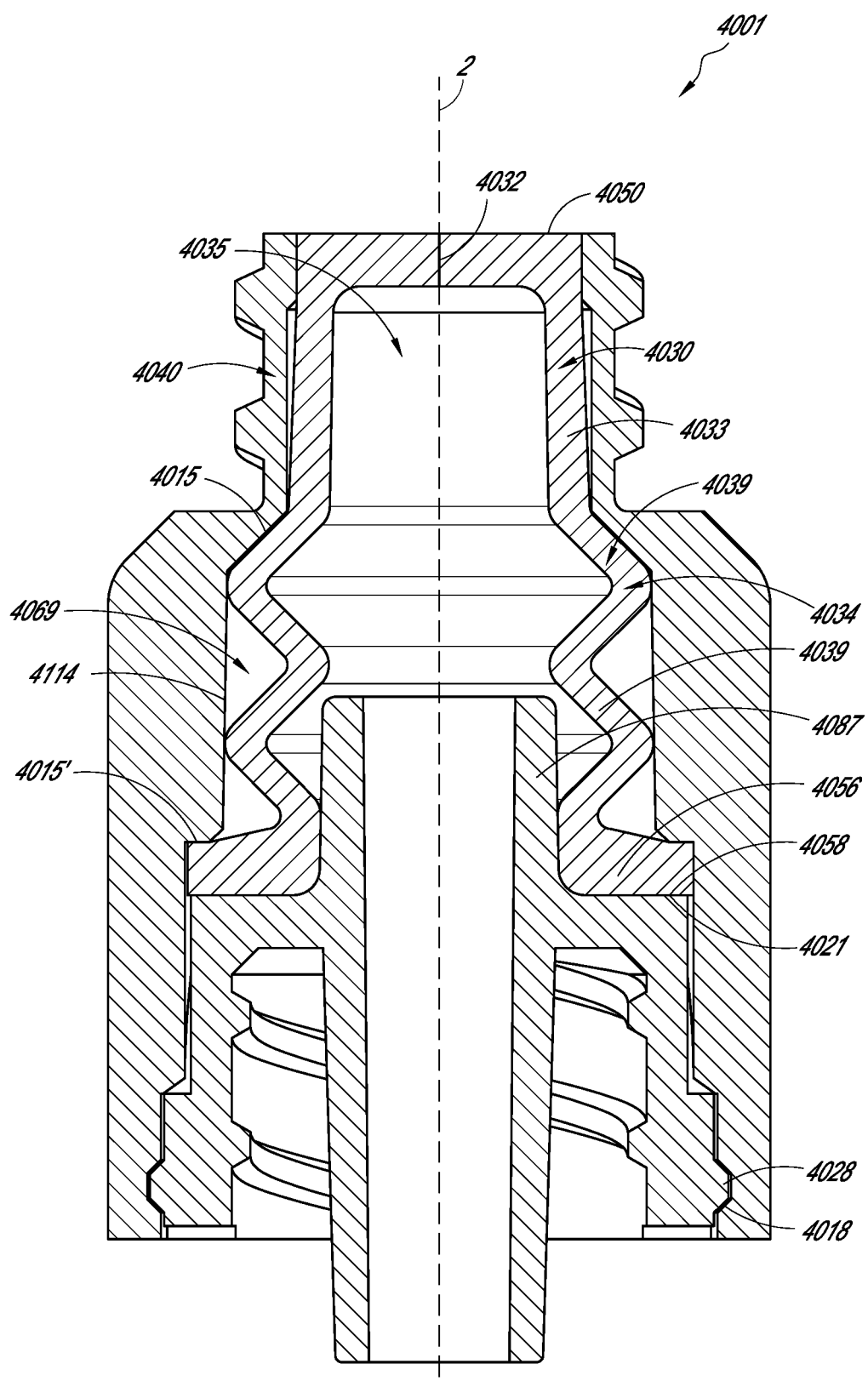
FIG. 25 is a cross-sectional view of the medical connector of FIG. 24.

FIG. 22 illustrates an embodiment of an inner body 4020, which when assembled as part of a medical connector can be completely within or at least partially within the outer body 4010. The inner body can include a cannula 4086 that runs through the inner body, with a lower section 4088 of the cannula extending out below the inner body from a Luer connector region 4080, and an upper section 4087 of the cannula extending up above the inner body from top surface 4021. The inner body can also include an annular projection 4028 which can be sized and configured to fit within an annular recess 4018 of the outer body, as illustrated in FIG. 25.

The inner body can also have a plurality of cutouts 4070 which are cut into the outer surface 4022 of the inner body and can extend from or near the top surface 4021 downward toward the annular projection 4028. In some embodiments, the interior surface of the outer body can have at least one projection sized and configured to mate with the cutouts. This mating can help maintain a desired orientation of the inner body relative to the outer body, and can help prevent rotation once the outer and inner bodies have been assembled together. Also as illustrated, the edges of adjacent cutouts 4070 can be angled away from each other as they run from at or near the top surface 4021 toward the annular projection 4028. They can also come to a point, or edge, at or near the top surface, which creates a generally triangular shape in the outer surface 4022, as illustrated. This point, or edge, can make it so that the corresponding projections within the outer body will not jam against the outer surface if misaligned but will instead naturally slide into the cutouts.

Figure 23B:
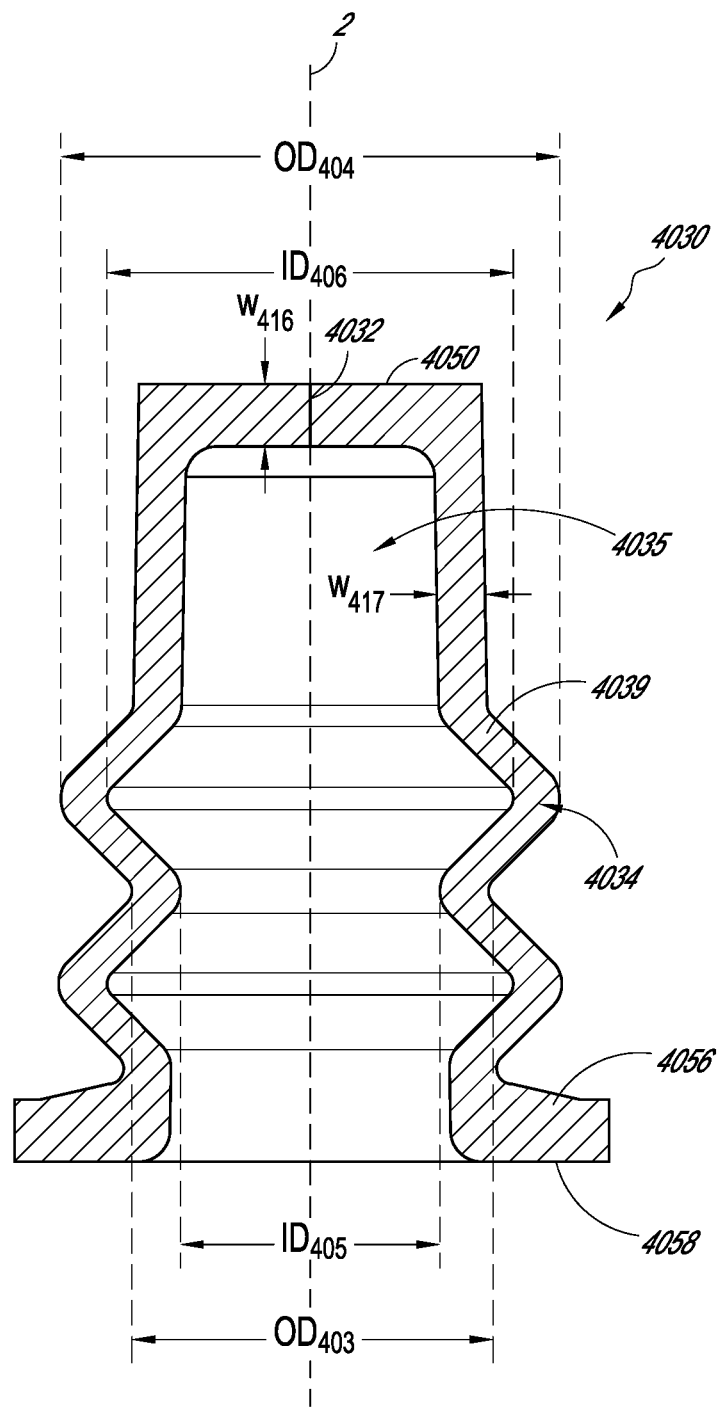
FIG. 23B is a cross-sectional view of the valve member of FIG. 23A.

FIGS. 23A-23B illustrate one embodiment of a valve member 4030. FIG. 23A is a perspective view of the valve member, while FIG. 23B is a cross-sectional view. As above, the valve member can include a slit 4032 in the top 4050 of the valve that extends into an internal cavity 4035 of the valve. As can be seen more clearly in FIG. 23B, in some embodiments the internal cavity 2035, rather than being a gradually expanding opening that extends to a lead lumen as in previous embodiments, can instead run through the base 4056 of the valve. Additionally, in some embodiments the cavity can have a symmetric interior such that it has the same vertical cross section no matter the angle at which the cross section is taken.

The valve 4030 can also comprise one or more bulging sections 4034 when the valve is in an first state. Each section 4034 can have an inner and outer diameter that increases from an original value (e.g. the inner diameter $ID_{405}$ and outer diameter $OD_{403}$ of FIG. 23B) to a local maximum value (e.g. the inner diameter $ID_{406}$ and outer diameter $OD_{404}$ of FIG. 23B), and then decreases to a local minimum value. This increase and decrease of the inner and outer diameters creates angled segments 4039 that are angled relative to the central longitudinal axis 2 of the valve member. In some embodiments, as illustrated, the inner and/or outer diameters can increase and decrease at a generally constant rate between curved end segments 4037 of the bulging sections 4034, such that the angled segments 4039 can have a constant angle. In some embodiments, the outer surface 4148 and/or the inner surface 4146 of the angled segments 4039 can have a varied angle relative to the longitudinal axis of the valve member. In some embodiments, the slope along any point of the angled segment 4039 between the curved end segments 4037 can form an angle with the longitudinal axis that is between about 30° and about 60°.

Because of the angled segments 4039, the bulging sections 4034 can be less resistant to a compressive force parallel to the longitudinal axis of the valve 4030 than other sections of the valve member. In some embodiments, the angled segments 4039 can be configured such that when the valve receives a compressive force along its longitudinal axis (e.g. when a Luer cannula from a medical device is being inserted), the bulging sections 4034 will completely fold in (e.g. such that the slope of the angled segments 4039 approaches zero) before the slit 4032 opens or begins to open. This is discussed further below.

As illustrated in FIG. 23B, in some embodiments the top 4050 of the valve member can have a width $w_{416}$ that is greater than the width $w_{417}$ of the upper side walls 4033 of the valve member. In some embodiments, the ratio $w_{416}/w_{417}$ of these two widths can be greater than or equal to about 1 and/or less than or equal to about 2. The greater relative width of the top 4050 of the valve can make the top 4050 of the valve member and the slit 4032 more resistant to bending and opening when a medical device connects to the Luer connector region 4040 of outer body 4010. Thus, a greater force is required to access the device, which can contribute to a compression of the bulging sections 4034, as discussed below.

Additionally, in some embodiments the valve member 4030 can have walls that vary in thickness in different sections of the valve. For example, the upper side walls 4033 can have a different width than the walls of the bulging sections 4034. Similarly, the base 4056 of the valve can have a different width than sections of the walls and of the top 4050. In some embodiments, the base can be thicker than any of the walls and thicker than the top 4050. This can help support the valve as it is compressed.

Figure 24:
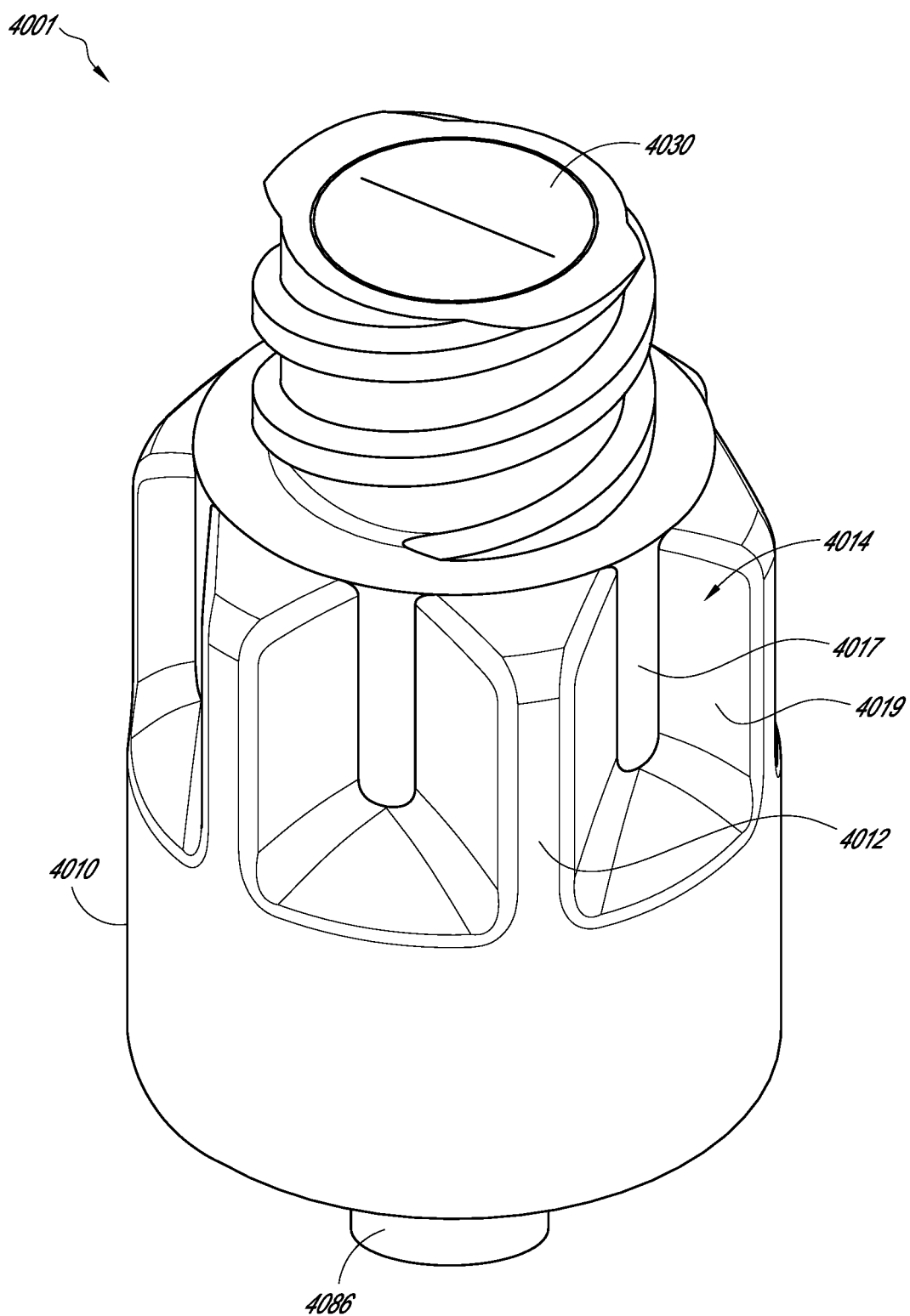
FIG. 24 is one embodiment of an assembled medical connector with the components of FIG. 21-23.

FIGS. 24 and 25 illustrate fully assembled embodiments of a medical connector 4001 using the elements of FIGS. 21 through 23B. As can be seen in FIG. 24, the outer body 4010 can completely surround the inner body 4020, with the exception of the Luer cannula 4086 that extends out below the outer body. FIG. 25 illustrates a cross-sectional view of the assembled medical connector 4001. In this embodiment, the cross-sectional view is not dependent upon the angle at which it is taken, but is consistent around the entire circumference of the connector.

In some embodiments, as illustrated, the valve member 4030 does not need to be stretched and placed in a second state in order to be positioned around the upper section 4087 of Luer cannula 4086. The valve member 4030, outer body 4010, and inner body 4020 can be configured such that the valve member can reach the Luer cannula 4087 while in the first state when the connector is assembled. In some embodiments, the inner diameter of the cavity 4035 at the base 4056 of the valve can be less than the outer diameter of the cannula 4087 at the top of the cannula, such that the valve may still need to stretch to fit around the cannula. This can help maintain a seal between the valve member and the cannula that can substantially prevent the passage of liquids. In some embodiments, the inner diameter of the cavity 4035 at the base 4056 of the valve can be substantially the same as or greater than the outer diameter of the cannula 4087 at the top of the cannula. In some embodiments, the valve can be inserted over the cannula until a bottom surface 4058 of the valve contacts the top surface 4021 of the inner body 4020.

In some embodiments the bulging sections 4034 can have local maximum outer diameters $OD_{404}$ that can fit within the interior space 4069 of the outer body 4010 without the valve member 4030 being compressed from an first state. In some embodiments, the bulging sections can have outer diameters such that for the valve to fit within the first housing, the bulging sections 4034 are compressed at least partially by an interior wall 4114 of the housing.

Also visible in FIG. 25 is the arrangement of the valve member 4030 within the outer body 4010. In some embodiments, the valve member does not have a lip that seats within a ledge in the Luer connector region 4040 as in various embodiments discussed above. This can allow the valve member to be pressed into the outer housing, and in some embodiments out of the Luer connector region 4040 entirely, when a medical device is connected to the medical connector. Additionally, the valve member 4030 and interior surfaces of the outer body 4010 can be configured to align with each other, thereby helping minimize the size of the connector and unnecessary space within the connector. For example, interior surfaces 4015 can be angled at approximately the same amount as the outer surface 4148 of the angled segments 4039 of the valve member 4030. This can allow the valve and interior surfaces of the outer housing to be positioned substantially flush with each other when the medical connector is assembled. This can also help prevent the valve from being removed from the medical connector. Similarly, a downward facing interior surface 4015' can be positioned over the base 4056 of the valve, helping keep the valve in position within the medical connector.

Figure 26:
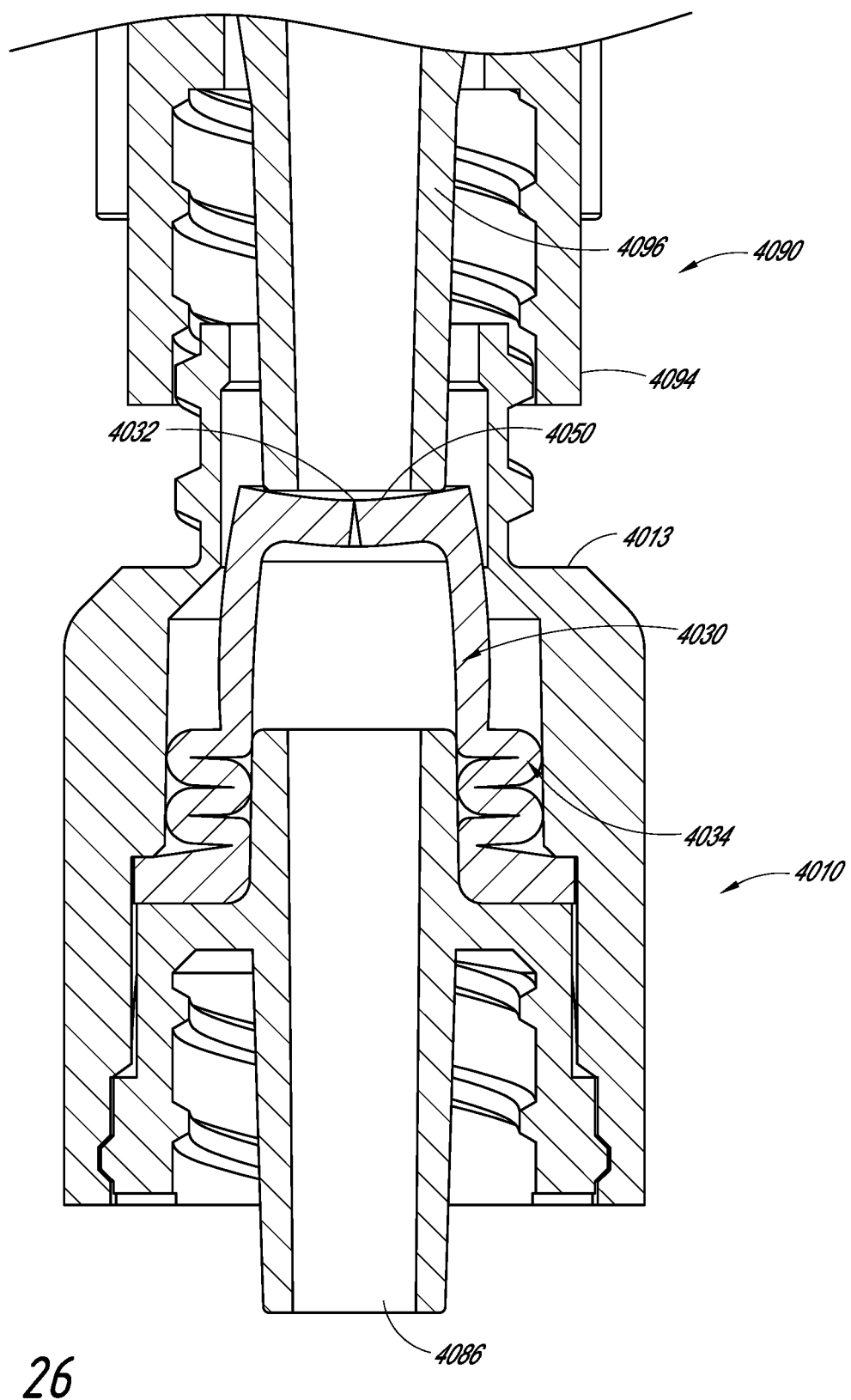
FIG. 26 is a cross-sectional view of the medical connector of FIG. 24 when partially connected to a medical device.
Figure 27:
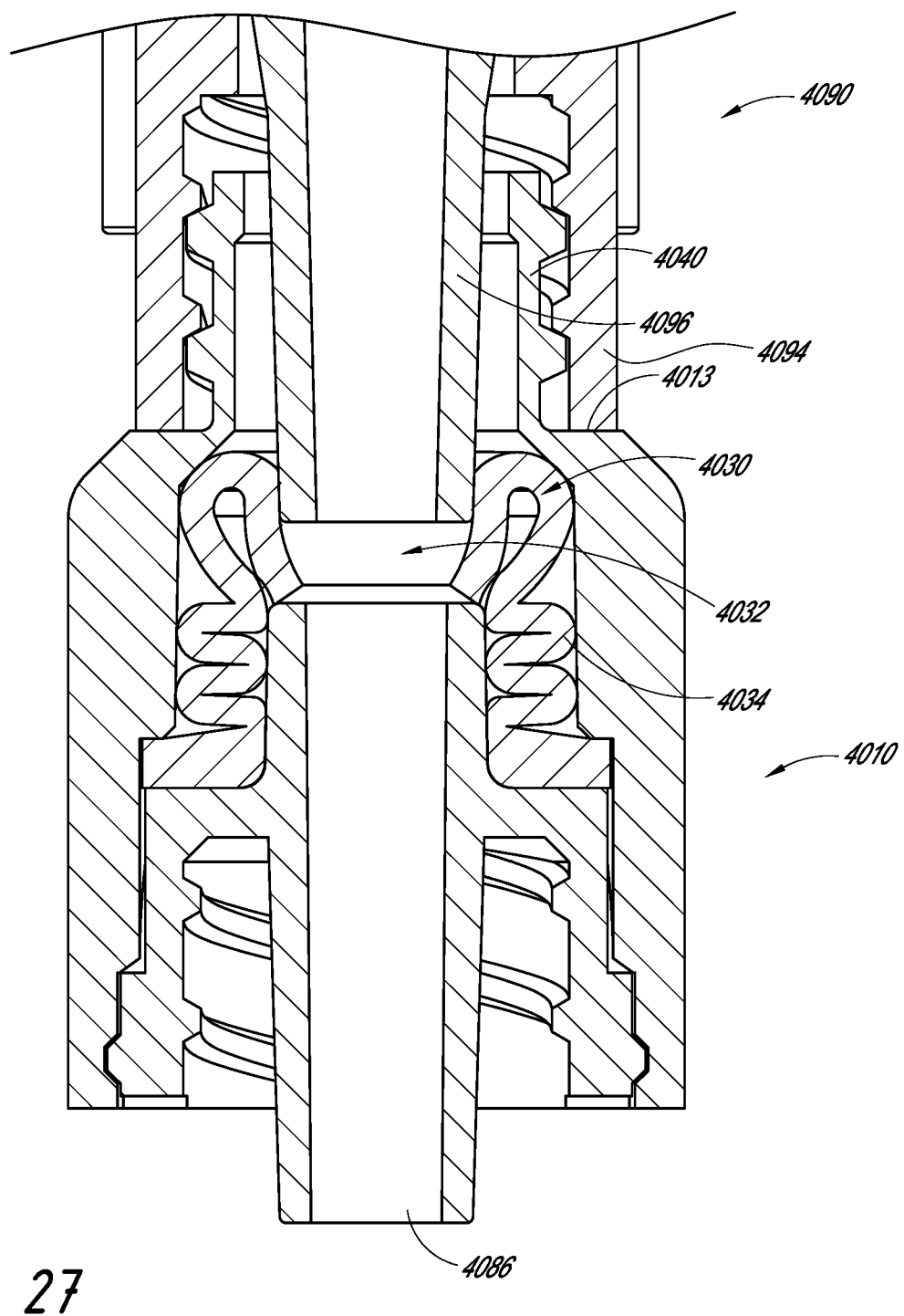
FIG. 27 is a cross-sectional view of the connector of FIG. 26, when fully connected to a medical device.

FIGS. 26 and 27 illustrate cross-sectional views of the medical connector 4001 of FIGS. 24 and 25 as it is being attached to a medical device 4090. FIG. 26 illustrates the medical connector when it is partially attached to the medical device and FIG. 27 illustrates the medical connector when it is fully attached to the medical device. In FIG. 26, it can be seen that the Luer cannula 4096 of the medical device can assert a compressive force on the valve member 4030, pushing the valve member into a compressed position. This compressive force can cause the bulging sections 4034 to compress and fold against each other, thereby shortening the length of the valve, which can be pushed into the outer body 4010. In some embodiments, the width of the top section 4050 can be such that the slit 4032 does not completely open at this point, or in some embodiments has not yet begun to open.

The medical device can be inserted further, screwing into the top Luer connector region 4040, as discussed above with respect to FIGS. 13A and 13B. In some embodiments, the medical device can be inserted until the tip of the connection region 4094 of the medical device 4090 contacts and is braced against the upper surface 4013 of the outer body 4010. At this point, the Luer cannula 4096 of the medical device 4090 can have extended almost all the way to the Luer cannula 4086 of the inner body 4020. The Luer cannula 4096 can also have advanced far enough to completely open the slit 4032 of valve member 4030, creating a clear and direct flow path between the two cannulas.

Tego Tab

Figure 28:
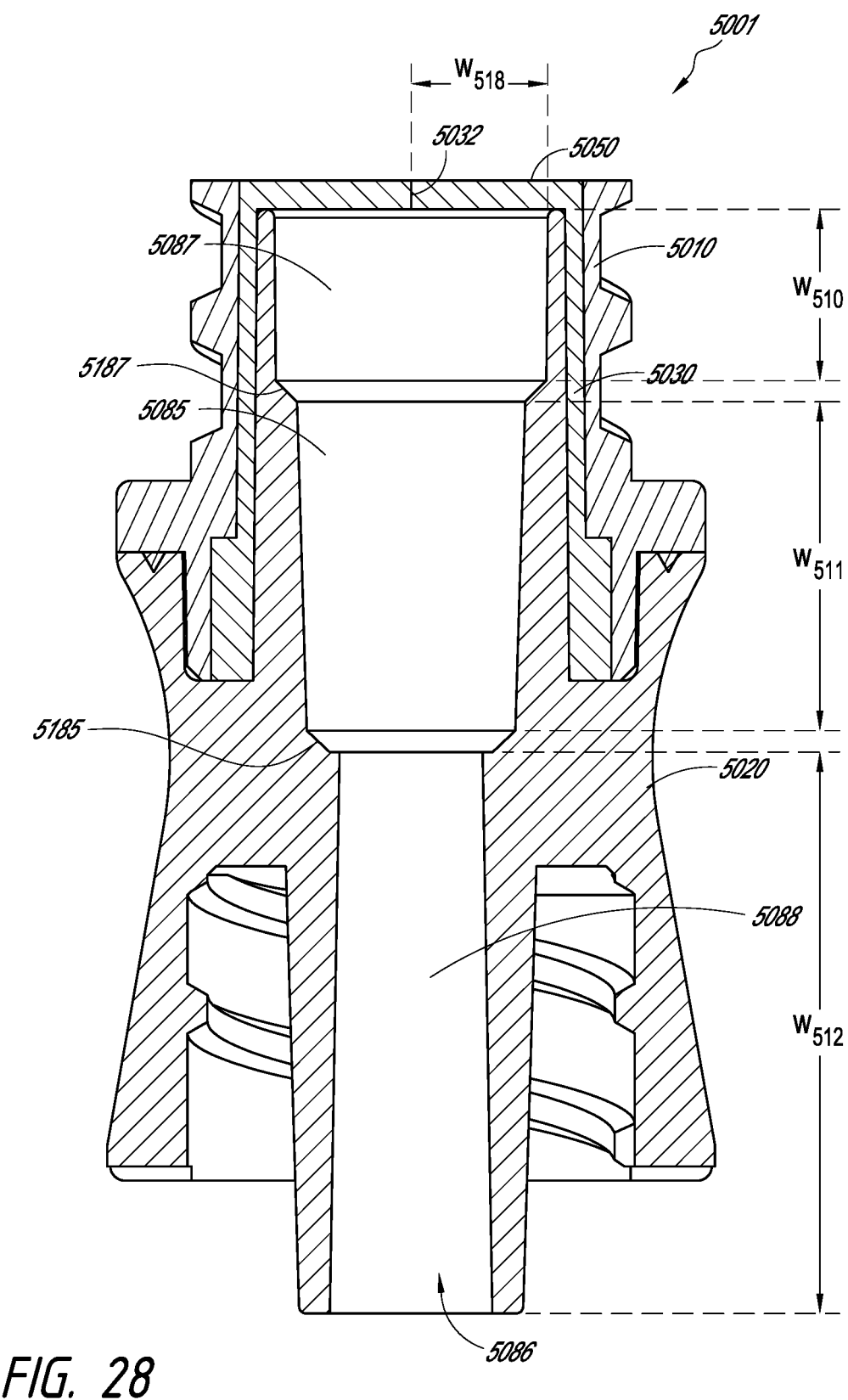
FIG. 28 is a cross-sectional view of one embodiment of a medical connector.
Figure 29:
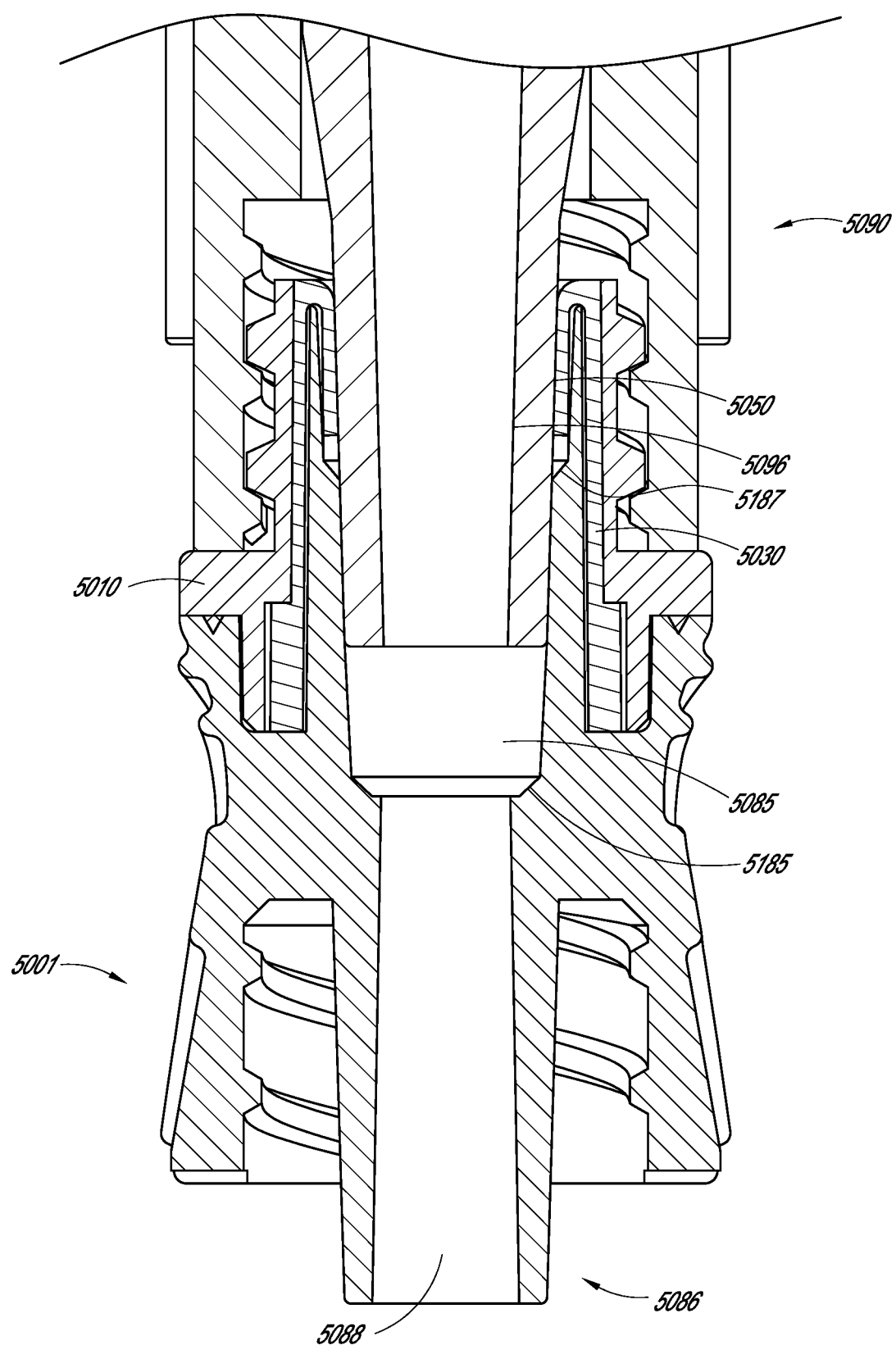
FIG. 29 is a cross-sectional view of the medical connector of FIG. 28 when connected to a medical device.

FIGS. 28 and 29 illustrate one embodiment of a medical connector 5001. In various embodiments the medical connector can have any of the features or aspects of the embodiments discussed above. FIG. 28 is a cross-sectional view of the medical connector when fully assembled. As above, the medical connector can include a first housing 5010, a second housing 5020, and a valve member 5030. Also as above, the valve member can have a top 5050 with a slit 5032 that extends through the top and into a cavity within the valve. In some embodiments, the Luer cannula 5086 of the second housing 5020 can extend into the valve 5030 and all the way to a lower surface of the valve top 5050, as illustrated. The valve top on each side of the slit 5032 can have a width $w_{518}$ measured from the slit to the Luer cannula 5086.

In some embodiments, the inner diameter of Luer cannula 5086 can vary along the cannula's length. In some embodiments, the Luer cannula 5086 can have a lower section 5088, a middle section 5085, and an upper section 5087. In some embodiments, each section can connect to the other by a tapered section. For example, in some embodiments an upper tapered section 5187 can connect the upper section 5087 to the middle section 5085. In some embodiments, a lower tapered section 5185 can connect the middle section 5085 to the lower section 5088. Each section can have a constant or a varying inner diameter, and in some embodiments the upper section 5087 can have at least one inner diameter that is larger than any inner diameter of the lower section 5088 or the middle section 5085. In some embodiments, the middle section 5085 can have at least one inner diameter that is larger than an inner diameter of the lower section 5088 of the Luer cannula 5086.

In some embodiments, some sections can have a constant inner diameter while others can have a variable inner diameter. Further, in some embodiments the inner diameter of different sections can vary in different directions. For example, in some embodiments the upper section 5087 can have a generally constant inner diameter or an inner diameter that decreases from the top of the upper section toward the bottom of the upper section; the middle section 5085 can have an inner diameter that decreases from the top of the middle section toward the bottom of the middle section; and the lower section 5088 can have an inner diameter that increases from the top of the lower section toward the bottom of the lower section.

The upper section 5087 can have a height $h_{510}$, the middle section 5085 can have a height $h_{511}$ and the lower section 5088 can have a height $h_{512}$. In some embodiments, the height $h_{510}$ of the upper section can be less than the height $h_{511}$ of the middle section, which can be less than the height $h_{512}$ of the lower section. In some embodiments, the different sections can have different relative heights or can have equal heights.

FIG. 29 illustrates an embodiment where a medical device 5090 has been inserted into the medical connector 5001. The middle section 5085 of the Luer cannula 5086 of the second housing 5020 can have an inner diameter that corresponds to an outer diameter of the Luer cannula 5096 of the medical device 5090 such that the Luer cannula 5096 can fit tightly within the middle section 5085. If the outer diameter of the Luer cannula 5096 of the medical device 5090 varies, the inner diameter of the middle section 5085 can vary accordingly. For example, if the Luer cannula 5096 of the medical device 5090 has a taper, the middle section 5085 can have an increasing diameter from bottom to top that increases at the same rate the Luer cannula 5096 of the medical device 5090 tapers. This correspondence can create a tight fit between the two luers, allowing them to mate without having undesired leakage of fluids passing through the luers. Having the two luers join directly can also establish more direct flow paths between medical devices attached to each end of the medical connector 5001.

When the Luer cannula 5096 of the medical device 5090 is attached to the medical connector 5001, it can push through the slit, separating each side of the top 5050 of the valve member and folding the sides downward. Because any inner diameter of the upper section 5087 can be greater than an inner diameter of the middle section 5085, in some embodiments there can be space for each side of the top 5050 of the valve member 5030 to fit between the Luer cannula 5096 of the medical device 5090 and an inner surface of the upper section 5087 of the Luer cannula 5086, as illustrated in FIG. 29. In some embodiments, the height $h_{510}$ of the upper section 5087 can be greater than the width $w_{518}$ of each side of the valve top 5050, which can help ensure that each side of the valve top is not too long to fit into the available space.

The inner diameter of the upper section 5087 can be configured such that the gap between the Luer cannula 5096 of the medical device 5090 and the inner walls of the upper section 5087 remains at a generally constant value that is approximately equal to the thickness of the top 5050 of the valve member 5030. In some embodiments the width of the gap can vary, and in some embodiments it can be less than the thickness of the top, such that the top must compress to fit within the gap. This can create greater friction between the Luer cannula 5096 and the top 5050, such that when the cannula is removed it can pull the valve top 5050 up with it, helping return the valve top to its initial position of FIG. 28.

Four Piece Embodiment

Figure 30:
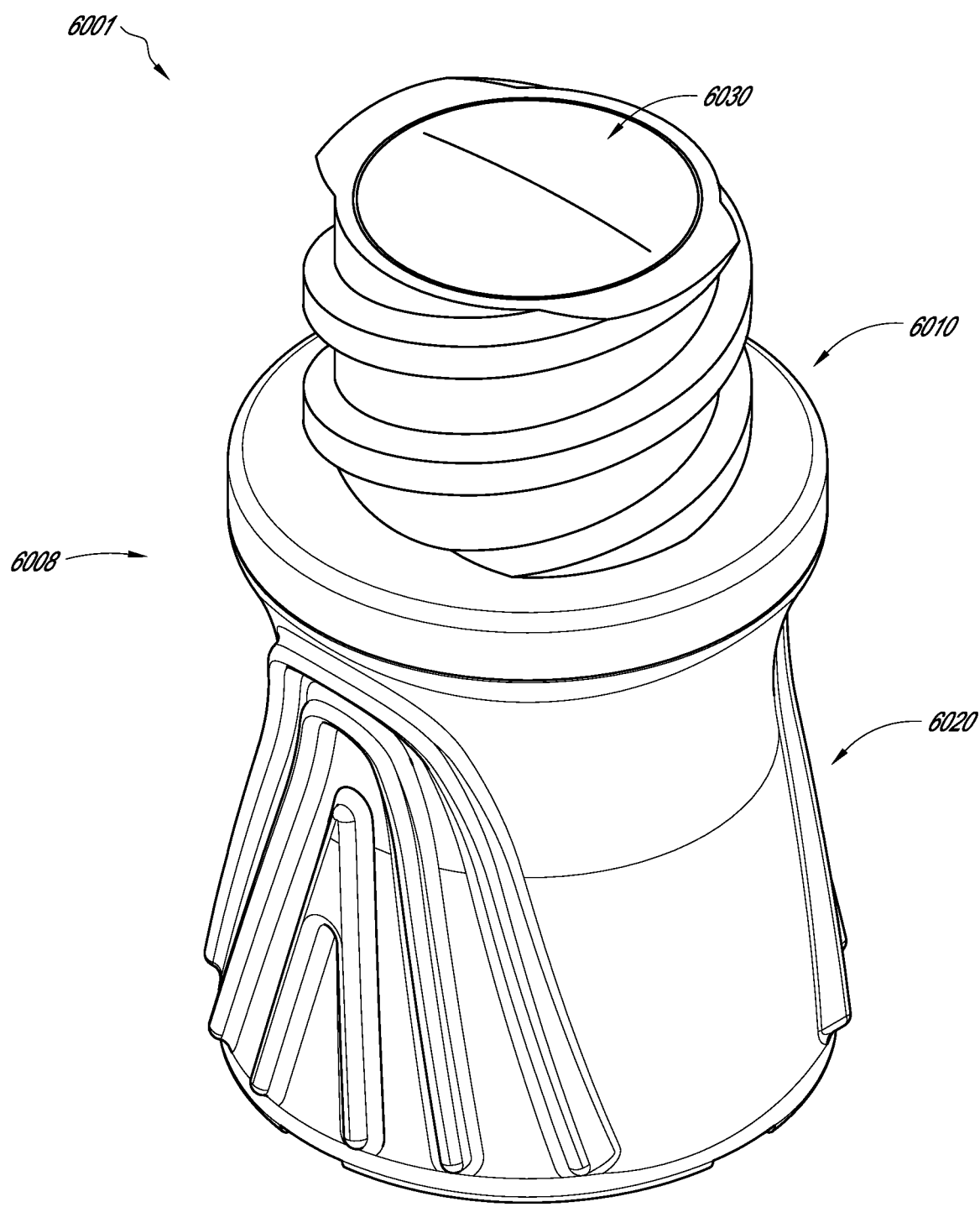
FIG. 30 is a perspective view of one embodiment of a medical connector.

FIGS. 30-32B illustrate one embodiment of a medical connector 6001. As seen in FIG. 30, the housing 6008 can be substantially the same along its outer surfaces as the housing described with respect to FIG. 14. Unless otherwise indicated, the medical connector 6001 can be the same as embodiments with valve member inserts discussed above.

FIGS. 31A and 31B illustrate cross-sectional views of the valve member 6030 taken at approximately 90 degrees from each other. As in previous embodiments, the valve member can comprise a slit extending from a top 6050 of the valve member 6030 to an internal cavity 6035, which can ultimately join with a lead lumen 6036. In some embodiments, the internal cavity 6035 and lead lumen 6036 can extend to a position short of the bottom of the valve 6030, as illustrated. In some embodiments, the internal cavity 6035 does not extend all the way across the valve (as illustrated in FIG. 31B). This can allow for an outer cavity 6035' that can extend around at least a portion of the lead lumen 6036 and the internal cavity 6035. In some embodiments, the lead lumen can have an annular projection 6057 along an interior surface thereof, which can be configured to mate with a recess in a second housing, as discussed below.

Figure 32:
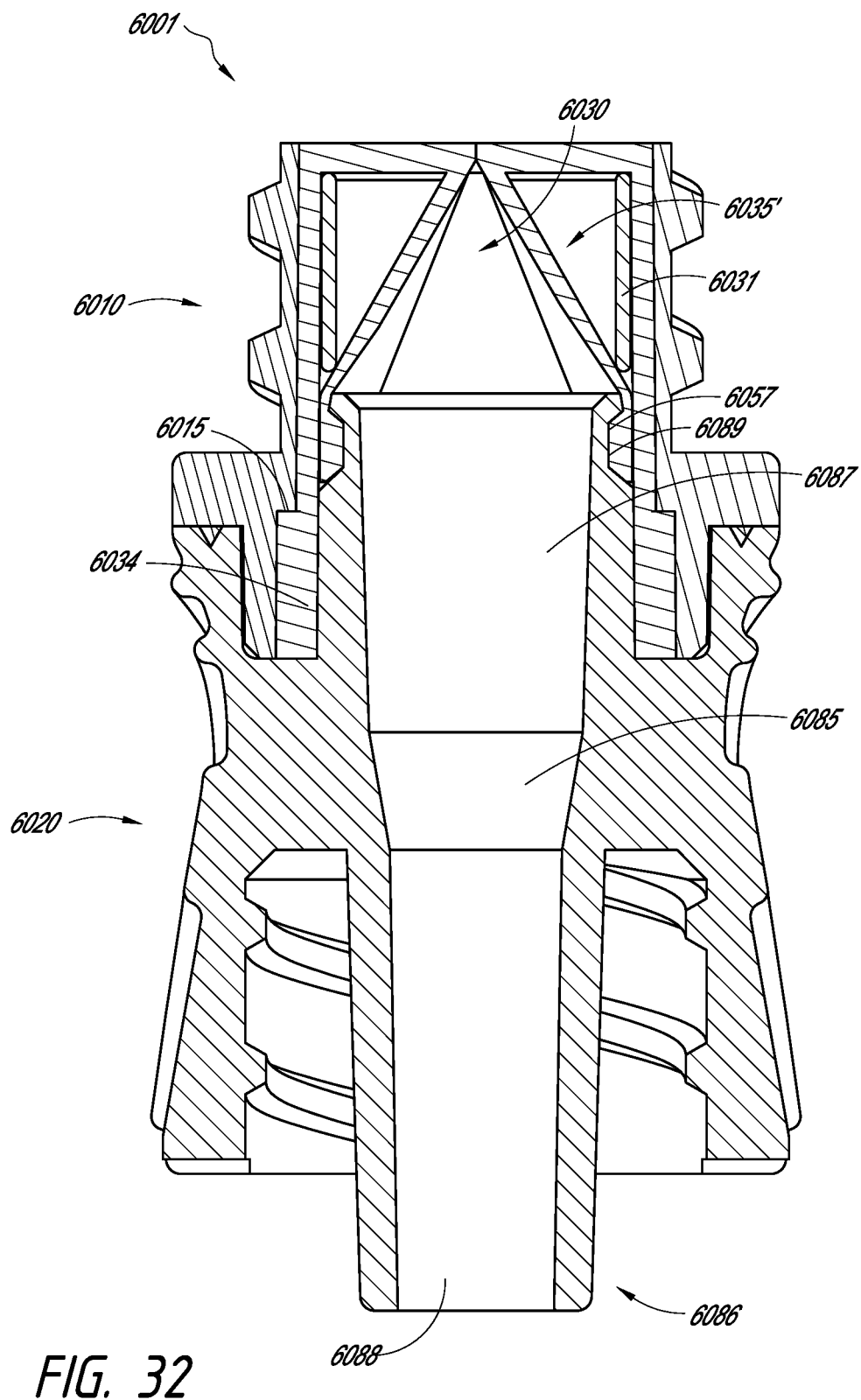
FIG. 32 is a cross-sectional view of the medical connector of FIG. 30.

FIG. 32 is a cross-sectional view of the connector 6001 when fully assembled. The Luer cannula 6086 of the second housing 6020 can have a lower section 6088 and an upper section 6087 that extends up and into the first housing 6010. In some embodiments, the cannula can have a middle section 6085 joining the upper and lower sections. The upper, middle, and lower sections can vary in height and inner diameter according to the various embodiments described above with respect to FIGS. 28 and 29. Similarly, in some embodiments the cannula 6086 can be configured such that a cannula (not shown) of a medical device attached to the first housing 6010 can fit within the cannula 6086 of the second housing 6020, as discussed above. In some embodiments, the cannula of the medical device can extend to the lower section 6088 or only as far as the middle section 6085 or the upper section 6087.

In some embodiments, an insert 6031 can be positioned within the outer cavity 6035' of the valve member and around at least a portion of the internal cavity 6035 and/or the lead lumen 6036. In some embodiments, the valve member 6030 can be molded around the insert 6031. In some embodiments, the valve insert can be a substantially cylindrical section, or it can be a ring with varying cross sections. The valve insert can help provide structural support to the valve element.

As in various embodiments described above, the lead lumen 6036 can be stretched around the Luer cannula 6086 when the connector 6001 is fully assembled. In embodiments where the internal cavity 6035 and lead lumen 6036 extend to a position short of the bottom of the valve 6030, as illustrated, the Luer cannula can be sized and configured to extend into the valve in order to reach the lead lumen. The lead lumen can then be positioned around the cannula with the help of an insertion device, as described above.

In some embodiments, the device can be configured such that the valve element 6030 must be stretched downward to reach the cannula, although in some embodiments it does not need to be stretched to reach the cannula. In some embodiments, the external surface of the upper portion 6087 of the cannula 6086 can have an annular recess 6089 that can mate with an annular projection 6057 of the lead lumen 6036. This can help maintain the lead lumen in position. The valve member 6030 can also include a shoulder 6034 that can snap into position beneath a lower ledge 6015 of the first housing 6010, further helping maintain the valve in position.

Molding

As discussed above, in some embodiments the valve members and first housings discussed herein can be formed as part of a two-shot injection molding process. The following provides a brief description of that process and of various components that can be used as part of a molding assembly. The description provided is with respect to the valve and housing of FIG. 2, but the same techniques can be applied to any embodiments discussed herein.

Figures 33A, 33B:
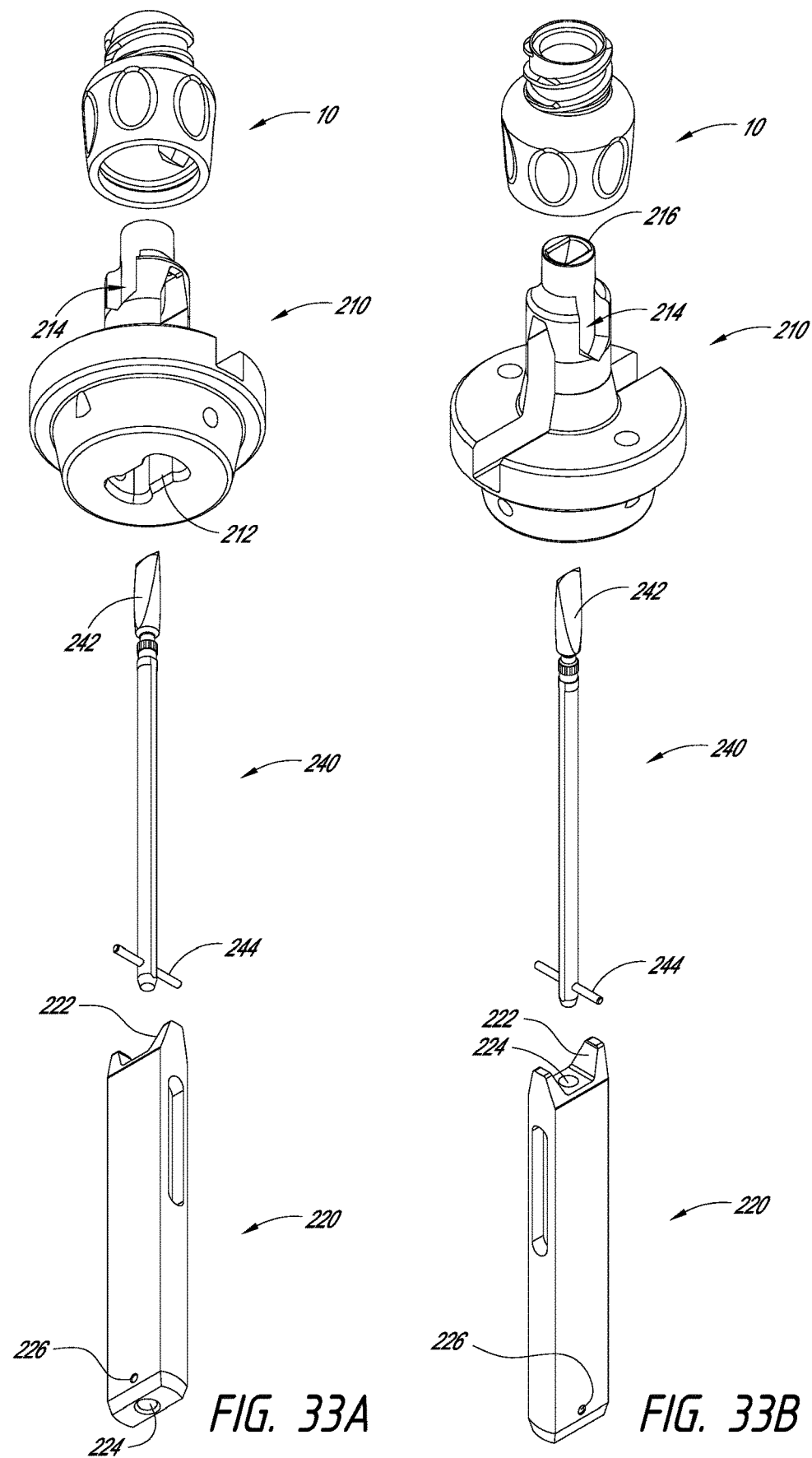
FIG. 33A is a bottom perspective exploded view of one embodiment of various elements used to mold a medical connector.
FIG. 33B is a top perspective exploded view of the elements of FIG. 33A.

FIGS. 33A and 33B illustrate exploded views of various components of a molding assembly. FIG. 33A provides a bottom perspective view and FIG. 33B provides a top perspective view. Illustrated are a first sleeve 210, a second sleeve 220, a core pin 240, and a housing 10. The housing is formed first as part of the two-shot injection molding process, described below, and is illustrated for purposes of explaining the molding of the valve, which is formed within the housing.

In some embodiments, the first sleeve 210 can have a sleeve access opening 212 and a projection cutout 214. The second sleeve 220 can be sized and configured to fit into the sleeve access opening 212. An upper end of the second sleeve can have a valve base projection 222, which can help define the base of the valve when it is molded, as discussed in more detail below.

The second sleeve can also have a central lumen 224 that can be configured to receive the core pin 240. In some embodiments, the second sleeve can further have a transverse lumen 226, which can be configured to receive a cross bar 244 of the core pin. The cross bar can help maintain the position of the core pin within the second sleeve, and can also be used to define the location of both the first and second sleeves relative to other components of the mold assembly, as discussed below.

In some embodiments, the exterior surface of the first sleeve 210 can define at least a portion of the interior surface of the first housing 10 when the first housing is molded. Thus, the projection cutouts 214 can define the downward projections 60 within the first housing (discussed with respect to FIG. 6). Similarly, the interior surface of the first sleeve can define at least a portion of the exterior surface of the valve member 30 when it is molded. In some embodiments, the first sleeve 210 can be configured such that the downward projections of the first housing are in a plane substantially perpendicular to the shoulders 34 of the valve.

In some embodiments, the second sleeve 220 can define at least a portion of the exterior surface of the valve member 30 when it is molded. For example, in some embodiments the valve base projection 222 can define the bottom 58, the side surface 138, and/or the chamfer 139 (all visible in FIG. 4A) of the valve.

In some embodiments, the core pin 240 can define at least a portion of the interior of the valve member. In some embodiments, cavity section 242 can define the internal cavity 35 of the valve and at least a portion of the slit 32 (both visible in FIG. 4A). In some embodiments the cavity section 242 can define the entire slit of the valve. In some embodiments, the core pin can also define the tapering section 137 and the lead lumen 36 of the valve (also visible in FIG. 4A).

Figure 34:
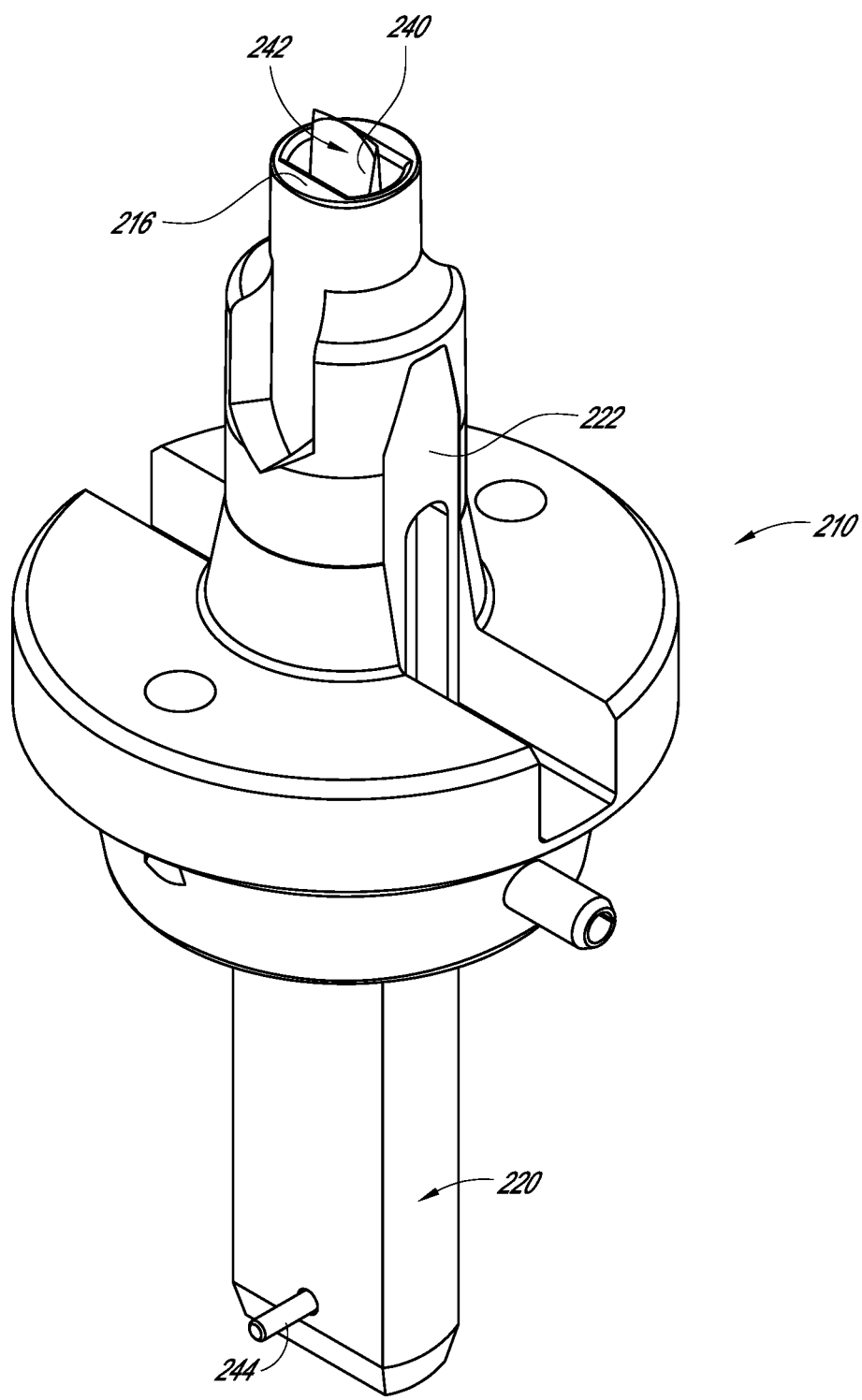
FIG. 34 is a top perspective view of one embodiment of elements used to mold a medical connector.

FIG. 34 illustrates the first sleeve 210, the second sleeve 220, and the core pin 240 as assembled according to some embodiments. As visible in FIG. 34, the core pin can have a cavity section 242 that extends past a top surface 216 of the first sleeve. In some embodiments, the first housing 10 can be molded such that it extends above the top surface of the first sleeve as well. In such embodiments, when material is injected into the first sleeve 10 to form the valve, it too can extend above the top surface 216, allowing it to directly contact the first housing.

Figure 35A:
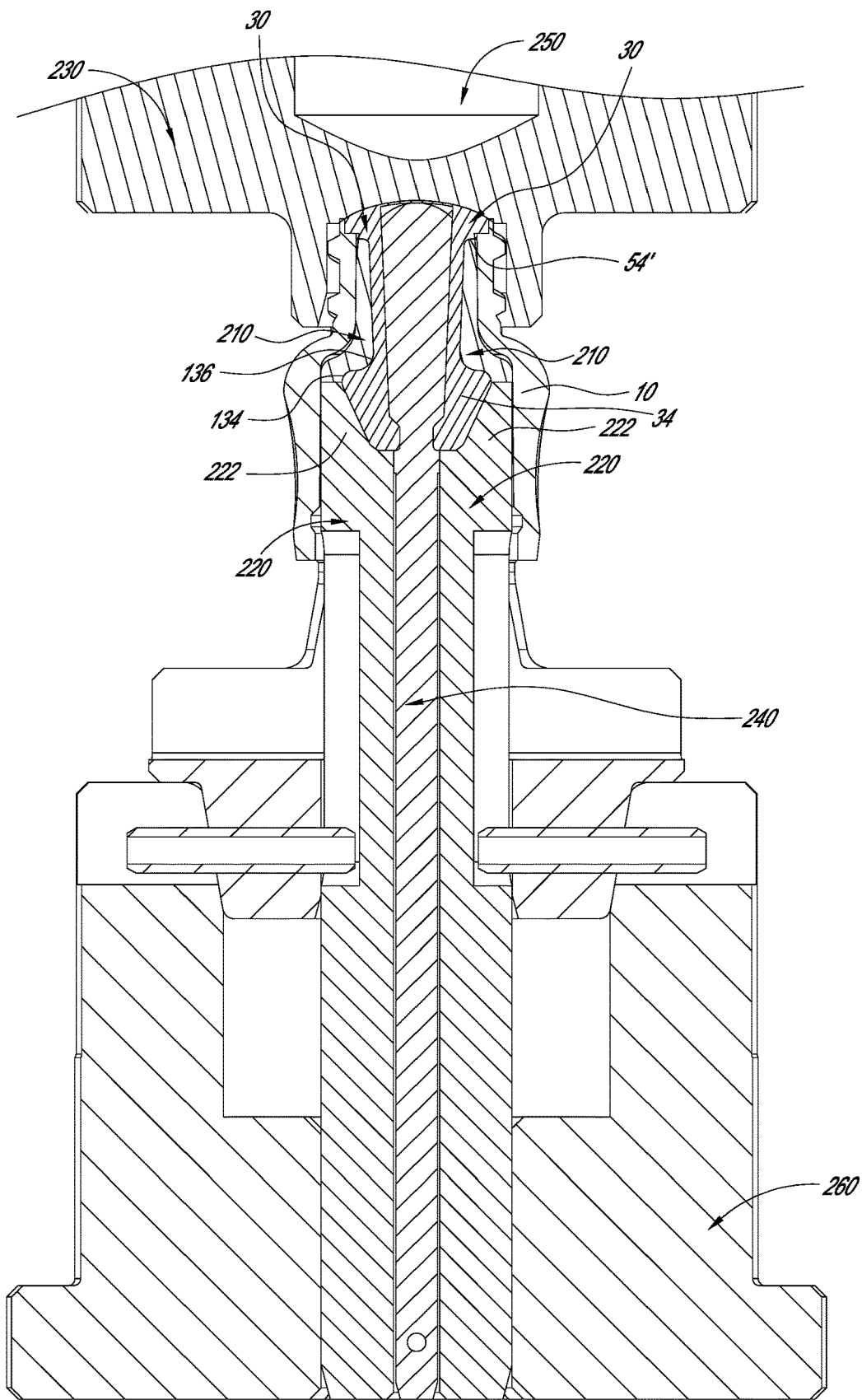
FIG. 35A is a cross-sectional view of one embodiment of elements used to mold a medical connector.
Figure 35B:
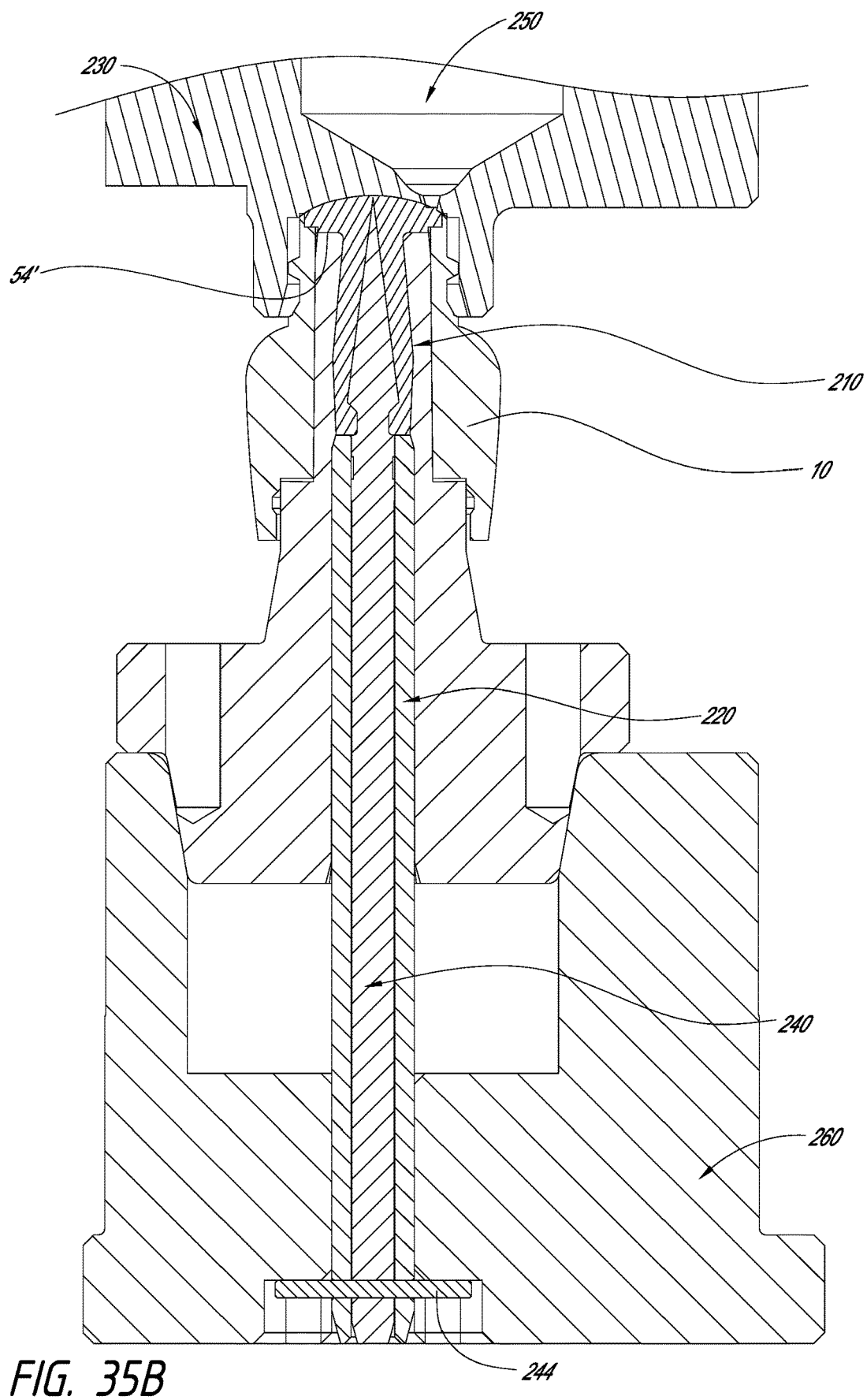
FIG. 35B is a cross-sectional view of the elements of FIG. 35A, taken at about 90 degrees relative to the cross-section of FIG. 35A.

FIGS. 35A and 35B illustrate cross-sectional views of the molding components described thus far when assembled, and also illustrate some additional components used in an entire assembly. FIG. 35A is a cross-sectional view taken in the plane of shoulders 34 of the valve member 30, and FIG. 35B is a cross-sectional view taken in a plane rotated approximately 90 degrees from the plane of FIG. 35A. In both FIGS. 35A and 35B the valve member 30 and housing 10 have already been molded.

In some embodiments, a molding assembly can include a base 260 that surrounds at least a portion of the first sleeve 210 and/or the second sleeve 220. As illustrated in FIG. 35B, in some embodiments the cross bar 244 can be used to block motion of the first sleeve 210 and/or the second sleeve 220 relative to the base, in at least one direction. This can help ensure that the various components of the molding assembly are properly aligned, and that the valve member 30 and first housing 10 are properly aligned with each other when molded.

In some embodiments, a molding assembly can include a top section 230. The top section can define a top of the valve member 30 when it is molded. The top section can be sized and shaped to define the top of the valve member according to the various embodiments discussed herein. In some embodiments, the top section can also include an injector 250. As illustrated in FIG. 12A, in some embodiments the injector is not centered on a central axis of the valve member 30, such that in some cross sectional views of the valve member the injector does not reach the bottom of the top section.

For the sake of clarity, FIGS. 35A and 35B do not illustrate all of the sections of a molding assembly that would define the outer surfaces of the first housing 10. The section(s) that are not illustrated can be configured according to standard injection molding techniques and can be sized and shaped to define the first housing according to the various embodiments described herein.

As described above, the molding process can include a first step of injection molding a first housing 10. The first housing can be molded with a first material. The molding process can then include a step of injection molding the valve member 30. In some embodiments the valve member can be molded with a second material different than the first material. The materials of the first housing and the valve member can be selected so that the valve member adheres to the surfaces of the first housing that it may contact during molding.

FIGS. 35A and 35B make apparent how, in some embodiments, at least a portion of the valve member 30 can directly contact the housing when the valve member is molded. For example, as illustrated in both figures the very top of the first sleeve 210 may not extend to the top of where the first housing 10 is molded. Thus, as illustrated, when the valve is molded the top of the first sleeve can define the bottom surface 54' of the lower lip of the valve, and the first housing and top section 230 can define the exterior surfaces of the valve member above that point.

Once the valve member has been molded, it can be useful to remove certain components of the molding assembly in a certain order in order to be able to prevent damage to the valve member. For example, with particular reference to the embodiment illustrated in FIG. 35A, the core pin 240 can be removed first. This can open the interior of the valve member, allowing the valve member to flex inward for removal of other components. Next, the second sleeve 220 can be removed. In some embodiments, the core pin and second sleeve can be removed simultaneously.

Once the core pin 240 and second sleeve 220 have been removed, the first sleeve 210 can be removed from its position around the valve member. In order for the first sleeve 210 to fit around the shoulders 34 of the valve member in the illustrated embodiment, the first sleeve will need to compress the valve and/or push the shoulders 34 in toward the center of the valve. In some embodiments, the valve can be made from silicone, which does not compress well. In these embodiments, it can be advantageous to have the valve designed such that the interior cavity of the valve member is large enough to receive at least a portion of the shoulders when they are pushed inward, thereby allowing the first sleeve to pass. In some embodiments, the valve can be dimensioned to allow this process to occur. Some of these dimensions are discussed with reference to FIG. 4A, above.

Additionally, to ease removal of the first sleeve 210, in some embodiments the top surface 136 and the outer section 134 of the shoulder 34 can be rounded, as described above. The rounded sections can help the sleeve to push the shoulders inward, allowing the sleeve to pass, rather than catching on the shoulders and possibly tearing the valve. Once the core pin and sleeves have been removed, the housing 10 and valve member 30 can be removed.

The two-step injection molding process described herein can be used to mold a variety of parts, and is not limited to the housings and valves discussed thus far. The process can be particularly useful when molding a first part and then molding a second part within the first part. It can also be useful when the first part is rigid and the second part has varying width which may prevent a single sleeve from being used and withdrawn from around the second part without damaging the part.

Figure 36:
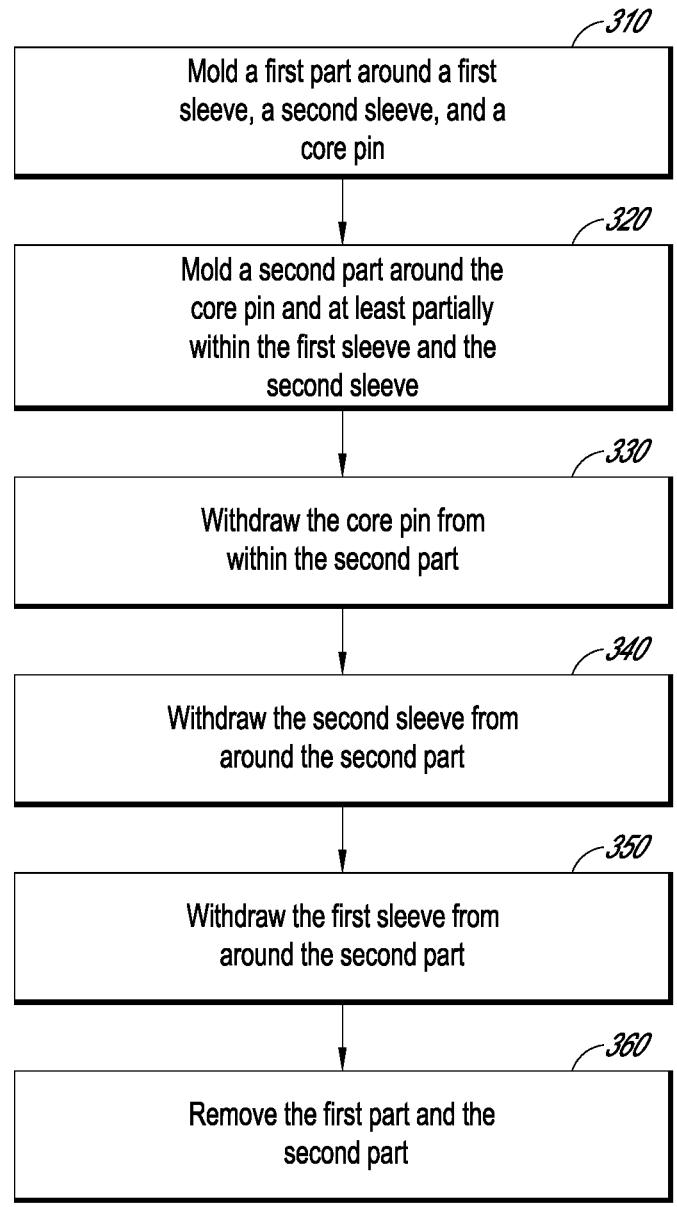
FIG. 36 is a flow chart of one embodiment of a two-step injection mold process.

FIG. 36 illustrates a flow chart of the steps used to perform a two-step injection molding process and then remove the molded components. In the first step 310, a first part is molded around a first sleeve, a second sleeve, and a core pin. In a second step 320, a second part can be molded around the core pin and at least partially within the first sleeve and the second sleeve. In some embodiments where the second part is not entirely within the first sleeve and the second sleeve, it can be configured to contact the first part.

Once both parts have been molded, in a third step 330 the core pin can be withdrawn from within the second part. In a fourth step 340, the second sleeve can be withdrawn from around the second part. In some embodiments, these steps can be performed in different orders or simultaneously. Once the core pin and second sleeve have been withdrawn, in a fifth step 350 the first sleeve can be withdrawn from around the second part. The first part and the second part can then be removed.

Catheters

The various medical connector embodiments described herein have certain features that allow them to be advantageous for a variety of different purposes. For example, in some embodiments a medical connector can be used as part of a catheter system. Such systems can be used to insert a catheter into a patient's vasculature and then provide a point of connection to access the catheter. Generally, a catheter system that has been assembled for use will include a catheter attached to one end of a connector (also described as a catheter hub) and a needle that runs at least partially through the catheter hub and the catheter. The needle can be used to pierce the patient's skin and enter the vasculature, providing access for the catheter to enter the vasculature as well. Once the catheter is positioned, the needle can be removed. A valve positioned within the catheter hub can prevent blood from flowing through the catheter and out of the catheter hub. The catheter hub can be configured to permit various medical implements to connect to the catheter hub.

Generally, a catheter system is sold with a needle running at least partially through the catheter hub (including the valve) and the catheter so that a clinician does not have to feed the needle through both components before inserting the catheter. This can take time and risks accidentally sticking the catheter wall with the tip of the needle. One potential problem, however, is that if a needle is within the valve in the catheter hub for too long, such as if a catheter system is in the shelf in a medical facility for an extended period of time before use, a compression set can occur around the needle. This is when valve loses at least some of its ability to return to a closed position once the needle is removed, allowing blood or other fluid to escape from the catheter hub.

Because various embodiments of medical connectors described herein include a valve member that can have a first, generally relaxed state and a second state of greater tension, such medical connectors can provide an advantage when serving as catheter hubs. In particular, they can be stored in the first state in which the valve is in a less tensioned state along a vertical axis relative to the second state. Thus, in some embodiments of various catheter assemblies disclosed and contemplated herein, the catheter assemblies can have a first stage with the valve in a first state and a second stage with the valve in a second state. In some embodiments, once a catheter has been properly inserted in a patient's vasculature, the catheter assembly can be transitioned to the second stage. This can help seal the valve member and preclude or limit any compression set from allowing blood to flow through the valve member.

In some embodiments, a catheter assembly can be transitioned to the second stage at a time prior to insertion of the catheter into the vasculature. In some embodiments, the catheter assembly can be transitioned to the second stage immediately prior to inserting the catheter into the vasculature. In some embodiments, the catheter assembly can be transitioned to the second stage as the catheter is being inserted into the vasculature. In some embodiments, the catheter assembly can be transitioned to the second stage as the insertion needle is being removed from the vasculature after the catheter assembly is placed therein. In some embodiments, the transition from the first stage to the second stage happens automatically as the catheter assembly is being inserted or portions are being withdrawn, or after portions are withdrawn. In some embodiments, the transition from the first stage to the second stage requires manual manipulation of the catheter assembly.

Figure 37A:
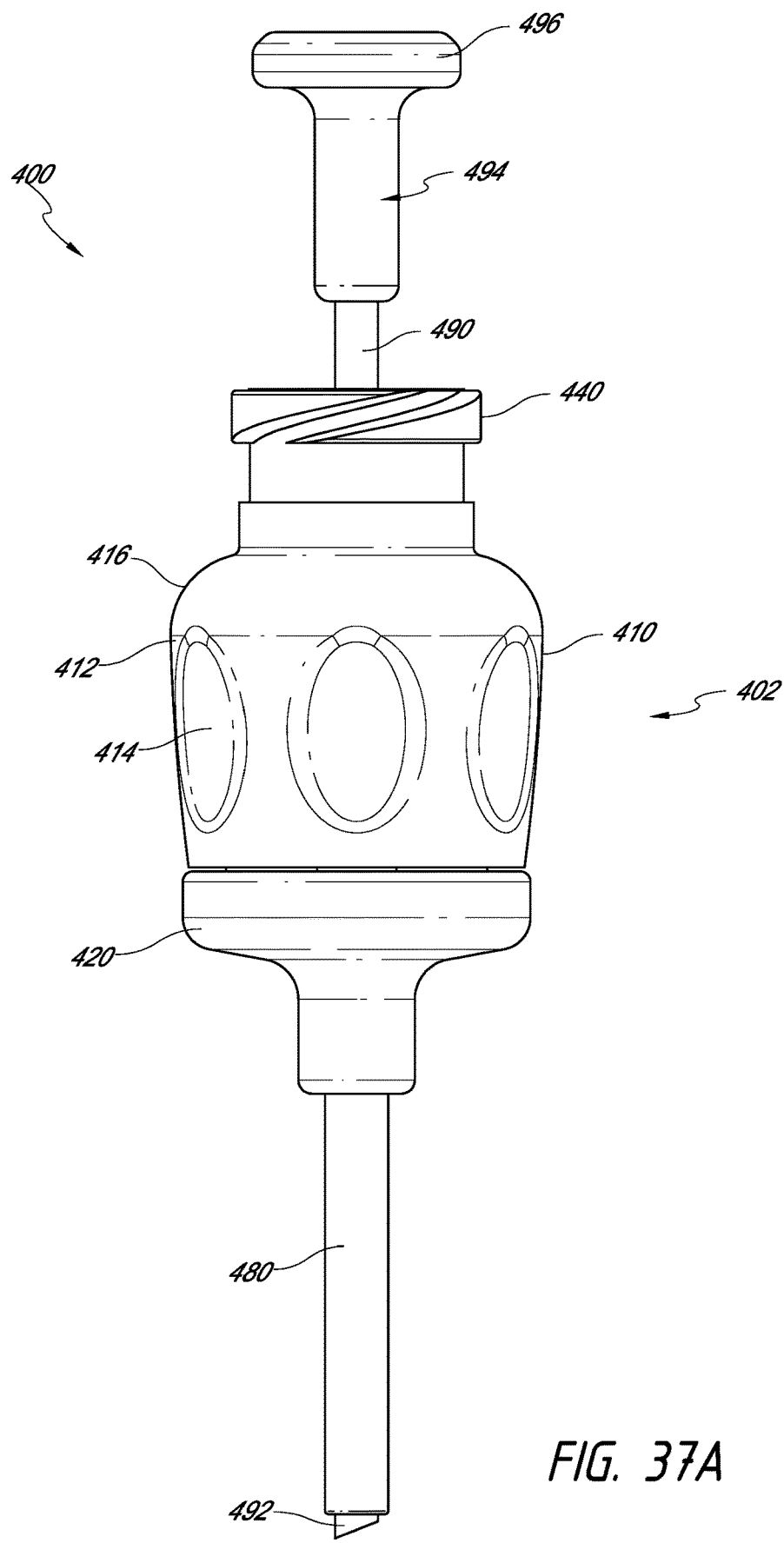
FIG. 37A is a front view of one embodiment of a catheter assembly in a first stage.
Figure 37B:
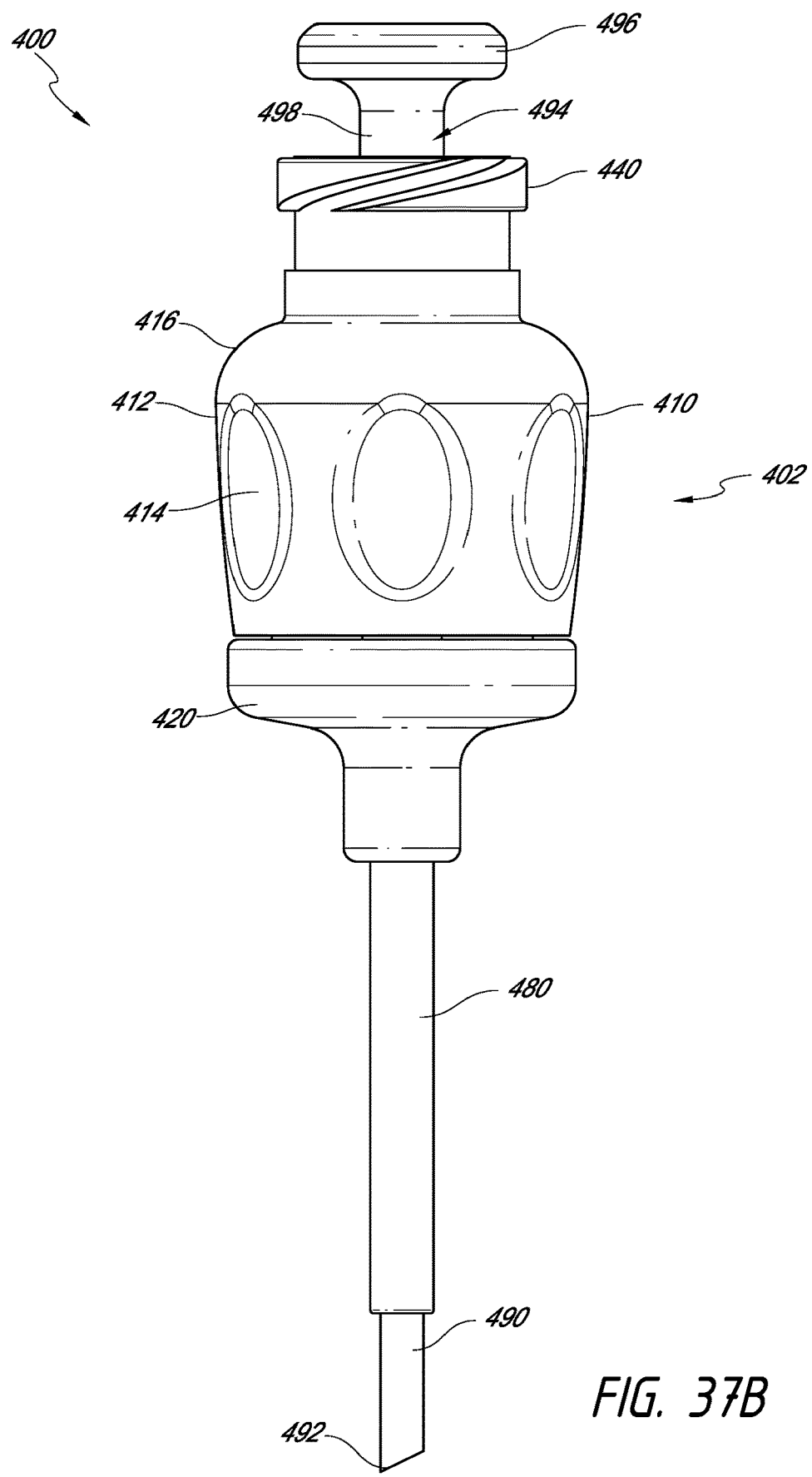
FIG. 37B is a front view of the catheter assembly of FIG. 37A in a second stage.

FIGS. 37A and 37B illustrate one embodiment of a catheter system or assembly 400. The catheter assembly can include a connector or catheter hub 402, which can operate according to various embodiments of connectors described herein. Although not all aspects of the catheter hub that are labeled may be specifically described, and not all aspects of the catheter hub are labeled, it is understood that unless described otherwise, features similarly numbered or illustrated as in previous embodiments will operate in a similar manner as previously described.

The catheter hub 402 can include a housing that includes a first housing 410 attached to a second housing 420. As described above, an outer surface 412 of the first housing can include a variety of surface features 414, such as dimples, that can be used to improve the comfort of an operator or clinician when grasping the catheter hub, and/or which can be used to increase the ability of an operator or clinician to maintain a grip on the housing. Also as described above, the first housing 410 can include an upper connector region 440 that can be used to attach the catheter hub to a medical implement. This is generally done once the catheter has been appropriately positioned within a patient. As described above, any ANSI connection can be used, and in some embodiments non-standard connections can be used.

A needle 490 can pass through the catheter hub 402 and into a catheter 480 that is attached to and extends from the catheter hub. In various embodiments the catheter can have different lengths depending on the desired or expected use for the catheter. In some embodiments, a needle hub 494 can be attached to the needle at a proximal end of the needle. As used herein, "proximal" refers to the end that is closest to a clinician working with the catheter assembly. As illustrated, proximal is analogous to "upper" as defined with respect to FIG. 1.

The needle hub can include an insertion section 498 and in some embodiments can have a manipulation feature 496. The manipulation feature can be used to provide an improved grip for a clinician or practitioner when manipulating the needle. As illustrated, the manipulation feature can be a handle or lever, but it can have a variety of forms, including dimples, longitudinal ribs, lateral ribs, channels, roughened sections, or any other similar feature.

The catheter assembly 400 is preferably initially provided in the position as shown in FIG. 37A, such that a distal tip 492 of the needle 490 is in a non-insertion position, approximately even with the end of the catheter 480. In some embodiments, a needle in a non-insertion position can extend just past the end of the catheter, or just inside the catheter. In some embodiments in the non-insertion position, an insufficient amount of the needle is exposed in order to be able to properly insert the needle into a patient's vasculature. Thus, in order to sufficiently expose the needle to be able to insert it into the vasculature of a patient, in some embodiments a clinician must first move the needle further through the catheter hub 402 to an insertion position, in which the needle can be inserted into a patient. The exact positioning of the needle hub 494 can vary when initially provided, and in some embodiments the needle hub can be positioned adjacent the catheter hub 402 such that the needle is not visible between the catheter hub and the needle hub. In some embodiments, the needle hub can be positioned partly within the catheter hub. In some embodiments, the needle hub can be positioned far enough into the catheter hub such that the proximal tip of the needle 490 is within the catheter hub.

FIG. 37B illustrates the same view as 37A, but after a clinician has moved the needle further through the catheter hub 402 according to some embodiments. Preferably, the needle 490 and needle hub 494 are configured and positioned such that to expose a sufficient amount of the needle and/or its tip 492 in order to properly access a patient's vasculature, the insertion section 498 of the needle hub will enter the valve member of the catheter hub. In some embodiments, the insertion section can move the catheter assembly into the second stage, as described below.

Figure 38A:
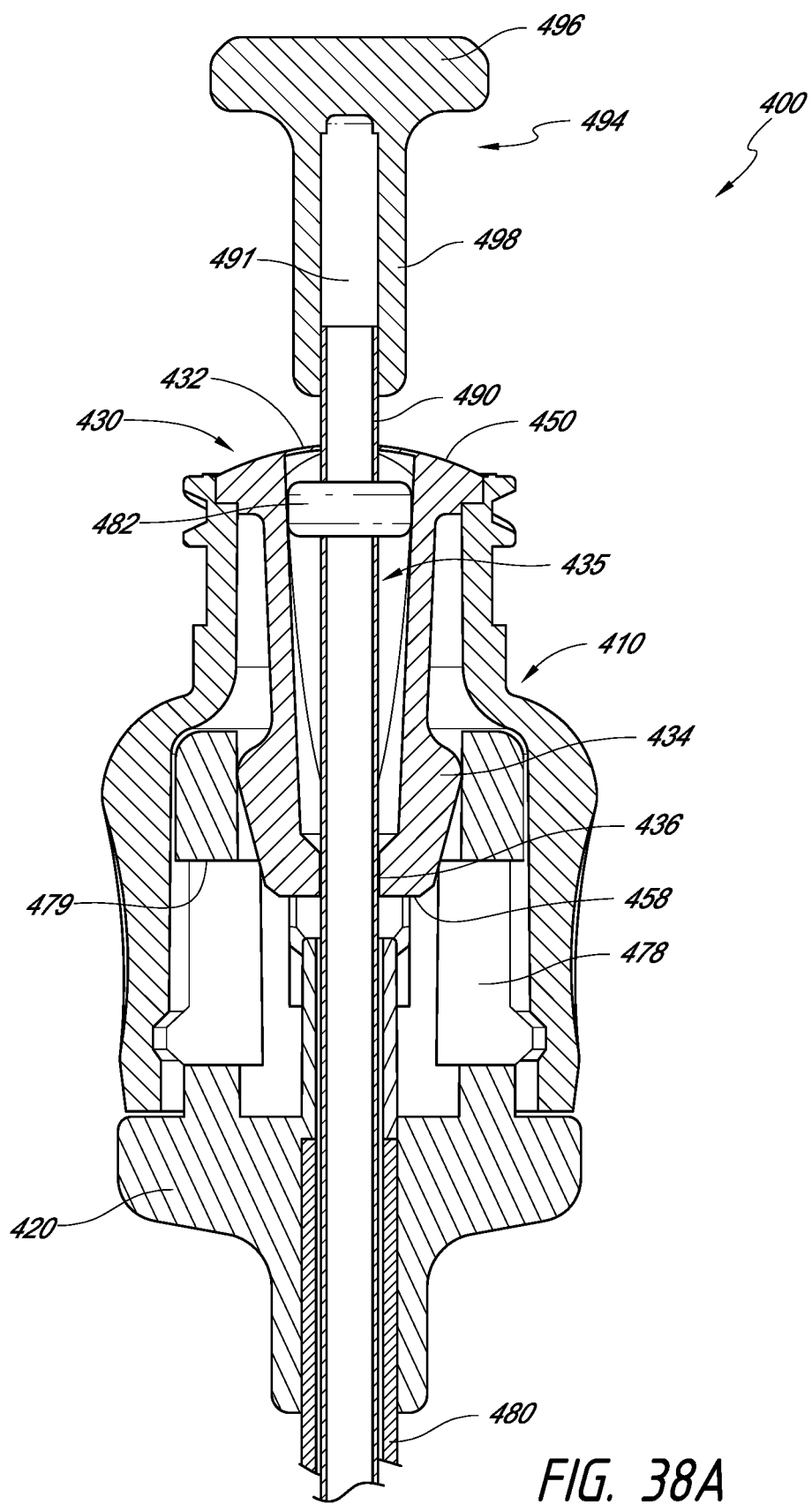
FIG. 38A is a cross sectional view of the catheter assembly of FIG. 37A in the first stage.
Figure 38B:
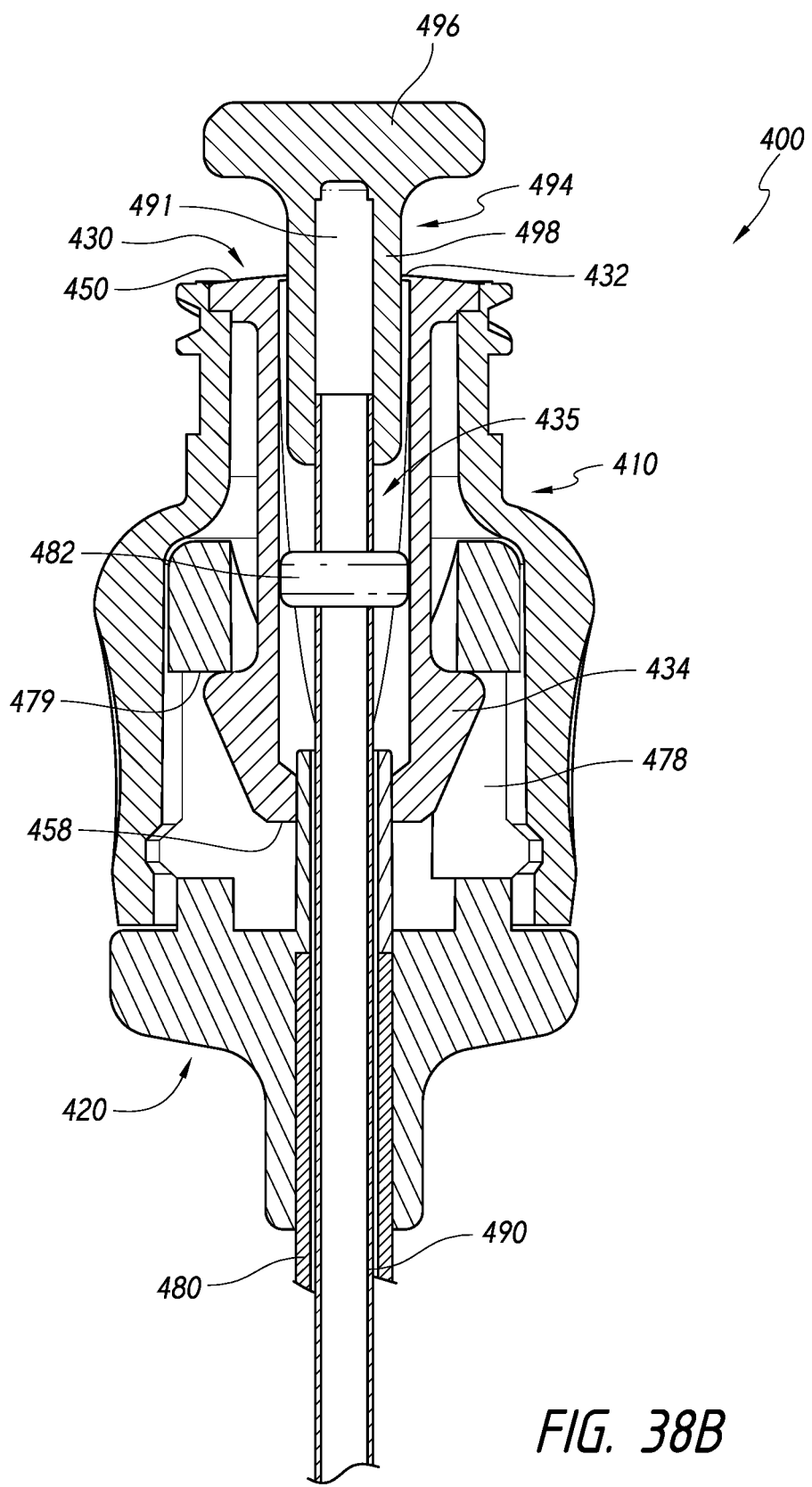
FIG. 38B is a cross sectional view of the catheter assembly of FIG. 37A in the second stage.

FIGS. 38A and 38B illustrate a cross-sectional view of this process. FIG. 38A is a cross-sectional view of the catheter assembly when positioned as illustrated in FIG. 37A, and FIG. 38B is a cross-sectional view of the catheter assembly when positioned as illustrated in FIG. 37B. As illustrated, the valve member 430 can function according to various embodiments describe above. For example, the valve member can have a first state or generally relaxed position as illustrated in FIG. 38A and a second state as illustrated in FIG. 38B. In the second state, as above, the valve member can be in greater tension relative to a longitudinal axis of the valve member. In some embodiments, the shoulders 434 of the valve member can be positioned in openings 478 and can be maintained in the second state by the interaction between the shoulders and the upper surface 479 of the openings. The insertion section 498 of the needle hub 494 can function similarly to an insertion device, as described above. Thus, for example, when the needle hub is moved distally in order to expose the tip of the needle, the insertion section of the needle hub can pass through the slit 432 of the valve member and into the internal cavity 435 of the valve member. The insertion section can contact the walls of the internal cavity, and as the needle hub is inserted further the insertion section can push the valve member into a second state.

In some embodiments, the catheter assembly 400 can include a needle guard 482 positioned around the needle 490. The needle guard can be designed according to aspects of any needle guard known in the art. See, for example, filings from B-Braun and other third parties, incorporated herein by reference in their entireties for all they disclose and attached hereto as Exhibit A. Preferably, the needle guard can be sized to fit within the internal cavity 435 of the valve member. The needle can move relative to the needle guard, although in some embodiments an amount of friction can exist between the needle guard and the needle such that the needle guard may move within the internal cavity as the needle moves within the internal cavity. In some embodiments, a needle guard 482 may have a large enough outer diameter to engage the internal cavity and to move the valve into the second state when the needle hub is moved distally to expose the tip of the needle.

As the needle is positioned within the vasculature of a patient, the catheter hub 402 can be moved toward the patient such that the catheter 480 also enters the vasculature of the patient. While the catheter hub is being moved toward the patient or after the catheter has been positioned within the patient's vasculature, the needle 490 can be removed from the patient and from the catheter hub. As the needle is withdrawn, the needle guard will preferably be configured to catch as it passes through the slit 432, allowing the needle to be slid relative to the needle guard. In some embodiments, the needle can have a notch or other feature at its distal end that can be configured to interact with a corresponding feature of the needle guard. As the needle is withdrawn and the distal end of the needle begins to leave the valve member, the two features can catch and the needle can pull the needle guard through the slit of the valve member. The needle guard can then cover the tip 492 of the needle, helping to prevent any accidental sticks or punctures.

In some embodiments, the needle hub 494 can be formed of a clear, transparent, or translucent material and can have a hollow section 491 that is configured to receive blood from the needle when the needle is positioned within a patient's vasculature. This can allow a clinician to visually verify that the needle is properly positioned. Similarly, the catheter 480 can be formed of a clear, transparent, or translucent material, allowing the clinician to see when the catheter has entered the vasculature and is in communication with the patient's blood stream. In addition, as described above, one or more sections of the catheter hub 402, including the first housing 410, the second housing 420, or the valve member 430 can be clear, transparent, or translucent to facilitate viewing of the internal components and fluid path within the catheter hub.

Because the valve member was in the first state while the catheter assembly was stored and only entered the second state during the process of inserting the catheter into the patient, a compression set can be minimized or avoided altogether. In part, this is because tensioning the valve member along a longitudinal axis of the catheter hub 402 can create compression in a plane perpendicular to the longitudinal axis at the top 450 of the valve member. This can make the sides of the slit 432 press more tightly together than they would do in the first state, increasing the amount of fluid pressure that the slit can resist during the process of inserting the catheter into a patient and after the needle is removed.

Figure 39A:
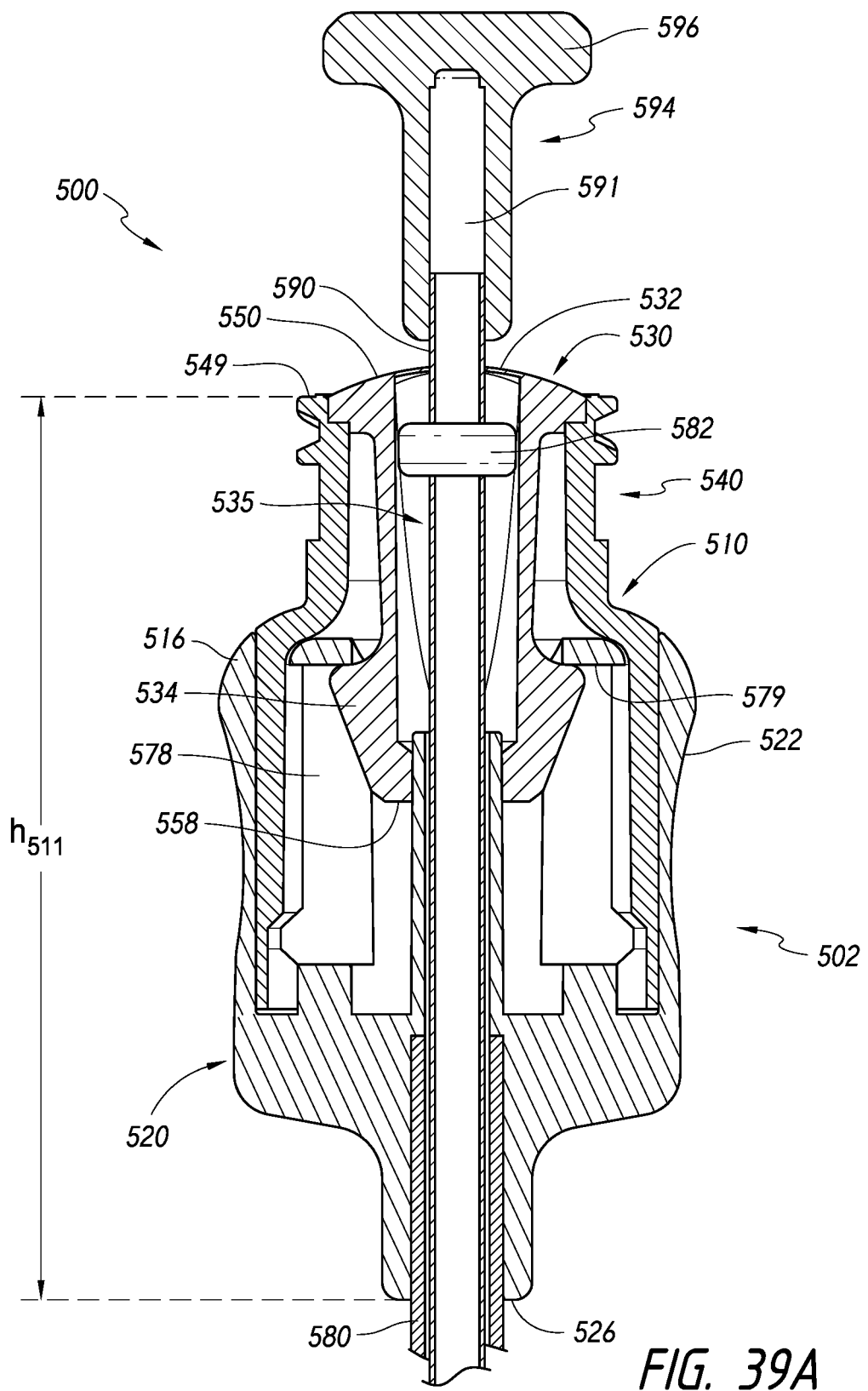
FIG. 39A is a cross sectional view of one embodiment of a catheter assembly in a first stage.
Figure 39B:
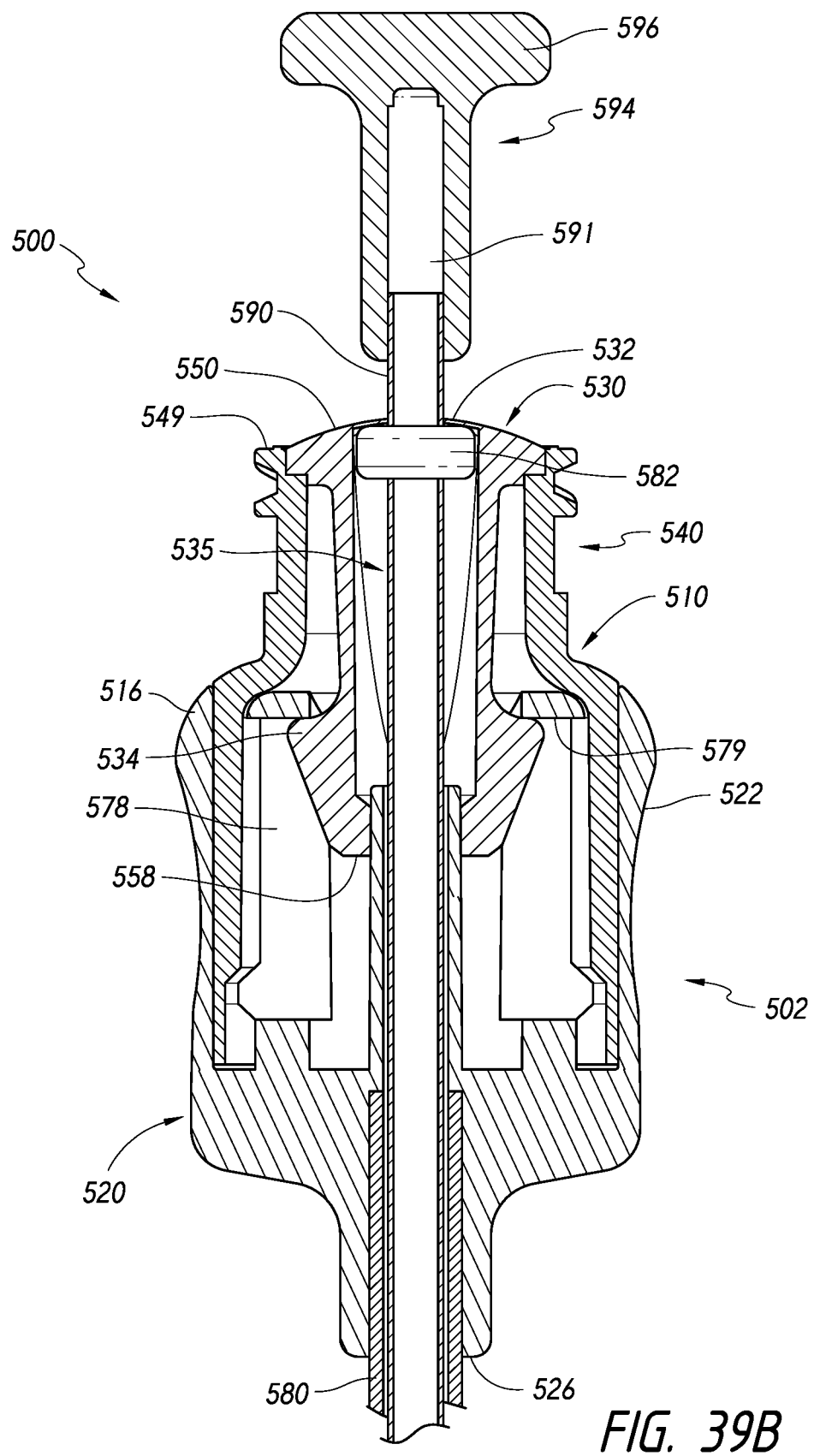
FIG. 39B is a cross sectional view of the catheter assembly of FIG. 39A.
Figure 39C:
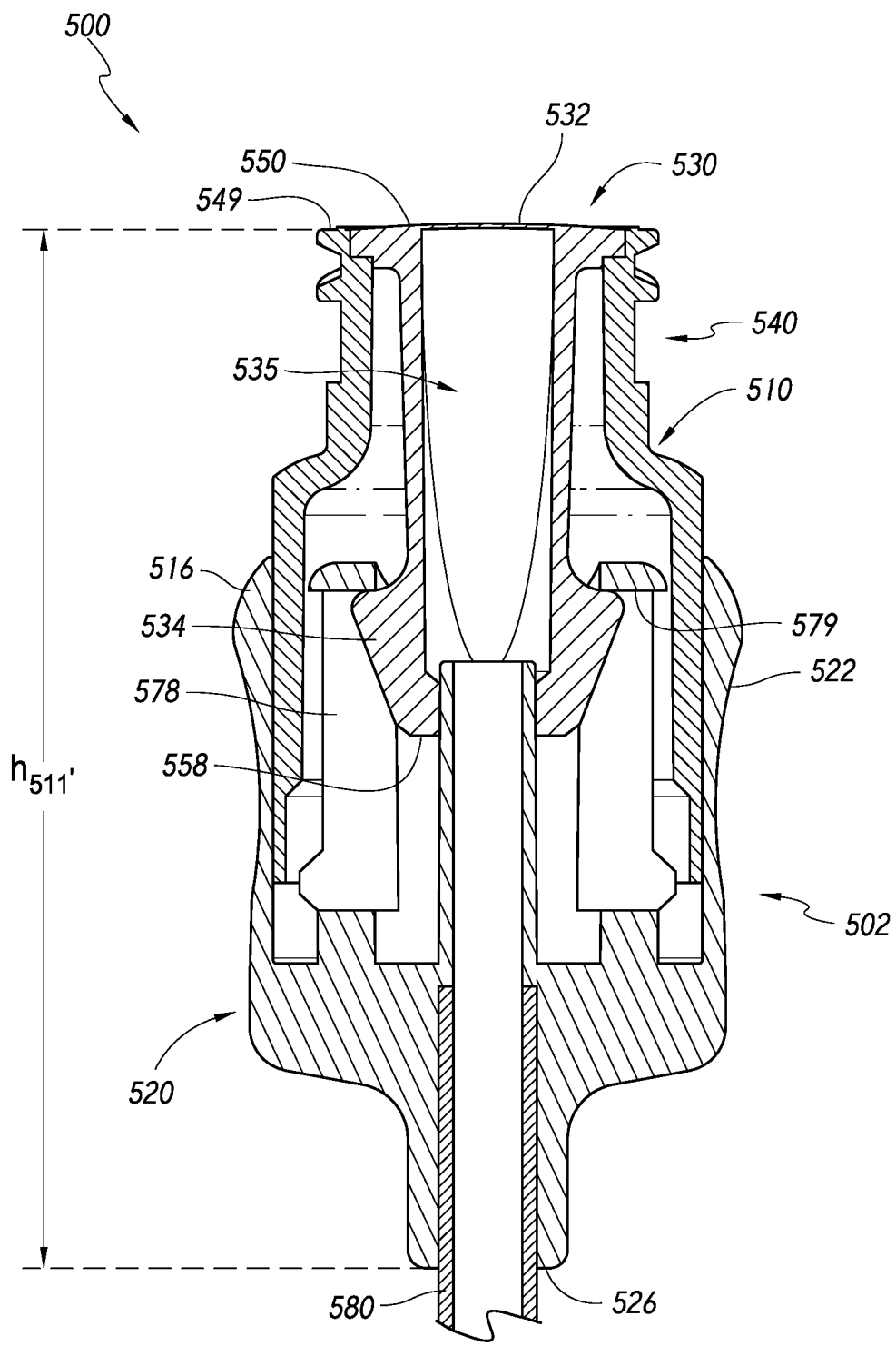
FIG. 39C is a cross sectional view of the catheter assembly of FIG. 39A in a stage position.

FIGS. 39A through 39C illustrate a different embodiment of a catheter assembly 500 that can be used to move the valve member from a first state to a second state. FIGS. 39A and 39B illustrate the catheter assembly in a first stage and FIG. 39C illustrates the catheter assembly in a second stage. The illustrated embodiment can be similar to previous embodiments, but in the first, relaxed state the shoulders 534 of the valve member 530 are preferably positioned within openings 478 of the second housing 520 within the catheter hub 502. Thus, in the first state an upper section of the valve member can be attached to the first housing and a lower section of the valve member can be attached to the second housing.

In some embodiments, the second housing 520 and the first housing 510 of the catheter hub 502 can move relative to each other. In some embodiments, the relative movement between the housings can move the catheter hub from a first stage to a second stage. In some embodiments, the relative movements between the housings can also move the valve member 530 from its first state to its second state, and similarly transition the catheter assembly from its first stage to its second stage. In some embodiments, the valve member can be in the first state when the catheter hub is in the first stage, and the valve member can be in the second state when the catheter hub is in the second stage. In some embodiments, when the catheter hub is in the first stage the catheter hub can have a first height $h_{511}$ measured from a bottom surface 526 of the second housing to a top surface 549 of the first housing. In some embodiments, when the catheter hub is in the second stage, the catheter hub can have a second height $h_{511'}$ greater than the first height. As illustrated in FIG. 39C, when the second housing moves relative to the first housing the openings 578 can move as well, stretching the valve member 530 into the second state.

In some embodiments, the difference between the first height and the second height can be such that the valve member moves from the first state to the second state according to the various embodiments described above. For example, as described above, the ratio of the valve member height in the second state to the height in the first state can be greater than or equal to about 1.0 and/or less than or equal to about 1.8. In some embodiments, the ratio can be greater than or equal to about 1.1 and/or less than or equal to about 1.3.

In some embodiments, the ratio of the second height $h_{511'}$ to the first height $h_{511}$ can be greater than or equal to approximately 1.02 and/or less than or equal to approximately 1.2. In some embodiments, the ratio of the second height $h_{511'}$ to the first height $h_{511}$ can be greater than or equal to approximately 1.04 and/or less than or equal to approximately 1.15. In some embodiments, the ratio of the second height $h_{511'}$ to the first height $h_{511}$ can be greater than or equal to approximately 1.06 and/or less than or equal to approximately 1.12.

In some embodiments, the catheter assembly 500 can be configured such that removing the needle 590 from the catheter hub moves the catheter hub from the first stage into the second stage. This can provide the advantage of ensuring that a clinician using the catheter assembly according to standard procedures will move the catheter assembly into a second stage in a passive manner, thus limiting or preventing compression set without having to perform any new steps. In some embodiments, this can be achieved by providing a needle guard that provides a resistive force when removing the needle.

For example, with reference to FIG. 39A, a needle guard 582 can be positioned around the needle 590. The needle guard can be completely within the internal cavity 535 of the valve member 530 or can be positioned partially within the internal cavity such that a portion of the needle guard is within the slit 532. Additionally, as illustrated, the second housing 520 can have an outer surface 522 positioned such that a clinician, when grasping the catheter hub 502, will grasp the second housing. In some embodiments, a portion of the second housing can surround a portion of the first housing 510. In some embodiments, the second housing can at least partially define a shoulder 516 that is adjacent the luer connector region 540.

When the clinician is grasping the second housing 520, any resistive force provided by the needle guard 582 or other component of the needle 590 or needle hub 594 when it is pulled through the slit 532 will tend to separate the first housing 510 from the second housing. This can move the catheter hub from the first stage to the second stage. In some embodiments, the catheter hub can have a mechanical lock, snap, or other mechanism that tends to keep the catheter hub in the second stage once it moves into the second stage.

FIG. 39B illustrates a needle guard 582 that has been pulled up from a position within the valve cavity 535 to a position against the slit 532 as the needle 590 is withdrawn. In some embodiments, the needle guard slides freely around the needle and the needle guard does not move against the slit until it engages with the tip of the needle. In some embodiments, as mentioned above, the needle guard is initially positioned partially within the valve cavity and partially through the slit. In such embodiments, the portion of the needle guard within the slit is preferably as small as possible to help minimize any potential compression set. Regardless of the initial positioning of the needle guard, in some embodiments the needle guard preferably does not fully pass through the slit and out of the valve cavity until it engages the tip of the needle.

The needle guard and the valve member can be sized and configured such that the force required to move the needle guard through the slit is sufficient to move the catheter hub from the first stage to the second stage. Preferably, the needle guard is also sized such that moving it through the slit does not damage the valve member. In some embodiments, a lubricant can be applied to the needle and/or the needle guard in order to help prevent tearing or damage to the slit or valve member.

Figure 40:
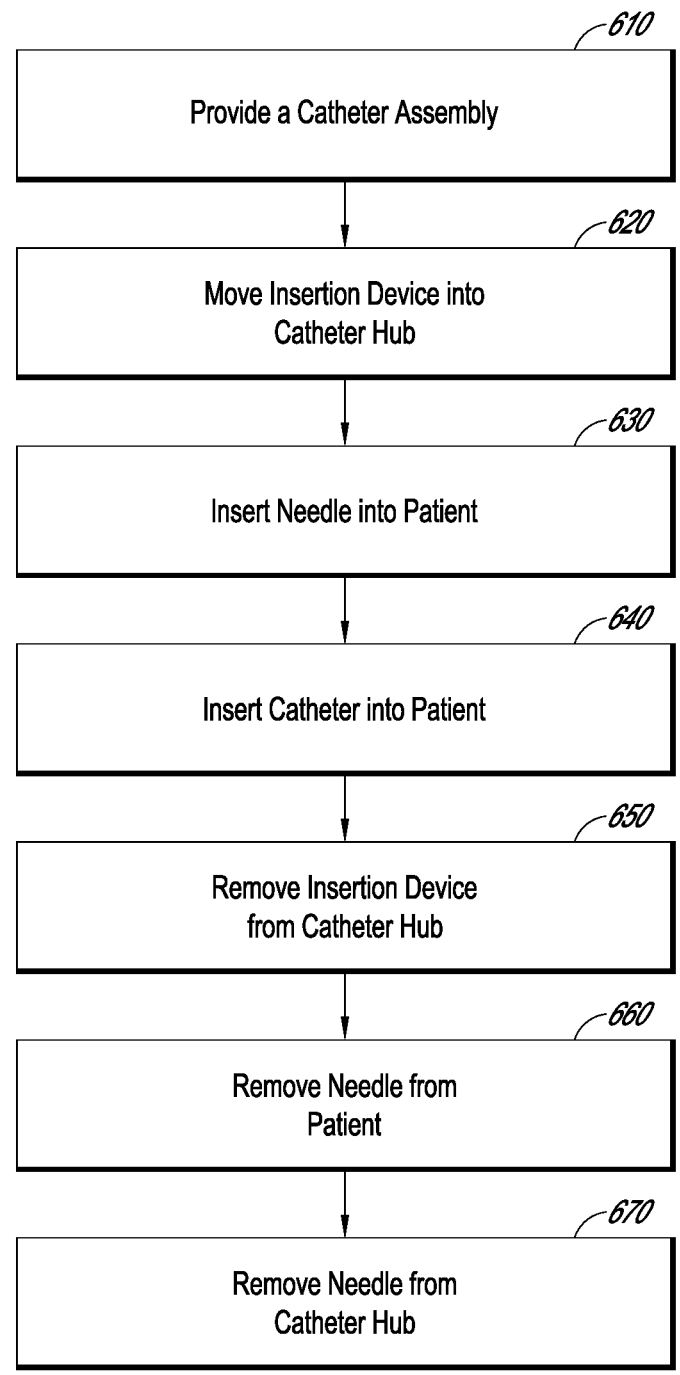
FIG. 40 is a flow chart of one embodiment of a method for using a catheter assembly.

FIG. 40 illustrates a block diagram of a method for using a catheter assembly. In a first step 610 of the method, a catheter assembly can be provided. The catheter assembly can be configured according to any of the embodiments discussed above with respect to FIGS. 37A through 38B. In a second step 620, an insertion device can be inserted into a catheter hub to move a valve member from a first state to a second state. The insertion device can be the insertion section of a needle hub, as described above, or it can be another element attached to the needle or a separate device entirely.

In a third step 630, a needle can be inserted into a patient, and in a fourth step 640 a catheter can be inserted into the patient, such as by sliding over the needle. In a fifth step 650, the insertion device can be removed from the catheter hub. In some embodiments, such as if the insertion device is not attached to the needle, the insertion device can be removed prior to inserting the needle into the patient. In a sixth step 660, the needle is removed from the patient, and in a seventh step 670 the needle is removed from the catheter hub. In some embodiments, various steps can be performed simultaneously. For example, in some embodiments, the second and third steps can be performed simultaneously. In some embodiments, the third and fourth steps can be performed simultaneously. In some embodiments, the second, third, and fourth step scan be performed simultaneously. Similarly, in some embodiments, the fifth and sixth steps can be performed simultaneously. In some embodiments, the fifth, sixth, and seventh steps can be performed simultaneously.

Figure 41:
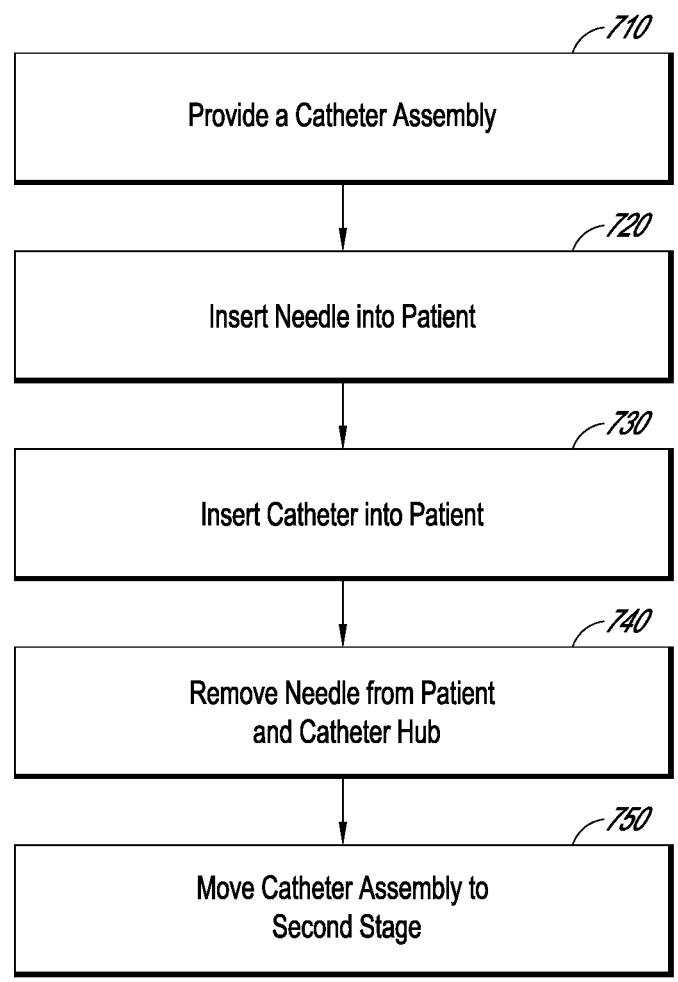
FIG. 41 is a flow chart of one embodiment of a method for using a catheter assembly.

FIG. 41 illustrates a block diagram of another method for using a catheter assembly. In a first step 710 of the method, a catheter assembly can be provided. The catheter assembly can be configured according to any of the embodiments discussed above with respect to FIGS. 39A through 39C. In a second step 720 a needle is inserted into a patient, and in a third step 730 a catheter is inserted into the patient, such as by sliding over the needle. In a fourth step 740, the needle can be removed from the patient and catheter hub, and in a fifth step 750 the catheter assembly can be moved to a second stage. In some embodiments, this can include, for example, lengthening the catheter hub, as described above. In some embodiments, this can include using an insertion device to move a valve of the catheter hub from a first state to a second state. In some embodiments, moving the catheter assembly to the second stage can be performed prior to inserting a needle into a patient. In some embodiments, also as described above, the catheter assembly can be moved to a second stage as the needle is being removed from the catheter hub or even after the needle is removed. In some embodiments, various other steps can be performed simultaneously. For example, in some embodiments, the second and third steps can be performed simultaneously.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A medical connector for permitting fluid flow between a first medical device and a second medical device, the medical connector comprising:
    an upper housing comprising an upper end configured to receive a first medical device and at least two downward projections centered about a central longitudinal axis of the upper housing, the at least two downward projections each having a first angular width at a base and alignment surfaces that each extend from a side edge of the downward projection to an edge at a lower tip of the projection;
    a seal element fixed to the upper housing; and
    a lower housing comprising a lower end configured to receive a second medical device, at least two upward projections centered around a central longitudinal axis of the lower housing, each upward projection having two alignment surfaces that each extend from a side edge of the upward projection to an edge at an upper tip of each projection, and at least two gaps having a second angular width and bounded on either side by adjacent upward projections;
    wherein the upper and lower housings are configured to be joined together, each downward projection configured to fit within one of the at least two gaps; and
    wherein the alignment surfaces of the downward and upward projections comprise matching helical surfaces.

2. The medical connector of claim 1, wherein the first angular width is less than the second angular width.

3. The medical connector of claim 2, wherein the first angular width and second angular width are sized such that each of the downward projections fits flush within one of the at least two gaps.

4. The medical connector of claim 1, wherein the alignment surfaces of the downward projections and the alignment surfaces of the upward projections are configured such that if each of the downward projections is not aligned with one of the at least two gaps when the upper and lower housings are joined together the alignment surfaces of the downward projections will contact the alignment surfaces of the upward projections and tend to rotate the upper and lower housings relative to each other until each of the downward projections is aligned with one of the at least two gaps.

5. The medical connector of claim 1, wherein the at least two upward projections each comprise an opening passing through the projection.

6. The medical connector of claim 5, wherein the seal element comprises a central body and two shoulders extending outward from the central body on opposite sides thereof, the shoulders oriented such that when the upper and lower housings are joined each shoulder is aligned with the opening of one of the at least two upward projections.

7. The medical connector of claim 1, wherein each alignment surface of the downward projections has a height and width measured from an outermost point of the side edge of the downward projection to the outermost point of the edge at the lower tip of the downward projection.

8. The medical connector of claim 7, wherein the ratio of the height to the width is between approximately 0.5 and approximately 1.5.

9. The medical connector of claim 1, wherein each alignment surface of the upward projections has a height and width measured from an outermost point of the side edge of the upward projection to the outermost point of the edge at the upper tip of the upward projection.

10. The medical connector of claim 9, wherein the ratio of the height to the width is between approximately 0.5 and approximately 1.5.

11. The medical connector of claim 1, wherein the seal element comprises a central body and two shoulders extending outward from the central body on opposite sides thereof, the shoulders oriented such that when the upper and lower housings are joined each shoulder contacts and is aligned with one of the at least two upward projections.

12. The medical connector of claim 11, wherein the seal element comprises a flexible material.

13. The medical connector of claim 12, wherein when each shoulder contacts one of the at least two upward projections, the flexible material of the seal member compresses from the pressure of contact with the at least two upward projections, allowing the seal member to fit between the at least two upward projections.

* * * * *